United States Patent
Ohkuchi et al.

(10) Patent No.: US 6,348,468 B1
(45) Date of Patent: Feb. 19, 2002

(54) PYRIDAZINE COMPOUNDS AND COMPOSITIONS CONTAINING THE SAME

(75) Inventors: Masao Ohkuchi, Tokorozawa; Yoshinori Kyotani, Higashiyamato; Hiromichi Shigyo, Fuchu; Tomoyuki Koshi, Shiki; Takahiro Kitamura, Higashimurayama; Tadaaki Ohgiya, Tokorozawa; Takayuki Matsuda; Yukiyoshi Yamazaki, both of Higashimurayama; Natsuyo Kumai, Fujimi; Kyoko Kotaki, Sakado; Hideo Yoshizaki, Sayama; Yuriko Habata, Higashiyamato, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/530,949

(22) PCT Filed: Nov. 9, 1998

(86) PCT No.: PCT/JP98/05023

§ 371 Date: May 15, 2000

§ 102(e) Date: May 15, 2000

(87) PCT Pub. No.: WO99/25697

PCT Pub. Date: May 27, 1999

(30) Foreign Application Priority Data

Nov. 19, 1997 (JP) .............................................. 9-318132
Nov. 19, 1997 (JP) .............................................. 9-318133

(51) Int. Cl.[7] ...................... A61K 31/501; A61K 31/50; C07D 401/04; C07D 237/14; C07D 237/18
(52) U.S. Cl. ............................. 514/252.03; 514/236.5; 514/247; 514/252.01; 514/252.02; 544/114; 544/238; 544/239
(58) Field of Search .................. 544/239, 238, 544/114; 514/247, 236.5, 252.01, 252.02, 252.03

(56) References Cited

U.S. PATENT DOCUMENTS 5,591,729 A * 1/1997 Harrison et al. .............. 514/85

FOREIGN PATENT DOCUMENTS

| JP | 1-258671 | * 10/1989 |
| JP | 5-507087 | * 10/1993 |
| WO | 96/36608 | * 11/1996 |
| WO | WO 98/41511 | 9/1998 |
| WO | WO 99/10331 | 3/1999 |
| WO | WO 99/10332 | 3/1999 |
| WO | WO 00/24719 | 5/2000 |

OTHER PUBLICATIONS

El–Kassaby et al., Indian J.of Chemistry, 30B, pp. 662–665, 1991.*
Nannini et al., Eur. J.Med.Chem. 1, pp. 53–60, 1979.*
McEvoy et al. J.Med. Chem. 17, pp. 281–286, 1974.*
Abstract of JP 1–258671, Oct. 16, 1989.*
Livingston, Journal of Cellular Biochemistry, 64, pp. 19–26, 1997.*
Abstract for WO 2000/50408 (Aug. 13, 2000).

* cited by examiner

Primary Examiner—Emily Bernhardt
(74) Attorney, Agent, or Firm—Oblon, Spivak, McClelland, Maier & Neustadt, P.C.

(57) ABSTRACT

This invention relates to pyridazine derivatives represented by the formula (1):

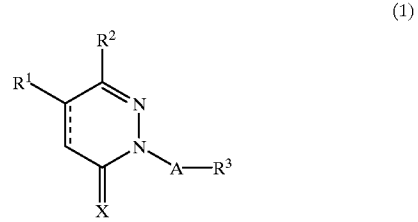

wherein $R^1$ represents a (substituted) aryl group, $R^2$ represents a phenyl group substituted at 4-position by a lower alkoxyl group or a lower alkylthio group, $R^3$ represents a lower alkoxyl group, a halogenated lower alkyl group, a lower cycloalkyl group, a (subsituted) aryl group, a (substituted) aryloxy group, a (substituted) nitrogen-containing heterocyclic ring residue, a (substituted) aminocarbonyl group or a lower alkylcarbonyl group, A represents a single bond, a lower alkylene group or a lower alkenylene group, X represents O or S, and the dashed line indicates that the carbon-carbon bond between the 4-position and the 5-position is a single bond or a double bond, or salts thereof; and also to medicines containing them as effective ingredients. These compounds have excellent inhibitory activity against interleukin-1β production, and are useful as preventives and therapeutics for immune system diseases, inflammatory diseases, ischemic diseases and the like.

10 Claims, No Drawings

PYRIDAZINE COMPOUNDS AND COMPOSITIONS CONTAINING THE SAME

DESCRIPTION

1. Technical Field

This invention relates to novel pyridazine derivatives, which have excellent inhibitory activity against interleukin-1β production and are useful for the prevention and treatment of immune system diseases, inflammatory diseases, ischemic diseases and the like, and also to medicines containing them as effective ingredients.

2. Background Art

In many diseases, for example, rheumatism, arthritis, osteoporosis, inflammatory colitis, immune deficiency syndrome, ichorrhemia, hepatitis, nephritis, ischemic diseases, insulin-dependent diabetes mellitus, arterial sclerosis, Parkinson's disease, Alzheimer's disease, leukemia and the like, stimulation of interleukin-1β production, an inflammatory cytokine, is observed. This interleukin-1β serves to induce synthesis of an enzyme which is considered to take part in inflammation like collagenase and PLA2 and, when intra-articularly injected to animals, causes multi-articular destruction highly resembling rheumatoid arthritis. On the other hand, interleukin-1β is controlled in activity by interleukin-1β receptor, soluble interleukin-1 receptor and interleukin-1 receptor antagonist.

From research conducted making use of recombinants of these bioactivity-inhibiting substances, anti-interleukin-1β antibodies and anti-receptor antibodies against various disease models, interleukin-1β has been found to play an important role in the body, leading to an increasing potential of substances having interleukin-1β inhibitory activity as therapeutics for such diseases.

For example, immunosuppressors and steroids which are used for the treatment of rheumatism out of such many diseases have been reported to inhibit the production of interleukin-1β. Even among medicaments currently under development, KE298, a benzoylpropionic acid derivative [The Japanese Society of Inflammation (11th), 1990], for example, has been reported to have inhibitory activity against interleukin-1β production although it is an immunoregulator. Inhibitory activity against interleukin-1β production is also observed on a group of compounds which are called "COX-2 selective inhibitors", for example, nimesulide as a phenoxysulfonanilide derivative (DE 2333643), T-614 as a phenoxybenzopyran derivative (U.S. Pat. No. 4,954,518), and tenidap (hydroxyindole derivative) as a dual inhibitor (COX-1/5-LO).

For all of these compounds, however, interleukin-1β production inhibitory activity is not their primary action so that their inhibitory activity against interleukin-1β production is lower than their primary action.

In recent years, increasingly active research is under way for the synthesis of compounds with a focus placed on inhibitory activity against interleukin-1β production. Production inhibitors synthesized in such research can be classified into a group of compounds which inhibit the transfer process of an inflammatory signal to a cell nucleus and another group of compounds which inhibit an enzyme ICE that functions in the processing of a precursor of interleukin-1β. Known examples of compounds presumed to have the former action include SB203580 [Japanese Language Laid-Open (Kokai) Publication (PCT) No. HEI 7-503017], FR167653 (Eur. J. Pharm., 327, 169–175, 1997), E-5090 (EP 376288), CGP47969A (Gastroenterology, 109, 812–828, 1995), hydroxyindole derivatives (Eur. J. Med. Chem. 31, 187– 198, 1996), and triarylpyrrole derivatives (WO 97/05878), while known examples of compounds presumed to have the latter action include VE-13,045 which is a peptide compound (Cytokine, 8(5), 377–386, 1996).

None of these compounds can however exhibit sufficient inhibitory activity against interleukin-1β production.

On the other hand, a variety of 5,6-diphenylpyridazine derivatives are known to have analgesic and anti-inflammatory action (EUR. J. MED. CHEM., 14, 53–60, 1979). Absolutely nothing has however been known with respect to inhibitory activity against interleukin-1β production by these 5,6-diphenylpyridazine derivatives.

Accordingly, an object of the present invention is to provide a compound having excellent inhibitory activity against interleukin-1β production and also a medicine containing it as an effective ingredient.

DISCLOSURE OF THE INVENTION

Under such circumstances, the present inventors have proceeded with an extensive investigation. As a result, it has been found that pyridazine derivatives represented by the below-described formula (1) have excellent inhibitory activity against interleukin-1β production and are useful as medicines for the prevention and treatment of immune system diseases, inflammatory diseases, ischemic diseases and the like, leading to the completion of the present invention.

Namely, the present invention provides a pyridazine derivative represented by the following formula (1):

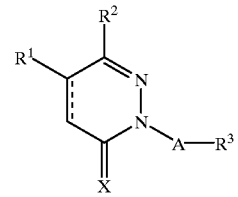

wherein $R^1$ represents a substituted or unsubstituted aryl group, $R^2$ is a phenyl group substituted at least at 4-position by a lower alkoxyl group, a lower alkylthio group, a lower alkylsulfinyl group or a lower alkylsulfonyl group, and optionally has one or more substituents at the remaining positions, $R^3$ represents a hydrogen atom, a lower alkoxyl group, a halogenated lower alkyl group, a lower cycloalkyl group, a substituted or unsubstituted aryl group, a substituted or unsubstituted aryloxy group, a substituted or unsubstituted, nitrogen-containing heterocyclic ring residue, a substituted or unsubstituted aminocarbonyl group, or a lower alkylcarbonyl group, A represents a single bond or a linear or branched lower alkylene group or lower alkenylene group, X represents an oxygen atom or a sulfur atom, and the dashed line indicates that the carbon-carbon bond between the 4-position and the 5-position is a single bond or a double bond, with the proviso that A is a single bond when $R^3$ is a halogenated lower alkyl group and that the following combinations are excluded: $R^1$ and $R^2$ are 4-methoxyphenyl groups, X is an oxygen atom, the carbon-carbon bond at the 4-position and the 5-position is a double bond, A is a single bond, and $R^3$ is a hydrogen atom or a 2-chloroethyl group; or a salt thereof.

Further, the present invention also provides a medicine comprising the pyridazine derivative (1) or the salt thereof as an effective ingredient.

Furthermore, the present invention also provides a pharmaceutical composition comprising the pyridazine derivative (1) or the salt thereof and a pharmaceutically acceptable carrier.

Moreover, the present invention also provides use of the pyridazine derivative (1) or the salt thereof as a medicine.

In addition, the present invention also provides a method for treating a disease caused by stimulation of interleukin-1β production, which comprises administering the pyridazine derivative (1) or the salt thereof.

As will be demonstrated in tests to be described subsequently herein, the inhibitory activity against interleukin-1β production by the pyridazine derivative (1) or the salt thereof is extremely strong and reaches 100 to 1,000 times as high as the action of the abovedescribed known 5,6-diphenylpyridazine derivatives (EUR. J. MED. CHEM. 14, 53–60, 1979).

BEST MODE FOR CARRYING OUT THE INVENTION

The pyridazine derivative according to the present invention is represented by the formula (1). In the formula, illustrative of the aryl group represented by $R^1$ can be phenyl, naphthyl and pyridyl, with phenyl and pyridyl being particularly preferred. These aryl groups may contain 1 to 3 substituents. Examples of such substituents can include halogen atoms, lower alkyl groups, lower alkoxyl groups, lower alkylthio groups, lower alkylsulfinyl groups, lower alkylsulfonyl groups, carboxyl group, lower alkoxycarbonyl groups, nitro group, amino group, and lower alkylamino groups. Here, illustrative of the halogen atoms can be fluorine, chlorine, bromine and iodine. The lower alkyl groups are those containing 1 to 6 carbon atoms, for example, methyl, ethyl, n-propyl, isopropyl and n-butyl. Illustrative of the lower alkoxyl groups can be those containing 1 to 6 carbon atoms, for example, methoxy, ethoxy and propoxy. Illustrative of the lower alkylthio groups can be those containing 1 to 6 carbon atoms, for example, methylthio, ethylthio and propylthio. Illustrative of the lower alkylsulfinyl groups can be those containing 1 to 6 carbon atoms, for example, methylsulfinyl, ethylsulfinyl and propylsulfinyl. Illustrative of the lower alkylsulfonyl groups can be those containing 1 to 6 carbon atoms, for example, methylsulfonyl, ethylsulfonyl and propylsulfonyl. Illustrative of the lower alkoxycarbonyl groups can be those having alkoxyl groups each of which contains 1 to 6 carbon atoms, for example, methoxycarbonyl, ethoxycarbonyl and propoxycarbonyl. Illustrative of the lower alkylamino groups can be those having one or two alkyl groups each of which contains 1 to 6 carbon atoms, for example, methylamino, dimethylamino, ethylamino and propylamino. The lower alkyl moieties in these substituents may be linear, branched or cyclic.

Preferred as $R^1$ is a phenyl or pyridyl group, which may be substituted by 1 to 3 substituents selected from halogen atoms and lower alkoxyl groups, these substituents being preferably present at 3-, 4- or 5-position.

Preferred as $R^2$ is a phenyl group, which may be substituted at 4-position by a lower alkoxyl group, a lower alkylthio group, a lower alkylsulfinyl group or a lower alkylsulfonyl group, and at the other position by 1 or 2 substituents selected from halogen atoms, lower alkoxyl groups, lower alkylthio groups, lower alkylsulfinyl groups and lower alkylsulfonyl groups. Examples of the halogen atom, lower alkoxyl group, lower alkylthio group, lower alkylsulfinyl group and lower alkylsulfonyl group as the substituents on the phenyl group as $R^2$ include the same groups as those recited as $R^1$. These substituents are preferably positioned at only 4-position, at 3- or 4-position, or at any of 3-, 4- or 5-position.

Illustrative of the lower alkoxyl group and the substituted or unsubstituted aryl group out of those represented by $R^3$ can be similar to those exemplified above in connection with $R^1$.

Illustrative of the halogenated lower alkyl group can be lower alkyl groups substituted by one or more halogen atoms as exemplified above in connection with $R^1$.

Examples of the lower cycloalkyl group can include those having 3 to 8 carbon atoms, for example, cyclopropyl, cyclobutyl, cyclopentyl and cyclohexyl.

Illustrative of the aryloxy group can be a phenyloxy group, which may contain similar substituent or substituents as in the case of $R^1$.

Illustrative of the nitrogen-containing heterocyclic ring residue can be saturated, nitrogen-containing heterocyclic ring residue such as piperidino, piperidyl, piperazino and morpholino; and nitrogen-containing aromatic heterocyclic ring residue such as pyridyl. These residue may contain similar substituents as in the case of $R^1$. Further, each of them may additionally contain one or more carbonyl groups bonded thereto.

The aminocarbonyl group may contain similar substituents as in the case of $R^1$ and also aralkyl groups such as benzyl and phenethyl.

Illustrative of the lower alkylcarbonyl group can be those containing 1 to 6 carbon atoms, for example, methylcarbonyl and ethylcarbonyl.

Preferred examples of $R^3$ can include a hydrogen atom; lower alkoxyl groups; halogenated lower alkyl groups; lower cycloalkyl groups; phenyl, pyridyl and phenyloxy groups each of which may be substituted by 1 to 3 substituents selected from halogen atoms, lower alkyl groups, lower alkoxyl groups, carboxyl group, lower alkoxycarbonyl groups, nitro group, amino group, lower alkylamino groups and lower alkylthio groups; substituted or unsubstituted piperidino, piperidyl, piperazino and morpholino groups; and substituted or unsubstituted aminocarbonyl groups; and lower alkylcarbonyl groups.

Among those represented by A, the lower alkylene group can be a linear or branched one having 1 to 6 carbon atoms, examples of which can include methylene, ethylene and trimethylene. The lower alkenylene group can be a linear or branched one having 2 to 9 carbon atoms, with one having 2 to 6 carbon atoms and 1 to 3 double bonds being preferred. Illustrative can be ethenylene, propenylene, butenylene and butadienylene.

Preferred examples of A can be linear or branched lower alkylene groups having 1 to 6 carbon atoms and linear or branched, lower alkenylene groups having 2 to 9 carbon atoms.

Preferred examples of the pyridazine derivative (1) can include those containing, as $R^1$, a phenyl or pyridyl group substituted by 1 to 3 substituents selected from halogen atoms and lower alkoxy groups; as $R^2$, a phenyl group, which may be substituted at 4-position by a lower alkoxyl group, a lower alkylthio group, a lower alkylsulfinyl group or a lower alkylsulfonyl group, and at the other position by 1 or 2 substituents selected from halogen atoms, lower alkoxyl groups, lower alkylthio groups, lower alkylsulfinyl groups and lower alkylsulfonyl groups; as $R^3$, a hydrogen atom, a lower alkoxyl group, a halogenated lower alkyl group, a lower cycloalkyl group, or a phenyl, pyridyl or phenyloxy group which may be substituted by 1 to 3 substituents selected from halogen atoms, lower alkyl groups, lower alkoxyl groups, carboxyl group, lower alkoxycarbonyl groups, nitro group, amino group, lower alkylamino groups and lower alkylthio groups, a substituted or unsubstituted piperidino, piperidyl, piperazino or morpholino group, a substituted or unsubstituted aminocarbonyl group, or a lower alkylcarbonyl group; and as A, a linear or branched lower alkylene group having 1 to 6 carbon atoms or a linear or branched lower alkenylene group having 2 to 9 carbon atoms.

In the present invention, compounds represented by the following formula (1A) are also preferred:

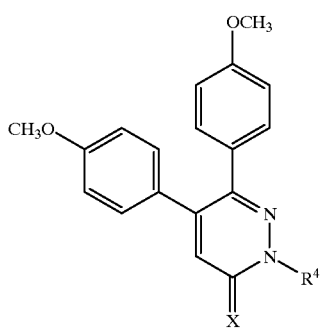

(1A)

wherein $R^4$ represents a linear or branched lower alkyl or lower alkenyl group, a lower cycloalkyl group or a lower cycloalkylmethyl group, and X represents an oxygen atom or a sulfur atom.

In the formula (1A), examples of the lower alkyl group out of those represented by $R^4$ can include linear or branched lower alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. Examples of the lower alkenyl group can include linear or branched lower alkenyl groups having 2 to 6 carbon atoms, preferably 2 to 4 carbon atoms and 1 to 2 double bonds, for example, ethenyl, propenyl, butenyl, isobutenyl and butadienyl. Examples of the lower cycloalkyl group can include those having 3 to 6 carbon atoms, for example, cyclopropyl, cyclobutyl, cyclopentyl and cyclohexyl. Illustrative of the lower cycloalkyl group in the lower cycloalkyl methyl group can be those exemplified above.

Particularly preferred examples of $R^4$ can include alkyl groups having 1 to 4 carbon atoms, alkenyl groups having 2 to 4 carbon atoms, cycloalkyl groups having 3 to 6 carbon atoms, and cycloalkylmethyl groups.

Preferred examples of the pyridazine derivative (1) can include 5,6-bis(4-methoxyphenyl)-2-ethyl-2H-pyridazin-3-one, 5,6-bis(4-methoxyphenyl)-2-methyl-2H-pyridazin-3-one, 5,6-bis(4-methoxyphenyl)-2-isopropyl-2H-pyridazin-3-one, 5,6-bis(4-methoxyphenyl)-2-isobutyl-2H-pyridazin-3-one, 2-allyl-5,6-bis(4-methoxyphenyl)-2H-pyridazin-3-one, 5,6-bis(4-methoxyphenyl)-2-cyclopropyl-2H-pyridazin-3-one, 5,6-bis(4-methoxyphenyl)-2-cyclopropylmethyl-2H-pyridazin-3-one, 5,6-bis(4-methoxyphenyl)-2-cyclopropylmethyl-2H-pyridazine-3-thione, 5,6-bis(4-methoxyphenyl)-2-cyclopentyl-2H-pyridazin-3-one, 5,6-bis(4-methoxyphenyl)-2-cyclopentylmethyl-2H-pyridazin-3-one, 5,6-bis(4-methoxyphenyl)-2-(4-chlorocinnamyl)-2H-pyridazin-3-one, 5-(4-chlorophenyl)-6-(4-methylthiophenyl)-2-benzyl-2H-pyridazin-3-one, 5,6-bis(4-methoxyphenyl)-2-benzyl-2H-pyridazine-3-thione, and 5,6-bis(3-fluoro-4-methoxyphenyl)-2-ethyl-2H-pyridazin-3-one.

No particular limitation is imposed on the salt of the pyridazine (1), said salt also pertaining to the present invention, insofar as it is a pharmacologically acceptable salt. Illustrative can be acid addition salts of mineral acids, such as the hydrochloride, hydrobromide, hydroiodide, sulfate, nitrate and phosphate; and acid addition salts of organic acids, such as the benzoate, methanesulfonate, ethanesulfonate, benzenesulfonate, p-toluenesulfonate, oxalate, maleate, fumarate, tartrate and citrate.

Further, the compounds according to the present invention may exist in the form of solvates represented by hydrates and also in the form of keto-enol tautomers. Such solvates and isomers should also be encompassed by the present invention.

The pyridazine derivatives (1) according to the present invention can be prepared, for example, by the following processes.

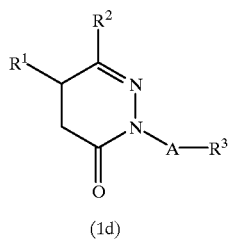

(1d)

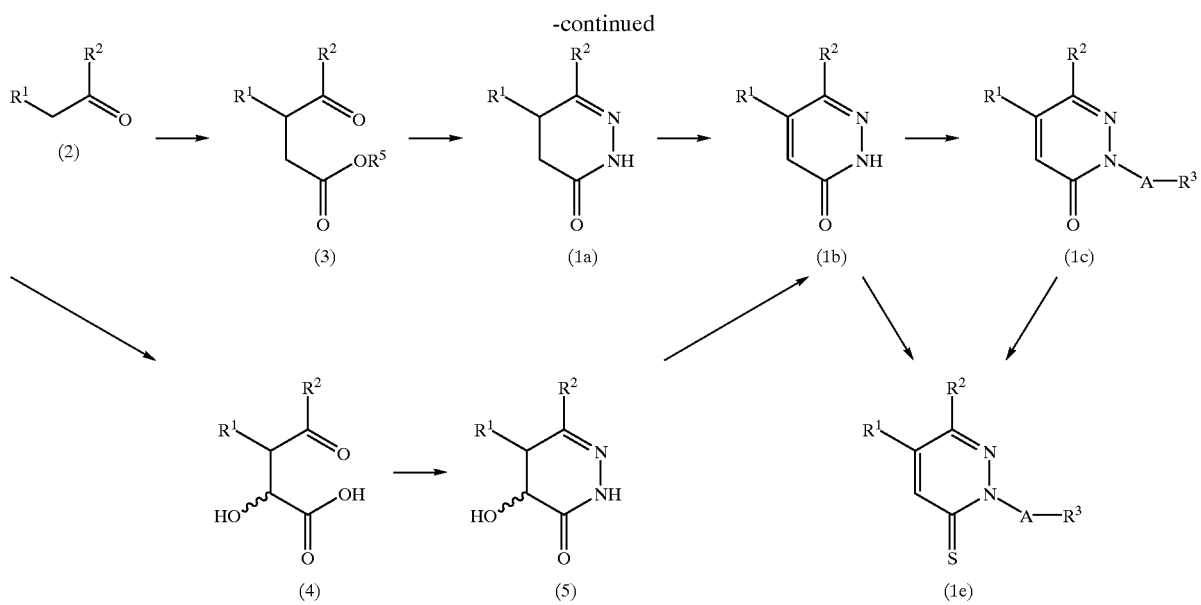

wherein $R^5$ represents a lower alkyl group, and $R^1$, $R^2$, $R^3$ and A have the same meanings as defined above.

A description will be made specifically about respective preparation processes of compounds (1a), (1b), (1c), (1d) and (1e) among the pyridazine derivatives (1).

(1) Preparation of 4,5-dihydro-2H-pyridazin-3-one derivatives (1a: in the formula (1), A is a single bond, $R^3$ is a hydrogen atom, X is an oxygen atom, and a single bond is formed between the 4-position and the 5-position):

A 4,5-dihydro-2H-pyridazin-3-one derivative (1a) can be obtained by reacting a haloacetate ester with a 2-arylacetophenone derivative (2) and then reacting hydrazine hydrate with the resultant product.

The 2-arylacetophenone derivative (2) as the starting material can be prepared, for example, by a known process (YAKUGAKU ZASSHI, 74, 495–497, 1954).

The reaction between the compound (2) and the haloacetate ester can be conducted in the presence of a base in a solvent. Potassium tert-butoxide, lithium diisopropylamide (LDA) or the like can be mentioned as a base usable here, and tetrahydrofuran or the like can be mentioned as a solvent usable here. The reaction is brought to completion at −20 to 40° C. in 1 to 10 hours, preferably at −5 to 25° C. in 2 to 5 hours.

Further, the reaction between the resultant compound (3) and hydrazine hydrate can be conducted in a solvent, and anhydrous hydrazine may be used in place of hydrazine hydrate. As the solvent, a lower alcohol such as ethanol, methanol, n-propanol or isopropanol, tetrahydrofuran, 1,4-dioxane or the like can be used. The reaction is brought to completion at 50 to 150° C. in 5 to 50 hours, preferably at 80 to 100° C. in 10 to 30 hours.

(2) Preparation of 4,5-dihydro-2H-pyridazin-3-one derivatives (1d: in the formula (1), a single bond is formed between the 4-position and the 5-position, and X is an oxygen atom.):

A 2-substituted 4,5-dihydro-2H-pyridazin-3-one derivative (1d) can be obtained by reacting a compound, which is represented by the formula:

wherein $R^3$ and A have the same meanings as defined above, with the compound (3) in the presence of sodium acetate in a solvent.

As a solvent usable in this reaction, methanol, ethanol, n-propanol, isopropanol, dimethylsulfoxide, N,N-dimethylformamide, tetrahydrofuran, 1,4-dioxane or the like can be mentioned. A lower alcohol or a water-containing lower alcohol is particularly preferred. The reaction is brought to completion at 40 to 150° C. in 1 to 80 hours, preferably at 50 to 120° C. in 5 to 50 hours.

(3) Preparation of 2H-pyridazin-3-one derivatives (1b: in the formula (1), A is a single bond, $R^3$ is a hydrogen atom, X is an oxygen atom, and a double bond is formed between the 4-position and the 5-position):

(i) Preparation by a dehydrogenating reaction:

A 2H-pyridazin-3-one derivative (1b) can be obtained by reacting a dehydrogenating agent with the compound (1a) in acetic acid.

As the dehydrogenating agent, bromine, 2,3-dichloro-5,6-dicyano-1,4-benzoquinone (DDQ) or the like can be used. As the solvent, acetic acid or the like is usable. The reaction is brought to completion at 30 to 150° C. in 5 to 50 hours, preferably at 50 to 120° C. in 10 to 30 hours.

(ii) Preparation by a dehydrating reaction:

A 2H-pyridazin-3-one derivative (1b) can be obtained by reacting glyoxalic acid—which has been formed by causing sodium periodate to act on tartaric acid under acidic conditions—with the 2-arylacetophenone derivative (2) under basic conditions, reacting hydrazine hydrate with the resultant 2-hydroxy-4-oxobutanoic acid derivative (4) in a lower alcohol as a solvent to convert it into a 4,5-dihydro-4-hydroxy-2H-pyridazin-3-one derivative (5), and then subjecting the derivative (5) to a dehydrating reaction in a solvent while using para-toluenesulfonic acid hydrate as a catalyst.

In the reaction between the compound (2) and glyoxalic acid, commercially-available glyoxalic acid hydrate can also be used in place of glyoxalic acid formed by causing sodium periodate to act on tartaric acid. As an acid usable upon formation of glyoxalic acid, an inorganic acid such as sulfuric acid, hydrochloric acid or phosphoric acid can be mentioned. As a base usable in the reaction between the compound (2) and glyoxalic acid, an inorganic base such as caustic soda or caustic potash or an organic base such as benzyltrimethylammonium hydroxide (Triton B) can be mentioned. In these reactions, the synthesis step of glyoxalic acid is brought to completion generally at −15 to 30C in 20 to 180 minutes, preferably around 0 to 25° C. in 30 to 60 minutes. The reaction with the compound (2) is conducted preferably at 0 to 120° C., and is brought to completion by reacting them, preferably at room temperature for 10 to 25 hours and then at 70° C. for 0.5 to 2 hours. As the solvent, a lower alcohol such as ethanol, methanol, n-propanol or iso-propanol, tetrahydrofuran, 1,4-dioxane or the like can be used. Concerning the reaction between the compound (4) and hydrazine hydrate, anhydrous hydrazine can also be used in place of hydrazine hydrate. The reaction is brought to completion at 50 to 150° C. in 5 to 30 hours, preferably at 80 to 100° C. in 10 to 20 hours. As the solvent, a lower alcohol such as ethanol, methanol, n-propanol or isopropanol, tetrahydrofuran, 1,4-dioxane or the like can be used. In the dehydrating reaction of the compound (5), para-toluenesulfonic acid hydrate or the like can be used as a catalyst. As the solvent, toluene, benzene or the like can be used. The reaction is brought to completion at 50 to 150° C. in 3 to 50 hours, preferably at 80 to 130° C. in 5 to 30 hours.
(4) Preparation of 2H-pyridazin-3-one derivatives (1c: in the formula (1), X is an oxygen atom, and a double bond is formed between the 4-position and the 5-position.):
(i) Preparation of the compound (1c) from the compound (1b):
(a) Preparation by a reaction between (1b) and a halide or reactive ester: 2-Substituted 2H-pyridazin-3-one derivatives of a certain type (1c) can each be obtained by reacting a compound, which is represented by the following formula:

wherein $R^3$ and A have the same meanings as defined above and Y represents a halogen atom or an OH group already converted into a reactive ester group, with the compound (1b) in the presence of a base in a solvent.

As a base usable in this reaction, an inorganic base such as potassium carbonate or sodium carbonate or an organic base such as a metal alkoxide can be mentioned. As the solvent, N,N-dimethylformamide, dimethyl sulfoxide, acetone, methyl ethyl ketone or the like can be used. The reaction is brought to completion at 20 to 150° C. in 1 to 20 hours, preferably at 50 to 130° C. in 2 to 10 hours.

Each compound (1c) in which the 2-substituent is a piperidylalkyl group can be prepared by protecting the nitrogen atom of the piperidyl alkanol as the starting material, converting the hydroxyl group into a reactive ester group, reacting the compound (1b) with the resultant compound, and then conducting deprotection. Further, its N-lower alkylation makes it possible to prepare an N-(lower alkyl)piperidylalkyl derivative.

As a protecting group for the nitrogen atom of the piperidyl alkanol, a tert-butoxycarbonyl group, a benzyloxycarbonyl group, a dimethylphosphinothioyl group or the like is preferred. The compound protected by such a group can be obtained by reacting di-tert-butyl carbonate, benzyloxycarbonyl chloride or the like with the piperidyl alkanol in the presence of a base such as triethylamine or 4-dimethylaminopyridiene. As a solvent, tetrahydrofuran, diethyl ether, ethyl acetate, methylene chloride, chloroform, N,N-dimethylformamide, dimethyl sulfoxide, ethanol, iso-propanol or the like can be used. The reaction is brought to completion at −15 to 50° C. in 5 to 50 hours, preferably at −0 to 20° C. in 1 to 30 hours.

As the reactive ester group of the hydroxyl group, a tosyloxy group, a mesyloxy group, a benzenesulfonyloxy group or the like is preferred. A compound which contains such a group can be obtained by reacting para-toluenesulfonyl chloride, methanesulfonyl chloride, methanesulfonic anhydride, benzenesulfonyl chloride or the like with the N-protected piperidyl alkanol in the presence of a base such as pyridine, triethylamine or collidine. As a solvent, pyridine, tetrahydrofuran, diethyl ether, ethyl acetate, methylene chloride, chloroform, N,N-dimethylformamide, dimethyl sulfoxide or the like can be used. The reaction is brought to completion at −15 to 50° C. in 1 to 50 hours, preferably at −5 to 30° C. in 1 to 10 hours.

The reaction between the compound (1b) and the reactive ester derivative of the N-protected piperidyl alkanol can be conducted in the presence of a base in a solvent. As a base usable here, an inorganic base such as potassium carbonate or sodium carbonate or an organic base such as a metal alkoxide can be mentioned. As a solvent, N,N-dimethylformamide, dimethyl sulfoxide, acetone, methyl ethyl ketone or the like can be used. The reaction is brought to completion at 20 to 150° C. in 1 to 30 hours, preferably at 50 to 130° C. in 2 to 10 hours.

The deprotection of the protecting group on the nitrogen atom of the piperidyl group can be effected by heating the N-protected piperidyl alkanol in the presence of an acid catalyst in a solvent. As an acid usable here, hydrochloric acid, sulfuric acid, acetic acid or the like can be mentioned. Such an acid may be in a form diluted with water. Preferred is 2 to 10 N hydrochloric acid, with 4 to 8 N hydrochloric acid being particularly preferred. As the solvent, tetrahydrofuran, methanol, ethanol, isopropanol, N,N-dimethylformamide or the like can be used. The reaction is brought to completion at 40 to 150° C. in 0.5 to 10 hours, preferably at 50 to 130° C. in 2 to 5 hours.

The N-lower alkylation of the thus-deprotected piperidylalkyl derivative can be conducted by reacting a lower alkyl sulfate, a lower alkyl halide or the like in the presence of a base in a solvent. As a base usable here, sodium hydrogencarbonate, potassium carbonate or the like can be mentioned. As the solvent, acetone, dimethyl sulfoxide, N,N-dimethylformamide, tetrahydrofuran, a mixed solvent thereof or the like is preferred. The reaction is brought to completion at 20 to 150° C. in 0.5 to 10 hours, preferably at 50 to 130° C. in 1 to 5 hours.

(b) Preparation via a 2-hydroxyalkyl derivative:
A compound (1c) the 2-substituent of which is a piperidinoalkyl, piperazinoalkyl or morpholinoalkyl group can be prepared by converting the hydroxyl group of the 2-hydroxyalkyl derivative, which has been obtained by reacting an alkylene chlorohydrin or alkylene carbonate with the compound (1b), into a reactive ester group and then reacting a corresponding amine.

The synthesis of the 2-hydroxyalkyl derivative can be conducted by reacting the compound (1b) with an alkylene chlorohydrin in the presence of a base, for example, in a known manner [Eur. J. Med. Chem. Chim. Ther., 14(1), 53–60, 1979] or by heating the compound (1b) and the alkylene carbonate in the presence or absence of a quaternary ammonium salt as a catalyst in a solvent. As a quaternary ammonium salt usable here, tetraethylammonium iodide, tetraethylammonium bromide, tetra(n-butyl) ammonium iodide, tetra(n-butyl)ammonium bromide or the like can be mentioned. As the solvent, N,N-dimethylformamide, dimethyl sulfoxide, N-methylpyrrolidone or the like can be mentioned. The reaction is brought to completion at 80 to 180° C. in 0.5 to 10 hours, preferably at 120 to 160° C. in 1 to 5 hours.

As the reactive ester group of the hydroxyl group, a tosyloxy group, a mesyloxy group, a benzenesulfonyloxy group or the like is preferred. A compound having such a group can be obtained by reacting paratoluenesulfonyl chloride, methanesulfonyl chloride, methanesulfonic anhydride, benzenesulfonyl chloride or the like with the hydroxylalkyl derivative in the presence of a base such as pyridine, triethylamine or collidine. As a solvent, pyridine, terahydrofuran, diethyl ether, ethyl acetate, methylene chloride, chloroform, N,N-dimethylformamide, dimethylsulfoxide or the like can be used. The reaction is brought to completion at −15 to 50° C. in 1 to 50 hours, preferably at −5 to 30° C. in 1 to 10 hours.

The reaction between the reactive ester derivative and the amine can be conducted by heating the reactive ester derivative in the presence of an excess amount of the amine in a solvent or in a solventless manner or reacting the amine in the presence of an organic amine such as pyridine, triethylamine, 1,8-diazabicyclo[5.4.0]undec-7-ene (DBU) or the like or an inorganic base such as potassium carbonate or sodium carbonate. As the solvent, dimethyl sulfoxide, pyridine, chloroform, methylene chloride, toluene, benzene or the like can be used besides N,N-dimethylformamide. The reaction is brought to completion at 0 to 150° C. in 1 to 10 hours, preferably at 50 to 130° C. in 1 to 5 hours.

(c) Preparation via a 2-carboxyalkyl derivative:

A compound (1c) the 2-substituent of which is an aminocarbonylalkyl group can be prepared by reacting a haloalkyl carboxylate with the compound (1b), hydrolyzing the ester group of the resultant 2-alkyl carboxylate ester derivative, converting it into a reactive acyl derivative, and then reacting it with a corresponding amine or condensing the carboxylic acid derivative and a corresponding amine with a condensing agent such as 1,3-dicyclohexylcarbodiimide (DCC).

As a base usable in the reaction between the compound (1b) and the haloalkyl carboxylate, an inorganic base such as potassium carbonate or sodium carbonate or an organic base such as Triton B can be mentioned. As a solvent, N,N-dimethylformamide, dimethyl sulfoxide, acetone, methyl ethyl ketone or the like can be used. The reaction is brought to completion at 20 to 150° C. in 1 to 30 hours, preferably at 50 to 120° C. in 2 to 20 hours.

The hydrolyzing reaction of the ester group can be conducted by treating the ester derivative in the presence of a base such as caustic soda or caustic potash in a conventional manner.

As the reactive derivative of the carboxylic acid, an acid halide, a mixed acid anhydride or the like can be mentioned. The acid halide can be prepared with oxalyl chloride, thionyl chloride, thionyl bromide or the like, while the mixed acid anhydride can be synthesized with acetic anhydride, pivalic anhydride, methanesulfonic anhydride, para-toluenesulfonyl chloride or the like.

The reaction between these reactive ester derivative and amine can be conducted by reacting the reactive ester derivative with an excess amount of the amine in a solvent or in a solventless manner or by reacting the amine in the presence of an organic amine such as pyridine, triethylamine or DBU or an inorganic base such as potassium carbonate or sodium carbonate. As the solvent, tetrahydrofuran, N,N-dimethylformamide, dimethyl sulfoxide, pyridine, chloroform, methylene chloride, toluene, benzene or the like can be used. The reaction is brought to completion at 0 to 150° C. in 1 to 10 hours, preferably at 50 to 130° C. in 1 to 5 hours.

(d) Preparation by other processes:

Among 2-substituted derivatives (1c), each derivative in which $R^3$ is an aminophenyl group can be obtained by reducing the nitro group of a compound in which $R^3$ is a nitrophenyl group, and its N-lower alkylation makes it possible to prepare an N-(lower alkyl)aminophenyl compound.

The reduction of the nitro group can be effected by conducting hydrogenation in an inert solvent such as ethyl acetate or ethanol while using palladium on charcoal or Raney nickel as a catalyst.

The thus-reduced product can be N-lower alkylated by reacting it with a lower alkyl sulfate, a lower alkyl halide or the like in the presence of a base in a solvent. The resulting N-monoalkyl and dialkyl derivatives can be isolated, respectively, from their mixture.

As the base employed in the N-lower alkylating reaction, sodium hydrogencarbonate, potassium carbonate, pyridine, triethylamine or the like can be mentioned. As the solvent, acetone, dimethyl sulfoxide, N,N-dimethylformamide or tetrahydrofuran, a mixed solvent of two or more of these solvents, or the like is preferred. The reaction is brought to completion at 20 to 150° C. in 0.5 to 10 hours, preferably at 50 to 130° C. in 1 to 5 hours.

(ii) Preparation of the compound (1c) from the compound (1d):

Using the compound (1d) as a starting material, the compound (1c) can be prepared in a similar manner as in the preparation of the compound (1b) from the compound (1a).

(iii) Preparation of compounds (1c) in each of which $R^1$ or $R^2$ is a lower alkylsulfinylphenyl group:

Among the compounds (1c), each derivative in which $R^1$ or $R^2$ is a lower alkylsulfinylphenyl group can be prepared by selectively oxidizing a derivative (1c) in which $R^1$ or $R^2$ is a lower alkylthiophenyl group.

The selective oxidizing reaction can be conducted using metha-chloroperbenzoic acid, hydrogen peroxide solution or the like as an oxidizing agent. The reaction is brought to completion at −30 to 30° C. in 10 minutes to 10 hours, preferably at −10 to 10° C. in 30 minutes to 1 hour. As a solvent, methylene chloride, chloroform or the like can be used.

(iv) Preparation of compounds (1c) in each of which $R^1$ or $R^2$ is a lower alkylsulfonylphenyl group:

Among the compounds (1c), each derivative in which $R^1$ or $R^2$ is a lower alkylsulfonylphenyl group can be prepared by oxidizing a derivative (1c) in which $R^1$ or $R^2$ is a lower alkylthiophenyl group.

The oxidizing reaction can be conducted using osmium tetraoxide-sodium periodate, metha-chloroperbenzoic acid or the like as an oxidizing agent. The reaction is brought to completion at −30 to 50° C. in 1 to 24 hours, preferably at 0 to 20° C. in 5 to 10 hours. As a solvent, acetone-water-chloroform or the like can be used.

(5) Preparation of 2H-pyridazin-3-thione derivatives (1e: in the formula (1), X is a sulfur atom, and a double bond is formed between the 4-position and the 5-position.):

Each 2H-pyridazine-3-thione derivative (1e) can be obtained by thioketonizing its corresponding 2H-pyridazin-3-one derivative with Lawesson's reagent [2,4-bis(4-methoxyphenyl)-1,3-dithia-2,4-diphosphetane-2,4-disulfide) in a solvent.

It is preferred to use Lawesson's reagent in 0.5 to 3 equivalents, notably 1 to 1.5 equivalents relative to the 2H-pyridazin-3-one derivative. The reaction is brought to completion at 30 to 150° C. in 1 to 10 hours, preferably at 50 to 100° C. in 2 to 8 hours. As a usable solvent, toluene, xylene or the like can be mentioned.

The intermediates and target compounds obtained in the above-described individual reactions can be separated and purified by purification methods commonly employed in organic synthesis chemistry, for example, by subjecting them to filtration, extraction, washing, drying, concentration, recrystallization, various chromatographic treatment, and the like. The intermediates may be provided for the next reactions without purifying them specifically. Further, they may also be obtained as solvates of solvents such as reaction solvents or recrystallization solvents, especially as hydrates.

The pyridazine derivatives (1) and their salts according to the present invention, which are available as described above, have excellent inhibitory activity against interleukin-1β production, and are useful for the prevention and treatment of diseases caused by stimulation of interleukin-1β production, for example, immune system diseases, inflammatory diseases, ischemic diseases, osteoporosis, ichorrhemia and the like, especially as medicines such as preventives and therapeutics for rheumatism, immune deficiency syndrome, arthritis, inflammatory colitis, ischemic heart diseases, ischemic encephalopathy, ischemic nephritis, ischemic hepatitis, insulin-dependent diabetes mellitus, arterial sclerosis, Parkinson's disease, Alzheimer's disease, leukemia and the like or as interleukin-1β production inhibitors.

Medicines according to the present invention contain the pyridazine derivatives (1) or their salts as effective ingredients. Their administration routes can include, for example, oral administration by tablets, capsules, granules, powders, syrups or the like and parenteral administration by intravenous injections, intramuscular injections, suppositories, inhalants, transdermal preparations, eye drops, nasal drops or the like. Upon formulation of pharmaceutical compositions of these various unit dosage forms, pharmaceutically acceptable carriers can be mixed with these effective ingredients. As such carriers, excipients, binders, extenders, disintegrators, surfactants, lubricants, dispersants, buffers, preservatives, corrigents, perfumes, coating agents, vehicles, diluents and the like can be used by combining them as desired.

The dosage of each medicine according to the present invention varies depending on the age, body weight, conditions, administration form, administration frequency and the like. In general, however, it is preferred to orally or parenterally administer to an adult the effective ingredient in an amount of about 0.01 to 1,000 mg, preferably 0.1 to 100 mg per day at once or in several portions.

EXAMPLES

The present invention will next be described in further detail by the following Examples. It should however be borne in mind that the present invention is not limited to these Examples.

Preparation Example 1

(1) Preparation of 3,4-bis(4-methoxyphenyl)-2-hydroxy-4-oxobutanoic acid:

To a solution of sodium periodate (11.1 g, 52.0 mmol) in water (65 ml), concentrated sulfuric acid (1.12 ml) was added dropwise little by little under ice-water cooling and stirring. Subsequent to the dropwise addition, the temperature of the resulting mixture was allowed to rise to room temperature, followed by the addition of a solution of tartaric acid (7.81 g, 52.0 mmol) in water (18 ml). The mixture was stirred for 50 minutes. To the reaction mixture, an aqueous solution of sodium hydroxide and a suspension of 2-(4-methoxyphenyl)-4l-methoxyacetophenone (13.32 g, 52.0 mmol) in ethanol (160 ml) were added. The mixture was stirred at 40° C. for 5 hours and then at room temperature for 17 hours, and a reaction was then conducted at 70° C. for 1 hour. Subsequent to cooling, the ethanol was distilled off. The liquid residue was washed with ethyl acetate, acidified with hydrochloric acid, and then extracted with ethyl acetate. The organic layer was washed with a saturated aqueous solution of sodium chloride (brine) and then dried over anhydrous sodium sulfate. The solvent was distilled off, whereby the title compound (16.11 g, 93.8%) was obtained as a brown oil.

(2) Preparation of 5,6-bis(4-methoxyphenyl)-4,5-dihydro-4-hydroxy-2H-pyridazin-3-one:

Hydrazine hydrate (2.4 ml, 49.4 mmol) was added to a solution of 3,4-bis(4-methoxyphenyl)-2-hydroxy-4-oxobutanoic acid (16.11 g, 48.8 mmol) in ethanol (240 ml), followed by heating under reflux for 15 hours at a bath temperature of 100° C. The ethanol was distilled off, whereby the title compound (15.82 g, 99.4%) was obtained as a crude brown oil.

$^1$H-NMR (CDCl$_3$) δ: 3.75(3H,s), 3.78(3H,s), 4.02(1H, brs), 4.25(1H,d), 4.44(1H,d,J=3.91 Hz), 6.81(2H,d,J=9.04 Hz), 6.82(2H,d,J=8.79 Hz), 7.10(2H,d,J=8.54 Hz), 7.58(2H, d,J=9.04 Hz), 9.03(1H,s).

(3) Preparation of 5,6-bis(4-methoxyphenyl)-2H-pyridazin-3-one:

To a solution of 5,6-bis(4-methoxyphenyl)-4,5-dihydro-4-hydroxy-2H-pyridazin-3-one (15.82 g, 48.5 mmol) in benzene (300 ml), para-toluenesulfonic acid monohydrate (1.82 g, 9.6 mmol) was added. A Dean-Stark apparatus was fitted, followed by heating under reflux for 5 hours. Para-toluenesulfonic acid monohydrate (0.50 g) was added, followed by heating under reflux for 18 hours. The benzene was distilled off, and the residue was extracted with ethyl acetate (500 ml). After the organic layer was washed with a saturated aqueous solution of sodium hydrogencarbonate, it was washed with a brine and then dried over anhydrous sodium sulfate. The water layers were combined and then extracted with chloroform (200 ml×3). The organic layer was washed with a brine and then dried over anhydrous sodium sulfate. From the ethyl acetate extract and the chloroform extract, the solvents were distilled off. The residue was separated and purified by chromatography on a silica gel column [silica gel: 50 g, chloroform/methanol (50/1)]. An eluate was concentrated to dryness under reduced pressure, and resulting crystals were heated in ethanol. After the ethanol solution was cool, diethyl ether was added and the thus-obtained solution was left over at room temperature. A precipitate was collected by filtration and then dried at 60° C. under reduced pressure, whereby the title compound (7.84 g, 52.4%) was obtained as pale orange crystals.

Colorless prisms (ethyl acetate-hexane) Melting point: 240.5–242.5° C. $^1$H-NMR (CDCl$_3$) δ: 3.79(3H,s), 3.81(3H, s), 6.78(2H,d,J=9.03 Hz), 6.82(2H,d,J=9.03 Hz), 6.93(1H,s), 7.06(2H,d,J=9.03 Hz), 7.13(2H,d,J=9.04 Hz), 11.42(1H,s). IR (KBr) cm$^{-1}$: 1665,1607,1510,1301,1256,1027,838.

Preparation Example 2

Preparation of methyl 4-(4-methoxyphenyl)-4-oxo-3-(4-pyridyl)butanoate

Under an argon, 2-(4-pyridyl)-4'-methoxyacetophenone (J. Am. Chem. Soc., 112, 2163–3168, 1990: Dimitrios Stefanidis and John W. Bunting; 9.6 g, 42.3 mmol) was suspended in tetrahydrofuran (200 ml), and under ice cooling, lithium diisopropylamide (2.0 M solution; 25 ml, 50.0 mmol) was added. At the same temperature, the mixture was stirred for 30 minutes. Methyl bromoacetate (6.0 ml, 63.4 mmol) was then added dropwise, and the mixture was stirred under ice cooling for 1 hour and then at room temperature for 2 hours. The reaction mixture was diluted with toluene. The mixture was washed successively with 2 N hydrochloric acid, water and a brine, and was then dried over anhydrous sodium sulfate. The solvent was distilled off and the residue was separated and purified by chromatography on a silica gel column [silica gel: 100 g, hexane/ethyl acetate (1/2)], whereby the title compound (10.63 g, 84.1%) was obtained as a brown oil.

$^1$H-NMR (CDCl$_3$) δ: 2.71(1H,dd,J=5.37,16.84 Hz), 3.35 (1H,dd,J=9.28,16.84 Hz), 3.65(3H,s), 3.85(3H,s), 5.04(1H, dd,J=5.37,9.28 Hz), 6.88(2H,d,J=9.03 Hz), 7.23(2H,d,J= 6.10 Hz), 7.93(2H,d,J=9.03 Hz), 8.52(2H,d,J=6.10 Hz). IR (film) cm$^{-1}$: 1763,1674,1600,1512,1418,1263,1170.

Preparation Example 3
(1) Preparation of 2-(4-chlorophenyl)-4'-(methylthio) acetophenone:

A mixture consisting of para-chlorophenyl acetic acid (17.06 g, 0.1 mol), thioanisole (24.84 g, 0.2 mol) and polyphosphoric acid (67.59 g, 0.2 mol) was heated at 100° C. for 7 hours. Water was added to the solidified reaction product, and a white solid insoluble in water was collected by filtration and then washed with n-hexane. The solid was recrystallized from a mixed solvent of ethanol and ethyl acetate, whereby the title compound (21.24 g, 76.7%) was obtained. Further, the mother liquor was separated and purified by chromatography on a silica gel column (ethyl acetate). Recrystallization was then conducted from ethyl acetate, whereby the title compound (2.86 g, 10.4%) was obtained.

Colorless prisms (ethyl acetate) Melting point: 161.1–162.1° C. $^1$H-NMR (CDCl$_3$) δ: 2.51(3H,s), 4.21(2H, s), 7.19(2H,d,J=8.55 Hz), 7.26(2H,d,J=8.91 Hz), 7.29(2H, d,J=8.55 Hz), 7.89(2H,d,J=8.91 Hz).
(2) Preparation of ethyl 3-(4-chlorophenyl)-4-[4-(methylthio)phenyl]-4-oxobutanoate:

A suspension of 2-(4-chlorophenyl)-4'-(methylthio) acetophenone (34.98 g, 126.4 mmol) in tetrahydrofuran (350 ml) was ice-cooled, followed by the addition of potassium tert-butoxide (17.01 g, 151.6 mmol) under a nitrogen gas atmosphere. At the same temperature, the mixture was stirred for 10 minutes. After ethyl bromoacetate (25.33 g, 151.7 mmol) was added dropwise over 10 minutes, the mixture was stirred at the same temperature for 30 minutes. The reaction mixture was poured into toluene (350 ml), to which ice water (350 ml) was added, followed by extraction. The organic layer was collected. Further, the water layer was extracted with toluene (100 ml). The thus-obtained organic layers were combined, washed with a brine (300 ml), and then dried over anhydrous sodium sulfate. The solvent was distilled off, whereby the title compound (45.54 g, quantitative) was obtained as a yellow oil.

$^1$H-NMR (CDCl$_3$) δ: 1.19(3H,t,J=7. 1Hz), 2.47(3H,s), 2.70(1H,dd,J=5.4,16.9 Hz), 3.31(1H,dd,J=9.4,16.9 Hz), 4.09(2H,q,J=7.1 Hz), 5.01(1H,dd,J=5.4,9.4 Hz), 7.16–7.28 (6H,m), 7.86(2H,d,J=8.7 Hz). IR (film) cm$^{-1}$: 1738,1733, 1683,1590,1252,1233,1178, 1094,820.

Preparation Example 4

Preparation of methyl 3-(4-chlorophenyl)-4-[4-(methylthio)phenyl]-4-oxobutanoate Using 2-(4-chlorophenyl)-4'-(methylthio)acetophenone as a starting material, the procedures of Preparation Example 2 were repeated likewise, whereby the title compound was obtained as a pale yellow oil in a yield of 95.8%.

$^1$H-NMR (CDCl$_3$) δ: 2.56(3H,s), 2.61(1H,dd,J=5.37, 16.97 Hz), 3.24(1H,dd,J=9.28,16.97 Hz), 3.55(3H,s), 4.94 (1H,dd,J=5.37,9.28 Hz), 7.10(2H,d,J=8.55 Hz), 7.12–7.20 (4H,m), 7.77(2H,d,J=8.84 Hz). IR (film) cm$^{-1}$: 1736,1675, 1590,1490,1437,1403,1252, 1234,1173,1094.

Preparation Example 5

Preparation of methyl 3-(4-fluorophenyl)-4-[4-(methylthio)phenyl]-4-oxobutanoate Using 2-(4-fluorophenyl)-4'-(methylthio)acetophenone as a starting material, the procedures of Preparation Example 2 were repeated likewise, whereby the title compound was obtained as a pale yellow oil in a yield of 86.5%.

$^1$H-NMR (CDCl$_3$) δ: 2.45(3H,s), 2.70(1H,dd,J=5.31, 16.91 Hz), 3.32(1H,dd,J=9.40,16.91 Hz), 3.63(3H,s), 5.04 (1H,dd,J=5.11,9.40 Hz), 6.96(2H,t,J=8.67 Hz), 7.18(2H,d, J=8.79 Hz), 7.25(2H,dd,J=5.25,8.67 Hz), 7.86(2H,d,J=8.79 Hz).

Preparation Example 6
(1) Preparation of 2-phenyl-4'-(methylthio)acetophenone

After aluminum chloride (5.61 g, 42.1 mmol) was added to dichloroethane (25 ml), phenylacetyl chloride (5.00 g, 32.3 mmol) and thioanisole (6.03 g, 48.5 mmol) were added under ice cooling. The resulting mixture was stirred at room temperature for 20 hours. Ice water was added to the reaction mixture, followed by extraction with chloroform. The extract was washed with water and then dried over anhydrous sodium sulfate. The solvent was distilled off, and the residue was crystallized with hexane. The crystals were recrystallized from ethanol, whereby the title compound (5.77 g, 73.6%) was obtained as colorless prisms. Further, the recrystallization mother liquid was separated and purified by chromatography on a silica gel column [hexane/ethyl acetate (20/1)], whereby the title compound (0.57%, 7.3%) was obtained.

$^1$H-NMR (CDCl$_3$) δ: 2.50(3H,s), 4.23(2H,s), 7.20–7.36 (7H,m), 7.92(2H,d,J=8.8 Hz). IR (KBr) cm$^{-1}$: 1682,1587, 1334,1221,1090,992,815,706.
(2) Preparation of methyl 4-[4-(methylthio)phenyl]-4-oxo-3-phenylbutanoate Using 2-phenyl-4'-(methylthio)acetophenone as a starting material, the procedures of Preparation Example 2 were repeated likewise, whereby the title compound was obtained in a yield of 86.5%.

Colorless prisms (ethyl acetate-hexane). Melting point: 82.4–83.0° C. $^1$H-NMR (CDCl$_3$) δ: 2.46(3H,s), 2.70(1H,dd, J=4.95,16.91 Hz), 3.36(1H,dd,J=9.65,16.91 Hz), 3.65(3H, s), 5.03(1H,dd,J=4.45,9.65 Hz), 7.18(2H,d,J=8.55 Hz), 7.20–7.30(5H,m), 7.88(2H,d,J=8.55 Hz). IR (KBr) cm$^{-1}$: 1740,1680,1590,1404,1235,1200,1175,1094.

Preparation Example 7

Preparation of 3'-fluoro-4'-methoxy-2-(4-methoxyphenyl)acetophenone

Thionyl chloride (3.57 g) was added to a solution of 4-methoxyphenylacetic acid (3.32 g, 19.98 mmol) in benzene (30 ml). After the mixture was heated under reflux for 3 hours, the solvent was distilled off. To the residue, methylene chloride (50 ml) and 2-fluoroanisole (2.10 g) were added. Under ice cooling, aluminum chloride (13.32 g) was added, followed by stirring for 30 minutes. The mixture was then stirred at room temperature for 2 hours. The reaction mixture was added to ice water, followed by extraction with methylene chloride. The extract was dried over anhydrous sodium sulfate. The solvent was distilled off under reduced pressure. The residue so obtained was separated and purified by chromatography on a silica gel column and was then crystallized form ethyl acetate-hexane, whereby the title compound (2.27 g, 49.6%) was obtained as colorless prisms.

Melting point: 141.7–142.7° C. Mass (m/Z): 274 (M$^+$). $^1$H-NMR (CDCl$_3$) δ: 3.78(3H,s), 3.94(3H,s), 4.15(2H,s), 6.86(2H,d,J=8.7 Hz), 6.98(1H,dd,J=8.5 Hz,J=8.5 Hz), 7.17 (2H,d,J=8.7 Hz), 7.73(1H,dd,J=12.0 Hz,J=2.2 Hz), 7.79(1H, ddd,J=8.5 Hz,J=2.2 Hz,J=1.0 Hz). IR (KBr) cm$^{-1}$: 1681, 1613,1516,1436,1286,1254,1223,1177, 1132,1034,1014, 889,809,787.

Preparation Example 8

Preparation of ethyl 3-(3-fluoro-4-methoxyphenyl)-4-(4-methoxyphenyl)-4-oxobutanoate (1) Preparation of 2-(3-fluoro-4-methoxyphenyl)-4'-methoxyacetophenone:

Using 3-fluoro-4-methoxyphenylacetic acid and anisole as starting materials, the procedures of Preparation Example 7 were repeated likewise, whereby the title compound was obtained in a yield of 57.0%.

Colorless needles (ethyl acetate-hexane). Melting point: 117.0–117.7° C. Mass (m/Z): 274 (M$^+$). $^1$H-NMR (CDCl$_3$) δ: 3.82(3H,s), 3.83(3H,s), 4.13(2H,s), 6.85–7.01(5H,m), 7.96(2H,d,J=9.0 Hz). IR (KBr) cm$^{-1}$: 1682,1600,1524,1278, 1263,1214,1178,1127, 1025.

(2) Preparation of ethyl 3-(3-fluoro-4-methoxyphenyl)-4-(4-methoxyphenyl)-4-oxobutanoate:

Using 2-(3-fluoro-4-methoxyphenyl)-4'-methoxyacetophenone as a starting material, the procedures of Preparation Example 2 were repeated likewise, whereby the title compound was obtained in a yield of 85.5%.

Yellow oil. $^1$H-NMR (CDCl$_3$) δ: 1.14(3H,t,J=7.1 Hz), 2.71(1H,dd,J=16.3 Hz,J=5.1 Hz), 3.33(1H,dd,J=16.3 Hz,J= 9.5 Hz), 3.695(3H,s), 3.703(3H,s), 4.06(2H,q,J=7.1 Hz), 5.07(1H,dd,J=9.5 Hz,J=5.1 Hz), 6.77–6.91(3H,m), 7.03(1H, d,J=8.3 Hz), 7.10(1H,dd,J=12.0 Hz,J=2.0 Hz), 7.99(2H,d,J= 8.8 Hz).

Preparation Example 9

Preparation of ethyl 3,4-bis(3-fluoro-4-methoxyphenyl)-4-oxobutanoate (1) Preparation of 3'-fluoro-2-(3-fluoro-4-methoxyphenyl)-4'-methoxyacetophenone Using 3-fluoro-4-methoxyphenylacetic acid and 2-fluoroanisole as starting materials, the procedures of Preparation Example 7 were repeated likewise, whereby the title compound was obtained in a yield of 77.5%.

Colorless needles (ethyl acetate-hexane). Melting point: 150.6–151.7° C. Mass (m/Z): 292 (M$^+$). $^1$H-NMR (CDCl$_3$) δ: 3.87(3H,s), 3.95(3H,s), 4.14(2H,s), 6.88–7.03(4H,m), 7.73(1H,dd,J=12.0 Hz,J=2.2 Hz), 7.78(1H,ddd,J=8.5 Hz,J= 2.2 Hz,J=1.0 Hz). IR (KBr) cm$^{-1}$: 1677,1613,1520,1436, 1282,1265,1224,1180, 1124.

(2) Preparation of ethyl 3,4-bis(3-fluoro-4-methoxyphenyl)-4-oxobutanoate:

Using 3'-fluoro-2-(3-fluoro-4-methoxyphenyl)-4'-methoxyacetophenone as a starting material, the procedures of Preparation Example 2 were repeated likewise, whereby the title compound was obtained in a yield of 62.3%.

Yellow oil. Mass (m/Z): 378 (M$^+$). $^1$H-NMR (CDCl$_3$) δ: 1.18(3H,t,J=7.1 Hz), 2.69(1H,dd,J=17.0 Hz,J=5.1 Hz) 3.30 (1H,dd,J=17,0 Hz,J=9.5 Hz), 3.81(3H,s), 3.89(3H,s), 4.09 (2H,q,J=7.1 Hz), 4.94(1H,dd,J=9.5 Hz,J=5.1 Hz), 6.88(1H, dd,J=8.5 Hz,J=8.5 Hz), 6.93(1H,dd,J=8.5 Hz,J=8.5 Hz), 6.96–7.06(2H,m), 7.70(1H,dd,J=12.0 Hz,J=2.0 Hz), 7.77 (1H,d,J=8.5 Hz). HRMS: Calcd. for C$_{20}$H$_{20}$F$_2$O$_5$: 378.12785. Found: 378.12759.

Example 1

Preparation of 5-(4-chlorophenyl)-6-[4-(methylthio)phenyl]-4,5-dihydro-2H-pyridazin-3-one Hydrazine hydrate (10.56 g, 210.9 mmol) was added to a solution of ethyl 3-(4-chlorophenyl)-4-[4-(methylthio)phenyl]-4-oxobutanoate (42.54 g, 117.2 mmol) in ethanol (85 ml), followed by heating under reflux for 15 hours at a bath temperature of 100° C. A 4 N aqueous solution of sodium hydroxide (40 ml) was added to the reaction mixture. After the mixture was ice-cooled, precipitated crystals were collected by filtration, washed with water (3×100 ml), dried in air, and then dried under reduced pressure (100° C., 2 hours), whereby the title compound (31.49 g, 81.2%) was obtained as pale yellow crystalline powder.

Melting point: 170.5–172.8° C.

Example 2

Preparation of 4,5-dihydro-5-(4-fluorophenyl)-6-(4-(methylthio)phenyl]-2H-pyridazin-3-one Using methyl 3-(4-fluorophenyl)-4-[(4-methylthio)phenyl]-4-oxobutanoate as a starting material, the procedures of Example 1 were repeated likewise, whereby the title compound was obtained in a yield of 33.1%.

$^1$H-NMR (CDCl$_3$) δ: 2.47(3H,s), 2.77(1H,d,J=17.01 Hz), 2.99(1H,dd,J=7.73,17.01 Hz), 4.41(1H,d,J=7.73 Hz), 7.00 (2H,t,J=8.67 Hz), 7.12–7.29(4H,m), 7.59(2H,d,J=8.55 Hz).

Example 3

Preparation of 4,5-dihydro-6-(4-methoxyphenyl)-5-(4-pyridyl)-2H-pyridazin-3-one

Methyl 4-(4-methoxyphenyl)-4-oxo-3-(4-pyridyl)butanoate (10.63 g, 35.6 mmol) was dissolved in ethanol (200 ml), followed by the addition of hydrazine hydrate (1.77 g, 35.26 mmol). The mixture was heated under reflux for 17 hours. The reaction mixture was concentrated under reduced pressure. The residue so obtained was separated and purified by chromatography on a silica gel column [silica gel: 100 g, chloroform/methanol (10/1)] and was then recrystallized from ethanol-hexane, whereby the title compound (5.92 g, 59.3%) was obtained as pale yellow crystalline powder.

Melting point: 100.1–102.3° C. $^1$H-NMR (CDCl$_3$) δ: 2.80(1H,dd,J=1.71,17.09 Hz), 3.04(1H,dd,J=7.81,17.09 Hz), 3.82(3H,s), 4.46(1H,dd,J=1.71,7.81 Hz), 6.89(2H,d,J= 9.03 Hz), 7.15(2H,d,J=6.10 Hz), 7.62(2H,d,J=9.03 Hz), 8.56 (2H,d,J=6.10 Hz), 8.68(1H,brs). IR (KBr) cm$^{-1}$: 1679,1611, 1597,1515,1355,1330,1259,1167.

Example 4

Preparation of 6-(3,4-dimethoxyphenyl)-5-(4-methoxyphenyl)-2H-pyridazin-3-one

Using 2-(4-methoxyphenyl)-3',4'-dimethoxyacetophenone as a starting material, the procedures of Preparation Example 1 were repeated likewise. The reaction product was then recrystallized from ethyl acetate-hexane, whereby the title compound was obtained as pale orange crystals in a yield of 29%. $^1$H-NMR (CDCl$_3$) δ:

3.66(3H,s), 3.81(3H,s), 3.87(3H,s), 6.70(1H,d,J=1.65 Hz), 6.75(1H,d,J=8.24 Hz), 6.79(1H,dd,J=1.65,8.25 Hz), 6.94 (2H,d,J=8.91 Hz), 7.07(2H,d,J=8.90 Hz).

Example 5

Preparation of 6-(4-methoxyphenyl)-5-phenyl-2H-pyridazin-3-one

Using 2-phenyl-41-methoxyacetophenone (J. Med. Chem., 25, 1070–1077, 1982: Martin R. Schneider, Erwin von Angerer, Helmut Schonenberger, Ralf Th Michel, and H. F. Fortmeyer) as a starting material, the procedures of Preparation Example 1 were repeated likewise, whereby the title compound was obtained as colorless crystals in a yield of 56.1%.

$^1$H-NMR (CDCl$_3$) δ: 1.57–1.69(1H,br), 3.78(3H,s), 6.76 (2H,d,J=8.79 Hz), 6.97(1H,s), 7.07–7.18(4H,m), 7.24–7.40 (3H,m).

Example 6

Preparation of 5-(4-chlorophenyl)-6-(4-methoxyphenyl)-2H-pyridazin-3-one

Using 2-(4-chlorophenyl)-4'-methoxyacetophenone as a starting material, the procedures of Preparation Example 1 were repeated likewise, whereby the title compound was obtained as pale brown crystals in a yield of 11%.

$^1$H-NMR (CDCl$_3$) δ: 3.80(3H,s), 6.79(2H,d,J=8.90 Hz), 6.95(1H,s), 7.07(2H,d,J=8.90 Hz), 7.10(2H,d,J=8.91 Hz), 7.29(2H,d,J=8.58 Hz), 11.73(1H,br).

Example 7

Preparation of 5-(4-chlorophenyl)-6-[4-(methylthio)phenyl]-2H-pyridazin-3-one

A solution of 5-(4-chlorophenyl)-4,5-dihydro-6-[4-(methylthio)phenyl]-2H-pyridazin-3-one (31.49 g, 95.2 mmol) in acetic acid (160 ml) was stirred under heating at 70° C. After a solution of bromine (15.21 g, 95.2 mmol) in acetic acid (60 ml) was added dropwise over 20 minutes, the mixture was continuously stirred under heating for 30 minutes. The reaction mixture was cooled with ice water, followed by the successive gradual addition of a 10% aqueous solution of sodium hydrogensulfite (50 ml) and water (1.1 l). A precipitate was collected by filtration, washed with water, and then dried in air, whereby pale yellow crystalline powder (33.88 g) was obtained. The powder was suspended in ethyl acetate (120 ml). The suspension was heated under reflux at 90° C. for 30 minutes, and hexane (120 ml) was then added. The mixture was cooled with ice water. Precipitated crystals were collected by filtration and then dried in air, whereby title compound (29.84 g, 95.3%) was obtained as pale brown crystalline powder.

Colorless needles (chloroform-hexane) Melting point: 201.7–203.7° C. $^1$H-NMR (CDCl$_3$) δ: 2.47(3H,s), 6.95(1H, s), 7.05–7.16(6H,m), 7.27(2H,d,J=7.3 Hz), 11.40(1H,brs). IR (KBr) cm$^{-1}$: 1656,1584,1490,1282,1092.

Example 8

Preparation of 6-(4-methoxyphenyl)-5-(4-pyridyl)-2H-pyridazin-3-one 4,5-Dihydro-6-(4-methoxyphenyl)-5-(4-pyridyl)-2H-pyridazin-3-one (5.4 g, 19.2 mmol) was dissolved in acetic acid (180 ml), followed by the addition of 2,3-dichloro-5,6-dicyano-1,4-benzoquinone (5.0 g, 22.0 mmol). The interior of the reaction system was purged with argon, and the contents were stirred at 70° C. for 18 hours. The reaction mixture was concentrated under reduced pressure. The residue was separated and purified by chromatography on a silica gel column [silica gel: 100 g, chloroform/methanol (10/1)→chloroform/methanol (with 10% (W/W) ammonia) (20/1)], followed by further separation and purification by chromatography on a silica gel column [silica gel: 200 g, chloroform/methanol (with 10% (W/W) ammonia) (20/1)]. The crude crystals were recrystallized from chloroform-ethyl acetate-diethyl ether, whereby the title compound (4.61 g, 86.0%) was obtained as pale yellow crystals.

Melting point: 236.0–267.6° C. $^1$H-NMR (CDCl$_3$) δ: 3.80(3H,s), 6.78(2H,d,J=8.79 Hz), 7.03(1H,s), 7.08(2H,d,J= 6,10 Hz), 7.09(2H,d,J=8.79 Hz), 8.60(2H,d,J=6.10 Hz). IR (KBr) cm$^{-1}$: 3236,1672,1605,1515,1254,1176.

Example 9

Preparation of 5-(4-fluorophenyl)-6-[4-(methylthio)phenyl]-2H-pyridazin-3-one

Using 4,5-dihydro-5-(4-fluorophenyl)-6-[4-(methylthio)phenyl]-2H-pyridazin-3-one as a starting material, the procedures of Example 8 were repeated likewise, whereby the title compound was obtained in a yield of 92.6%.

Pale yellow prisms (ethyl acetate-hexane). Melting point: 197.4–198.2° C. Mass (m/e): 312 (M$^+$). $^1$H-NMR (CDCl$_3$) δ: 2.47(3H,s), 6.96(1H,s), 7.02(2H,t,J=8.59 Hz), 7.07–7.13 (6H,m). IR (KBr) cm$^{-1}$: 3122,1660,1597,1511,1225,1171, 1026,852, 818,759,699.

Example 10

Preparation of 4,5-dihydro-5-phenyl-6-[4-(methylthio)phenyl]-2H-pyridazin-3-one

Using methyl 4-[4-(methylthio)phenyl]-4-oxo-3-phenylbutanoate as a starting material, the procedures of Example 1 were repeated likewise, whereby the title compound was obtained in a yield of 47.5%.

Colorless needles (ethyl acetate-hexane). Melting point: 212.6–213.8° C. $^1$H-NMR (CDCl$_3$) δ: 2.47(3H,s), 2.81(1H, dd,J=1.65,16.97 Hz), 3.01(1H,dd,J=7.88,16.97 Hz), 4.45 (1H,dd,J=1.65,7.88 Hz), 7.14–7.43(7H,m), 7.61(2H,d,J= 8.79 Hz).

Example 11

Preparation of 6-[4-(methylthio)phenyl]-5-phenyl-2H-pyridazin-3-one

Using 4,5-dihydro-6-[4-(methylthio)phenyl]-5-phenyl-2H-pyridazin-3-one as a starting material, the procedures of Example 8 were repeated likewise, whereby the title compound was obtained in a yield of 95.7%.

Colorless needles (ethyl acetate-hexane). Melting point: 185.8–186.1° C. $^1$H-NMR (CDCl$_3$) δ: 2.45(3H,s), 7.04(1H, s), 7.05–7.17(6H,m), 7.27–7.40(3H,m). IR (KBr) cm$^{-1}$: 1656,1588,1574,1491,1020,894,827,774, 755,701.

Example 12

Preparation of 5,6-bis(4-methoxyphenyl)-2-(4-chlorocinnamyl)-2H-pyridazin-3-one

4-Chlorocinnamyl chloride (898 mg, 4.8 mmol) was added to a suspension of 5,6-bis(4-methoxyphenyl)-2H- pyridazin-3-one (802 mg, 2.4 mmol) and potassium carbonate (663 mg, 4.8 mmol) in N,N-dimethylformamide (8 ml), followed by stirring at 70° C. for 6 hours. After water (50 ml) was added to the reaction mixture, the resulting mixture was extracted with ethyl acetate. The organic layer was washed successively with water and a saturated aqueous solution of sodium chloride, and then dried over anhydrous sodium sulfate. The solvent was distilled off. An orange oil (1.73 g) so obtained was separated and purified by chromatography on a silica gel column [silica gel: 40 g, hexane/ethyl acetate (1/1)], whereby pale yellow crystalline powder (1.22 g) was obtained. The powder was recrystallized from chloroform-diethyl ether-hexane, whereby the title compound (1.09 g, 91.3%) was obtained as pale yellow prisms (dried at 70° C. for 3 hours under reduced pressure).

Melting point: 155.0–156.7° C. $^1$H-NMR (CDCl$_3$) δ: 3.78(3H,s), 3.80(3H,s), 5.01(2H,dd,J=1.22,6.59 Hz), 6.45 (1H,dt,J=15.87,6.59 Hz), 6.69(1H,d,J=15.87 Hz), 6.79(2H, d,J=8.79 Hz), 6.81(2H,d,J=8.78 Hz), 6.91(1H,s), 7.04(2H, d,J=8.78 Hz), 7.13(2H,d,J=8.79 Hz), 7.26(2H,d,J=8.54 Hz), 7.33(2H,d,J=8.79 Hz). IR (KBr) cm$^{-1}$: 1665,1609,1513, 1246,965,837,700.

Example 13

Preparation of 5,6-bis(4-methoxyphenyl)-2-benzyl-2H-pyridazin-3-one

Using 5,6-bis(4-methoxyphenyl)-2H-pyridazin-3-one as a starting material, the procedures of Example 12 were repeated likewise, whereby the title compound was obtained in a yield of 74.4%.

Colorless prisms (chloroform-hexane). Melting point: 145.0–145.7° C. $^1$H-NMR (CDCl$_3$) δ: 3.79(3H,s), 3.80(3H, s), 5.41(2H,s), 6.78(2H,d,J=9.04 Hz), 6.80(2H,d,J=8.79 Hz), 6.89(1H,s), 7.02(2H,d,J=8.79 Hz), 7.11(2H,d,J=8.79 Hz), 7.11(2H,d,J=8.78 Hz), 7.27–7.40(3H,m), 7.50–7.60(2H,m). IR (KBr) cm$^{-1}$: 1659,1608,1515,1293,1249,1186,1177, 1029, 841,702.

Example 14

Preparation of 5,6-bis(4-methoxyphenyl)-2-(4-methoxybenzyl)-2H-pyridazin-3-one

Using 5,6-bis(4methoxyphenyl)-2H-pyridazin-3-one as a starting material, the procedures of Example 12 were repeated likewise, whereby the title compound was obtained in a yield of 54.54%.

Colorless prisms (methanol-diethyl ether). Melting point: 171–172° C. $^1$H-NMR (CDCl$_3$) δ: 3.79(9H,s), 5.35(2H,s), 6.78(2H,d,J=8.79 Hz), 6.83(2H,d,J=8.79 Hz), 6.87(1H,s), 6.88(2H,d,J=8.79 Hz), 7.01(2H,d,J=8.79 Hz), 7.11(2H,d,J= 9.04 Hz), 7.69(2H,d,J=8.79 Hz). IR (KBr) cm$^{-1}$: 1664,1609, 1512,1247,1185,1173,1023,951.

Example 15

Preparation of 5,6-bis(4-methoxyphenyl)-2-(3,4-dimethoxybenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 17.4%.

Pale yellow amorphous. Mass (m/e): 458 (M$^+$). $^1$H-NMR (CDCl$_3$) δ: 3.79(6H,s), 3.87(3H,s), 3.90(3H,s), 5.32(2H,s), 6.78(2H,d,J=8.79 Hz), 6.80(2H,d,J=8.79 Hz), 6.85(1H,d,J= 8.30 Hz), 6.88(1H,s), 6.96(2H,d,J=8.79 Hz), 7.10–7.14(1H, m), 7.11(2H,d,J=8.79 Hz), 7.17(1H,d,J=1.95 Hz).

IR (film) cm$^{-1}$: 1660,1609,1515,1250,1028,834.

Example 16

Preparation of 5,6-bis(4-methoxyphenyl)-2-(3,4,5-trimethoxybenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 73.6%.

Pale yellow prisms (chloroform-diethyl ether). Melting point: 138.0–139.0° C. $^1$H-NMR (CDCl$_3$) δ: 3.80(6H,s), 3.84(3H,s), 3.87(3H,s), 5.33(2H,s), 6.78(2H,d,J=8.79 Hz), 6.80(2H,d,J=8.79 Hz), 6.82(2H,s), 6.89(1H,s), 7.02(2H,d,J= 8.79 Hz), 7.11(2H,d,J=8.76 Hz). IR (KBr) cm$^{-1}$: 1658,1607, 1590,1511,1250,1130,1118,840.

Example 17

Preparation of 5,6-bis(4-methoxyphenyl)-2-phenethyl-2H-pyridazin-3-one

Using 5,6-bis(4-methoxyphenyl)-2H-pyridazin-3-one as a starting material, the procedures of Example 12 were repeated likewise, whereby the title compound was obtained in a yield of 80.0%.

Pale yellow needles (chloroform-hexane). Melting point: 139.8–140.4° C. $^1$H-NMR (CDCl$_3$) δ: 3.17–3.23(2H,m), 3.79(3H,s), 3.81(3H,s), 4.46–4.52(2H,m), 6.77(2H,d,J=8.79 Hz), 6.81(2H,d,J=9.03 Hz), 6.90(1H,s), 7.02(2H,d,J=9.03 Hz), 7.03(2H,d,J=9.03 Hz), 7.24–7.33(5H,m). IR (KBr) cm$^{-1}$: 1654,1608,1512,1245,1177,1029,843,743.

Example 18

Preparation of 5,6-bis(4-methoxyphenyl)-2-(3,4-dimethoxyphenethyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 77.0%.

Pale yellow needles (ethyl acetate-hexane). Melting point: 130.9–131.4° C. $^1$H-NMR (CDCl$_3$) δ: 3.12–3.17(2H,m), 3.79(3H,s), 3.81(3H,s), 3.84(3H,s), 3.87(3H,s), 4.44–4.50 (2H,m), 6.76–6.85(7H,m), 6.91(1H,s), 7.02(2H,d,J=9.03 Hz), 7.04(1H,s), 7.05(2H,d,J=9.04 Hz). IR (KBr) cm$^{-1}$: 1655,1608,1516,1266,1242,1028,842.

Example 19

Preparation of 5,6-bis(4-methoxyphenyl)-2-(3-phenylpropyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 81.3%.

Brown amorphous. $^1$H-NMR (CDCl$_3$) δ: 2.18–2.30(2H, m), 2.76(2H,t,J=8.30 Hz), 3.79(3H,s), 3.80(3H,s), 4.31(2H, t,J=8.32 Hz), 6.78(2H,d,J=9.04 Hz), 6.81(2H,d,J=8.79 Hz), 6.86(1H,s), 7.03(2H,d,J=8.79 Hz), 7.12(2H,d,J=9.03 Hz), 7.15–7.30(5H,m). IR (film) cm$^{-1}$: 1652,1608,1515,1295, 1247,1177,1031,833, 750,700.

Example 20

Preparation of 5,6-bis(4-methoxyphenyl)-2-[3-(phenoxy)propyl]-2H-pyridazin-3-one Using 5,6-bis(4-methoxyphenyl)-2H-pyridazin-3-one as a starting material, the procedures of Example 12 were repeated likewise, whereby the title compound was obtained in a yield of 75.5%.

Pale yellow crystalline powder (diethyl ether). Melting point: 110.0–111.0° C. Mass (m/e): 442 (M$^+$). $^1$H-NMR (CDCl$_3$) δ: 2.37–2.42(2H,m), 3.78(3H,s), 3.81(3H,s), 4.12 (2H,t,J=6.35 Hz), 4.47(2H,t,J=7.08 Hz), 6.74(2H,d,J=8.79 Hz), 6.81(2H,d,J=8.79 Hz), 6.88–6.97(4H,m), 7.03(4H,d,J=9.04 Hz), 7.24–7.30(2H,m). IR (KBr) cm$^{-1}$: 1660,1609, 1513,1295,1250,1176,1027,838, 753.

Example 21

Preparation of 5,6-bis(4-methoxyphenyl)-2-cinnamyl-2H-pyridazin-3-one

Using 5,6-bis(4-methoxyphenyl)-2H-pyridazin-3-one as a starting material, the procedures of Example 12 were repeated likewise, whereby the title compound was obtained in a yield of 50.4%.

Yellow amorphous. Mass (m/e): 424 (M$^+$). $^1$H-NMR (CDCl$_3$) δ: 3.79(3H,s), 3.80(3H,s), 5.01(2H,dd,J=0.98,6.59 Hz), 6.48(1H,dt,J=15.87,6.59 Hz), 6.74(1H,d,J=15.87 Hz), 6.78(2H,d,J=9.03 Hz), 6.81(2H,d,J=8.79 Hz), 6.91(1H,s), 7.04(2H,d,J=8.78 Hz), 7.13(2H,d,J=9.03 Hz), 7.20–7.33 (3H,m), 7.37–7.42(2H,m). IR (KBr) cm$^{-1}$: 1660,1609,1511, 1295,1248,1177,1027,950, 833.

Example 22

Preparation of 5,6-bis(4-methoxyphenyl)-2-(4-methoxycinnamyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 16.1%.

Pale yellow oil. Mass (m/e): 454 (M$^+$). $^1$H-NMR (CDCl$_3$) δ: 3.79(3H,s), 3.80(3H,s), 4.98(2H,d,J=6.59 Hz), 6.35(1H, dt,J=15.87,6.59 Hz), 6.70(1H,d,J=15.8 Hz), 6.78(2H,d,J=9.03 Hz), 6.81(2H,d,J=9.03 Hz), 6.84(2H,d,J=9.03 Hz), 6.91 (1H,s), 7.04(2H,d,J=9.04 Hz), 7.13(2H,d,J=8.79 Hz), 7.34 (2H,d,J=8.79 Hz). IR (film) cm$^{-1}$: 1652,1608,1514,1297, 1248,1177,1031,834, 754.

Example 23

Preparation of 5,6-bis(4-methoxyphenyl)-2-[3-(4-methoxyphenyl)propyl]-2H-pyridazin-3-one Using 5,6-bis(4-methoxyphenyl)-2H-pyridazin-3-one as a starting material, the procedures of Example 12 were repeated likewise, whereby the title compound was obtained in a yield of 59.4%.

Pale yellow amorphous. Mass (m/e): 456 (M$^+$). $^1$H-NMR (CDCl$_3$) δ: 2.16–2.27(2H,m), 2.70(2H,t,J=7.32 Hz), 3.77 (3H,s), 3.80(3H,s), 3.81(3H,s), 4.29(2H,t,J=7.32 Hz), 6.79 (2H,d,J=8.79 Hz), 6.81(4H,d,J=8.79 Hz), 6.87(1H,s), 7.03 (2H,d,J=9.03 Hz), 7.12(2H,d,J=8.79 Hz), 7.15(2H,d,J=7.81 Hz). IR (film) cm$^{-1}$: 1661,1609,1514,1297,1247,1179,1034, 833, 754.

Example 24

Preparation of 5,6-bis(4-methoxyphenyl)-2-(4-methylcinnamyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 71.6%.

Pale brown oil. $^1$H-NMR (CDCl$_3$) δ: 2.33(3H,s), 3.79(3H, s), 3.80(3H,s), 5.00(2H,d,J=6.59 Hz), 6.42(1H,dt,J=15.87, 6.60 Hz), 6.72(1H,d,J=15.87 Hz), 6.78(2H,d,J=8.78 Hz), 6.81(2H,d,J=8.79 Hz), 6.91(1H,s), 7.04(2H,d,J=8.78 Hz), 7.11(2H,d,J=7.32 Hz), 7.13(2H,d,J=9.04 Hz), 7.30(2H,d,J= 8.06 Hz). IR (film) cm$^{-1}$: 1652,1610,1514,1296,1251,1180, 1034,834, 756.

Example 25

Preparation of 5,6-bis(4-methoxyphenyl)-2-[3-(4-methylphenyl)propyl]-2H-pyridazin-3-one Using 5,6-bis(4-methoxyphenyl)-2H-pyridazin-3-one as a starting material, the procedures of Example 12 were repeated likewise, whereby the title compound was obtained in a yield of 30.4%.

Pale yellow oil. $^1$H-NMR (CDCl$_3$) δ: 2.22(2H,quintet,J= 7.32 Hz), 2.30(3H,s), 2.72(2H,t,J=7.33 Hz), 3.79(3H,s), 3.80(3H,s), 4.30(2H,t,J=7.32 Hz), 6.78(2H,d,J=8.78 Hz), 6.80(2H,d,J=8.79 Hz), 6.86(1H,s), 7.23(2H,d,J=8.79 Hz), 7.09(2H,d,J=5.86 Hz), 7.11(2H,d,J=9.03 Hz). IR (film) cm$^{-1}$: 1652,1610,1514,1296,1247,1179,1033,833, 807,755.

Example 26

Preparation of 5,6-bis(4-methoxyphenyl)-2-(4-fluorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 56.8%.

Pale yellow needles (diethyl ether-hexane). Melting point: 132.3–132.9° C. $^1$H-NMR (CDCl$_3$) δ: 3.79(3H,s), 3.80(3H, s), 5.37(2H,s), 6.78(2H,d,J=8.78 Hz), 6.80(2H,d,J=9.03 Hz), 7.02(2H,d,J=9.03 Hz). IR (KBr) cm$^{-1}$: 1665,1609,1515, 1294,1247,1184,1177,1027, 839.

Example 27

Preparation of 5,6-bis(4-methoxyphenyl)-2-(2,4-difluorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 88.4%.

Pale yellow needles (ethyl acetate-hexane). Melting point: 150.1–150.9° C. $^1$H-NMR (CDCl$_3$) δ: 3.79(3H,s), 3.81(3H, s), 5.44(2H,s), 6.77(2H,d,J=8.79 Hz), 6.81(2H,d,J=8.79 Hz), 6.83–6.88(2H,m), 6.89(1H,s), 7.04(2H,d,J=8.78 Hz), 7.09 (2H,d,J=9.03 Hz), 7.42–7.51(1H,m). IR (KBr) cm$^{-1}$: 1667, 1608,1512,1502,1292,1252,1243,1181, 840,831.

Example 28

Preparation of 5,6-bis(4-methoxyphenyl)-2-(3-fluoro-4-methoxybenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 84.3%.

Pale yellow scales (ethyl acetate-diethyl ether). Melting point: 166.5–167.5° C. $^1$H-NMR (CDCl$_3$) δ: 3.80(6H,s), 3.87(3H,s), 5.32(2H,s), 6.77–6.82(1H,m), 6.78(2H,d,J=9.03 Hz), 6.79(2H,d,J=8.79 Hz), 6.88(1H,s), 6.90–6.96(1H,m), 7.02(2H,d,J=8.79 Hz), 7.11(2H,d,J=8.78 Hz), 7.27–7.32 (1H,m). IR (KBr) cm$^{-1}$: 1662,1609,1516,1275,1248,1183, 837.

Example 29

Preparation of 5,6-bis(4-methoxyphenyl)-2-(3,4-difluorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 51.6%.

Pale yellow prisms (ethyl acetate-diethyl ether). Melting point: 155.4–156.1° C. $^1$H-NMR (CDCl$_3$) δ: 3.79(3H,s), 3.80(3H,s), 5.34(2H,s), 6.79(2H,d,J=8.79 Hz), 6.80(2H,d,J=8.79 Hz), 6.89(1H,s), 7.03(2H,d,J=9.03 Hz), 7.08–7.18(1H,m), 7.10(2H,d,J=8.79 Hz), 7.23–7.31(1H,m), 7.33–7.40(1H,m). IR (KBr) cm$^{-1}$: 1660,1610,1516,1293,1286,1251,1241,1134, 1030,847.

Example 30

Preparation of 5,6-bis(4-methoxyphenyl)-2-(4-fluorocinnamyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 41.0%.

Pale yellow amorphous. Mass (m/e): 442 (M$^+$). $^1$H-NMR (CDCl$_3$) δ: 3.79(3H,s), 3.80(3H,s), 5.00(2H,d,J=6.84 Hz), 6.40(1H,dt,J=15.87,6.60 Hz), 6.71(1H,d,J=15.86 Hz), 6.79 (2H,d,J=8.79 Hz), 6.81(2H,d,J=9.03 Hz), 6.91(1H,s), 6.96–7.06(4H,m), 7.14(2H,d,J=9.04 Hz), 7.34–7.39(2H,m). IR (KBr) cm$^{-1}$: 1660,1609,1509,1296,1249,1178,1027,833.

Example 31

Preparation of 5,6-bis(4-methoxyphenyl)-2-(2,4-difluorocinnamyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 34.8%.

Colorless needles(ethyl acetate-diethyl ether). Melting point: 107.3–108.1° C. $^1$H-NMR (CDCl$_3$) δ: 3.79(3H,s), 3.81(3H,s), 5.01(2H,d,J=6.35 Hz), 6.49(1H,dt,J=15.86,6.60 Hz), 6.74–6.84(3H,m), 6.79(2H,d,J=8.78 Hz), 6.81(2H,d,J=8.79 Hz), 6.91(1H,s), 7.04(2H,d,J=8.78 Hz), 7.14(2H,d,J=8.78 Hz), 7.39–7.48(1H,m). IR (KBr) cm$^{-1}$: 1664,1608,1508,1252,1244,1180,1034,973, 925,833.

Example 32

Preparation of 5,6-bis(4-methoxyphenyl)-2-[3-(2,4-difluorophenyl)propyl]-2H-pyridazin-3-one Using 5,6-bis(4-methoxyphenyl)-2H-pyridazin-3-one as a starting material, the procedures of Example 12 were repeated likewise, whereby the title compound was obtained in a yield of 83.7%.

Yellow amorphous. Mass (m/e): 462 (M$^+$). $^1$H-NMR (CDCl$_3$) δ: 2.22(2H,q,J=7.57 Hz), 2.57(2H,t,J=7.56 Hz), 3.80(3H,s), 3.81(3H,s), 4.30(2H,t,J=7.57 Hz), 6.72–6.83 (2H,m), 6.79(2H,d,J=8.79 Hz), 6.81(2H,d,J=8.79 Hz), 6.87 (1H,s), 7.03(2H,d,J=8.79 Hz), 7.12(2H,d,J=8.79 Hz), 7.16–7.22(1H,m). IR (film) cm$^{-1}$: 1660,1608,1512,1296, 1250,1178,834.

Example 33

Preparation of 5,6-bis(4-methoxyphenyl)-2-( 4-chlorobenzyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 89.2%.

Pale yellow powder (chloroform-diethyl ether). Melting point: 124.2–127.3° C. Mass (m/e): 432 (M$^+$). $^1$H-NMR (CDCl$_3$) δ: 3.79(3H,s), 3.80(3H,s), 5.36(2H,s), 6.78(2H,d, J=8.79 Hz), 6.80(2H,d,J=9.03 Hz), 6.88(1H,s), 7.02(2H,d, J=8.79 Hz), 7.06(2H,d,J=9.04 Hz), 7.31(2H,d,J=8.30 Hz), 7.47(2H,d,J=8.30 Hz). IR (KBr) cm$^{-1}$: 1667,1609,1513, 1249,1184,1176,835.

Example 34

Preparation of 5,6-bis(4-methoxyphenyl)-2-(2,4-dichlorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 67.7%.

Slightly yellowish needles (chloroform-diethyl ether). Melting point: 140.7–141.2° C. $^1$H-NMR (CDCl$_3$) δ: 3.78 (3H,s), 3.81(3H,s), 5.31(2H,s), 6.76(2H,d,J=8.79 Hz), 6.82 (2H,d,J=8.79 Hz), 6.93(1H,s), 7.06(2H,d,J=8.79 Hz), 7.09 (2H,d,J=9.03 Hz), 7.22–7.23(2H,m), 7.43(1H,d,J=1.71 Hz). IR (KBr) cm$^{-1}$: 1664,1608,1587,1512,1468,1252,1181, 1032, 834,696.

Example 35

Preparation of 5,6-bis(4-methoxyphenyl)-2-(3,4-dichlorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 56.4%.

Colorless scales (ethyl acetate-hexane). Melting point: 107.8–109.5° C. $^1$H-NMR (CDCl$_3$) δ: 3.79(3H,s), 3.80(3H, s), 5.34(2H,s), 6.79(2H,d,J=8.79 Hz), 6.81(2H,d,J=8.79 Hz), 6.89(1H,s), 7.03(2H,d,J=9.03 Hz), 7.10(2H,d,J=9.04 Hz), 7.37(1H,dd,J=1.95,8.30 Hz), 7.42(1H,d,J=8.06 Hhz), 7.63 (1H,d,J=1.71 Hz). IR (KBr) cm$^{-1}$: 1661,1609,1514,1471, 1293,1248,1182,1024, 834.

Example 36

Preparation of 5,6-bis(4-methoxyphenyl)-2-(2,6-dichlorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 70.0%.

Yellow needles (diethyl ether). Melting point: 144.0–144.5° C. $^1$H-NMR (CDCl$_3$) δ: 3.75(3H,s), 3.80(3H, s), 5.70(2H,s), 6.67(2H,d,J=8.78 Hz), 6.81(2H,d,J=9.28 Hz), 6.92(2H,d,J=9.28 Hz), 7.04(2H,d,J=8.79 Hz), 7.21(1H,dd, J=7.32,8.79 Hz). IR (KBr) cm$^{-1}$: 1664,1608,1513,1290, 1254,1182,1027,834, 786.

Example 37

Preparation of 5,6-bis(4-methoxyphenyl)-2-(2,4,6-trichlorobenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 28.5%.

Slight yellow needles (diethyl ether-hexane). Melting point: 142.1–142.7° C. $^1$H-NMR (CDCl$_3$) δ: 3.76(3H,s), 3.81(3H,s), 5.65(2H,s), 6.70(2H,d,J=9.03 Hz), 6.81(2H,d,J=9.03 Hz), 6.89(1H,s), 6.94(2H,d,J=9.04 Hz), 6.94(2H,d,J=9.03 Hz), 7.37(2H,s). IR (KBr) cm$^{-1}$: 1663,1609,1512,1248, 1177,1026,838,787.

Example 38

Preparation of 5,6-bis(4-methoxyphenyl)-2-(4-chlorophenethyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 67.4%.

Pale yellow needles (ethyl acetate-hexane). Melting point: 133.0–134.0° C. $^1$H-NMR (CDCl$_3$) δ: 3.17(2H,t,J=7.81 Hz), 3.80(3H,s), 3.81(3H,s), 4.46(2H,t,J=7.81 Hz), 6.78(2H,d,J=8.79 Hz), 6.81(2H,d,J=8.79 Hz), 6.89(1H,s), 7.01(2H,d,J=8.79 Hz), 7.02(2H,d,J=8.79 Hz), 7.22(2H,d,J=8.79 Hz), 7.28 (2H,d,J=8.54 Hz). IR (KBr) cm$^{-1}$: 1648,1608,1514,1297, 1252,1175,836.

Example 39

Preparation of 5,6-bis(4-methoxyphenyl)-2-(2,4-dichlorophenethyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 80.2%.

Pale yellow prisms (diethyl ether-hexane). Melting point: 119.4–120.1° C. $^1$H-NMR (CDCl$_3$) δ: 3.30(2H,t,J=7.08 Hz), 3.79(3H,s), 3.81(3H,s), 4.51(2H,t,J=7.08 Hz), 6.76(2H,d,J=9.03 Hz), 6.81(2H,d,J=9.03 Hz), 6.87(1H,s), 6.96(2H,d,J=8.79 Hz), 7.02(2H,d,J=8.79 Hz), 7.18(2H,d,J=1.71 Hz), 7.40 (1H,d,J=1.71 Hz). IR (KBr) cm$^{-1}$: 1660,1607,1513,1294, 1249,1185,832.

Example 40

Preparation of 5,6-bis(4-methoxyphenyl)-2-(2,4-dichlorocinnamyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 74.5%.

Pale yellow amorphous. Mass (m/e): 492,494(M$^+$). $^1$H-NMR (CDCl$_3$) δ: 3.79(3H,s), 3.81(3H,s), 5.04(2H,dd,J=1.46,6.59 Hz), 6.46(1H,dt,J=15.87,6.59 Hz), 6.78(2H,d,J=8.78 Hz), 6.81(2H,d,J=8.79 Hz), 6.92(1H,s), 7.04(1H,d,J=15.87 Hz), 7.05(2H,d,J=9.03 Hz), 7.19(1H,dd,J=2.19,8.55 Hz), 7.37(1H,d,J=2.20 Hz), 7.84(1H,d,J=8.54 Hz). IR (KBr) cm$^{-1}$: 1664,1609,1512,1469,1248,950,833,746.

Example 41

Preparation of 5,6-bis(4-methoxyphenyl)-2-(4-nitrobenzyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 86.2%.

Pale brown crystals. $^1$H-NMR (CDCl$_3$) δ: 3.80(3H,s), 3.81(3H,s), 5.49(2H,s), 6.79(2H,d,J=8.79 Hz), 6.81(2H,d,J= 8.79 Hz), 6.91(1H,s), 7.03(2H,d,J=8.79 Hz), 7.10(2H,d,J= 8.79 Hz), 8.21(2H,d,J=8.79 Hz). IR (KBr) cm$^{-1}$: 1664,1609, 1522,1347,1247,1185,1025,835.

Example 42

Preparation of 5,6-bis(4-methoxyphenyl)-2-(4-methoxycarbonylbenzyl)-2H-pyridazin-3-one Using 5,6-bis(4-methoxyphenyl)-2H-pyridazin-3-one as a starting material, the procedures of Example 12 were repeated likewise, whereby the title compound was obtained in a yield of 78.8%.

Colorless needles (ethyl acetate-hexane). Melting point: 185.5–186.6° C. Mass (m/e): 456 (M$^+$). $^1$H-NMR (CDCl$_3$) δ: 3.79(3H,s), 3.80(3H,s), 3.91(3H,s), 5.45(2H,s), 6.78(2H, d,J=8.79 Hz), 6.80(2H,d,J=9.04 Hz), 6.90(1H,s), 7.03(2H, d,J=8.79 Hz), 7.09(2H,d,J=9.03 Hz), 7.56(2H,d,J=8.06 Hz), 8.06(2H,d,J=8.54 Hz). IR (KBr) cm$^{-1}$: 1722,1659,1608, 1565,1514,1249,1183,1113, 1021,835.

Example 43

Preparation of 5,6-bis(4-methoxyphenyl)-2-(2-pyridylmethyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 63.1%.

Slight yellow prisms (chloroform-diethyl ether-hexane). Melting point: 116.0–117.0° C. Mass (m/e): 399 (M$^+$). $^1$H-NMR (CDCl$_3$) δ: 3.78(3H,s), 3.81(3H,s), 5.58(2H,s), 6.76(2H,d,J=8.79 Hz), 6.82(2H,d,J=9.04 Hz), 6.95(1H,s), 7.06(2H,d,J=8.79 Hz), 7.12(2H,d,J=8.79 Hz), 7.20(1H,dd, J=4.87,7.56 Hz), 7.30(1H,d,J=7.81 Hz), 7.66(1H,dt,J=1.71, 7.81 Hz), 8.59(1H,d,J=4.88 Hz). IR (KBr) cm$^{-1}$: 1656,1608, 1514,1246,1176,1027,843.

In a manner known per se in the art, the hydrochloride of the title compound was obtained in a yield of 96.4%.

Pale yellow amorphous. $^1$H-NMR (CDCl$_3$) δ: 3.73(3H,s), 3.76(3H,s), 5.54(2H,s), 6.84(2H,d,J=8.79 Hz), 6.90(2H,d,J= 8.79 Hz), 6.95(1H,s), 7.08(2H,d,J=8.79 Hz), 7.14(2H,d,J= 8.79 Hz), 7.54(1H,d,J=7.82 Hz), 8.06(1H,m), 8.66(1H,d,J= 4.64 Hz). IR (KBr) cm$^{-1}$: 1661,1609,1512,1297,1250,1177, 1026,835.

Example 44

Preparation of 5,6-bis(4-methoxyphenyl)-2-(3-pyridylmethyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 71.4%.

Pale yellow prisms (chloroform-diethyl ether). Melting point: 167.4–168.4° C. Mass (m/e): 399 (M$^+$). $^1$H-NMR (CDCl$_3$) δ: 3.80(3H,s), 5.42(2H,s), 6.78(2H,d,J=8.79 Hz), 6.80(2H,d,J=9.03 Hz), 6.89(1H,s), 7.02(2H,d,J=8.79 Hz), 7.11(2H,d,J=8.79 Hz), 7.29(1H,dd,J=4.88,7.81 Hz), 7.88 (1H,td,J=1.71,7.81 Hz), 8.56(1H,dd,J=1.71,4.88 Hz), 8.79 (1H,d,J=1.47 Hz). IR (KBr) cm$^{-1}$: 1669,1608,1514,1294, 1249,1183,839.

In a manner known per se in the art, the methanesulfonate of the title compound was obtained in a yield of 89.1%.

Colorless prisms (methanol-diethyl ether) Melting point: 214.2–214.8° C. $^1$H-NMR (CDCl$_3$+CD$_3$OD) δ: 2.89(3H,s), 3.81(6H,s), 5.55(2H,s), 6.80(2H,d,J=9.03 Hz), 6.82(2H,d,J= 8.79 Hz), 6.91(1H,s), 7.04(2H,d,J=9.03 Hz), 7.11(2H,d,J= 8.79 Hz), 7.92(2H,dd,J=5.86,8.05 Hz), 8.63(1H,d,J=8.31 Hz), 8.93(1H,d,J=5.61 Hz), 8.98(1H,brs). IR (KBr) cm$^{-1}$: 1655,1603,1515,1243,1156,1034,840.

Example 45

Preparation of 5,6-bis(4-methoxyphenyl)-2-(4-pyridylmethyl)-2H-pyridazin-3-one

Using 5,6-bis(4-methoxyphenyl)-2H-pyridazin-3-one as a starting material, the procedures of Example 12 were repeated likewise, whereby the title compound was obtained in a yield of 76.0%.

Orange prisms (chloroform-diethyl ether). Melting point: 182.1–183.1° C. Mass (m/e): 399 (M$^+$). $^1$H-NMR (CDCl$_3$) δ: 3.79(3H,s), 3.81(3H,s), 5.40(2H,s), 6.78(2H,d,J=8.78 Hz), 6.81(2H,d,J=8.06 Hz), 6.92(1H,s), 7.04(2H,dd,J=2.20, 9.03 Hz), 7.10(2H,dd,J=2.20,8.79 Hz), 7.36(2H,dd,J=1.71, 6.10 Hz), 8.59(2H,dd,J=1.71,6.10 Hz). IR (KBr) cm$^{-1}$: 1660,1610,1513,1294,1247,1174,1028,845.

In a manner known per se in the art, the methanesulfonate of the title compound was obtained in a yield of 86.0%.

Slight yellow prisms (methanol-diethyl ether). Melting point: 219.0–221.0° C. (decomposed) $^1$H-NMR (CD$_3$OD) δ: 2.70(3H,s), 3.77(3H,s), 3.79(3H,s), 5.73(2H,s), 6.82(2H,d, J=8.79 Hz), 6.88(2H,d,J=8.79 Hz), 7.00(1H,s), 7.13(2H,d, J=9.03 Hz), 7.15(2H,d,J=8.79 Hz), 8.07(2H,d,J=6.84 Hz), 8.83(2H,d,J=6.83 Hz). IR (KBr) cm$^{-1}$: 1656,1603,1514, 1298,1245,1178,1163,1035, 840.

Example 46

Preparation of 6-(4-methoxyphenyl)-5-phenyl-2-cinnamyl-2H-pyridazin-3-one

Using 6-(4-methoxyphenyl)-5-phenyl-2H-pyridazin-3-one as a starting material, the procedures of Example 12 were repeated likewise, whereby the title compound was obtained in a yield of 73.9%.

Orange prisms (ethyl acetate-hexane). Melting point: 135.8–137.1° C. $^1$H-NMR (CDCl$_3$) δ: 3.78(3H,s), 5.02(2H, dd,J=0.98,6.67 Hz), 6.50(1H,dt,J=15.86,6.67 Hz), 6.71–6.80(3H,m), 6.94(1H,s), 7.06–7.15(4H,m), 7.20–7.34 (6H,m), 7.36–7.44(2H,m). IR (KBr) cm$^{-1}$: 1664,1609,1517, 1250,1182,1023,965,840.

Example 47

Preparation of 6-(3,4-dimethoxyphenyl)-5-(4-methoxyphenyl)-2-(2,4-dichlorobenzyl)-2H-pyridazin-3-one Using 6-(3,4-dimethoxyphenyl)-5-(4-methoxyphenyl)-2H-pyridazin-3-one as a starting material, the procedures of Example 12 were repeated likewise, whereby the title compound was obtained in a yield of 69.5%.

Colorless needles (ethyl acetate-hexane). Melting point: 118.6–119.8° C. $^1$H-NMR (CDCl$_3$) δ: 3.18(2H,t,J=7.32 Hz), 3.63(3H,s), 3.80(3H,s), 3.87(3H,s), 4.48(2H,t,J=7.32 Hz), 6.52(1H,d,J=1.95 Hz), 6.67(1H,dd,J=1.95,8.30 Hz), 6.76 (1H,d,J=8.30 Hz), 6.81(2H,d,J=9.03 Hz), 6.91(1H,s), 7.03 (2H,d,J=8.79 Hz), 7.21(2H,d,J=8.55 Hz), 7.28(2H,d,J=8.54 Hz). IR (KBr) cm$^{-1}$: 1668,1519,1513,1469,1270,1253,1175, 1140.

Example 48

Preparation of 6-(3,4-dimethoxyphenyl)-5-(4-methoxyphenyl)-2-(4-chlorophenethyl)-2H-pyridazin-3-one Using 6-(3,4-dimethoxyphenyl)-5-( 4-methoxyphenyl)-2H-pyridazin-3-one as a starting material, the procedures of Example 12 were repeated likewise, whereby the title compound was obtained in a yield of 87.0%.

Pale yellow amorphous. Mass (m/e): 476 (M$^+$). $^1$H-NMR (CDCl$_3$) δ: 3.62(3H,s), 3.81(3H,s), 3.86(3H,s), 5.52(2H,s), 6.65(1H,s), 6.73(2H,d,J=1.22 Hz), 6.83(2H,d,J=8.79 Hz), 6.94(1H,s), 7.07(2H,d,J=8.79 Hz), 7.22(1H,dd,J=1.95,8.30 Hz), 7.30(1H,d,J=8.30 Hz), 7.44(1H,d,J=2.20 Hz). IR (KBr) cm$^{-1}$: 1660,1608,1512,1267,1251,1218,1175,1027, 834.

Example 49

Preparation of 5-(4-chlorophenyl)-6-(4-methoxyphenyl)-2-benzyl-2H-pyridazin-3-one Using 5-(4-chlorophenyl)-6-(4-methoxyphenyl)-2H-pyridazin-3-one as a starting material, the procedures of Example 12 were repeated likewise, whereby the title compound was obtained in a yield of 65.5%.

Pale yellow prisms (diethyl ether-hexane). Melting point: 165.0–167.0° C. Mass (m/e): 402,404 (M$^+$). $^1$H-NMR (CDCl$_3$) δ: 3.80(3H,s), 5.42(2H,s), 6.79(2H,d,J=8.79 Hz), 6.89(1H,s), 7.03(2H,d,J=8.79 Hz), 7.08(2H,d,J=9.04 Hz), 7.27(2H,d,J=8.79 Hz), 7.29–7.40(3H,m), 7.52(2H,dd,J= 1.71,8.06 Hz). IR (KBr) cm$^{-1}$: 1672,1608,1515,1248,1184, 833.

Example 50

Preparation of 5-(4-chlorophenyl)-6-(4-methoxyphenyl)-2-(4-pyridylmethyl)-2H-pyridazin-3-one Using 5-(4-chlorophenyl)-6-(4-methoxyphenyl)-2H-pyridazin-3-one as a starting material, the procedures of Example 12 were repeated likewise, whereby the title compound was obtained in a yield of 73.2%.

Slightly pale yellow prisms (diethyl ether). Melting point: 142.0–143.0° C. Mass (m/e): 403,405 (M$^+$). $^1$H-NMR (CDCl$_3$) δ: 3.80(3H,s), 5.41(2H,s), 6.79(2H,dd,J=2.20,8.79 Hz), 6.95(1H,s), 7.06(2H,dd,J=1.95,8.54 Hz), 7.07(2H,dd, J=2.20,9.03 Hz), 7.29(2H,dd,J=1.95,8.55 Hz), 7.36(2H,dd, J=1.71,6.11 Hz), 8.60(2H,dd,J=1.71,6.11 Hz). IR (KBr) cm$^{-1}$: 1660,1601,1587,1514,1247,1174,1091,953, 844,789.

In a manner known per se in the art, the methanesulfonate of the title compound was obtained in a yield of 66.8%.

Colorless prisms (methanol-ethyl acetate). Melting point: 201.5–203.0° C. $^1$H-NMR (CDCl$_3$) δ: 2.89(3H,s), 3.81(3H, s), 5.60(2H,s), 6.80(2H,d,J=8.79 Hz), 6.97(1H,s), 7.06(2H, d,J=9.04 Hz), 7.07(2H,d,J=8.79 Hz), 7.31(2H,d,J=8.79 Hz), 7.95(2H,d,J=6.83 Hz), 8.88(2H,d,J=6.83 Hz). IR (KBr) cm$^{-1}$ 1662,1609,1515,1247,1209,1192,1179,1036, 842,785.

Example 51

Preparation of 2-benzyl-5-(4-chlorophenyl)-6-[4-(methylthio)phenyl]-2H-pyridazin-3-one 5-(4-Chlorophenyl)-6-[4-(methylthio)phenyl]-2H-pyridazin-3-one (500 mg, 1.52 mmol) was dissolved in anhydrous N,N-dimethylformamide (20 ml), followed by the addition of potassium carbonate (420 mg, 3.04 mmol). Benzyl bromide (286 mg, 1.67 mmol) was then added at 50° C., and the mixture was stirred at 70° C. for 40 minutes. After the temperature of the reaction mixture was allowed to cool down to room temperature, the reaction mixture was diluted with ethyl acetate. The mixture was washed with water and then with a brine, and was then dried over anhydrous sodium sulfate. The solvent was distilled off. The residue so obtained was separated and purified by chromatography on a silica gel column [hexane/ethyl acetate (3/1)], whereby pale yellow crystals were obtained. The crystals were recrystallized from ethyl acetate-hexane, whereby the title compound (552.6 mg, 86.8%) was obtained as pale yellow prisms.

Melting point: 155.0–155.6° C. Mass (m/e): 418,420 (M$^+$). $^1$H-NMR (CDCl$_3$) δ: 2.46(3H,s), 5.42(2H,s), 6.90(1H, s), 7.04(2H,d,J=8.40 Hz), 7.06(2H,d,J=8.40 Hz 7.11(2H,d, J=8.59 Hz), 7.27(2H,d,J=8.40 Hz), 7.31–7.38(3H,m), 7.53 (2H,d,J=6.83 Hz). IR (KBr) cm$^{-1}$: 3032,2925,1669,1581, 1493,1095,950,829, 695.

Example 52

Preparation of 5-(4-chlorophenyl)-6-(4-(methylthio) phenyl]-2-cyclopropylmethyl-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 84.0%.

Pale yellow crystalline powder (diethyl ether). Melting point: 142.0–143.0° C. Mass (m/e): 382,384 (M$^+$). $^1$H-NMR (CDCl$_3$) δ: 0.48–0.61(4H,m), 1.42–1.48(1H,m), 2.47(3H,s), 4.12(2H,d,J=7.42 Hz), 6.91(1H,s), 7.08(2H,d,J=8.40 Hz), 7.10(2H,d,J=7.62 Hz), 7.13(2H,d,J=8.79 Hz), 7.29(2H,d,J= 8.40 Hz). IR (KBr) cm$^{-1}$: 1664,1598,1583,1493,1092,952, 829.

Example 53

Preparation of 5-(4-chlorophenyl)-6-[4-(methylthio) phenyl]-2-(2,4-difluorobenzyl)-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 79.0%.

Pale yellow prisms (ethyl acetate-hexane). Melting point: 157.4–157.5° C. Mass (m/e): 454,456 (M$^+$). $^1$H-NMR (CDCl$_3$) δ: 2.46(3H,s), 5.45(2H,s), 6.82(2H,m), 6.91(1H,s), 7.03–7.07(4H,m), 7.12(2H,d,J=8.40 Hz), 7.29(2H,d,J=8.40 Hz), 7.45–7.51(1H,m). IR (KBr) cm$^{-1}$: 1672,1600,1506, 1274,1140,1093,972,829.

Example 54

Preparation of 5-(4-chlorophenyl)-6-[4-(methylthio) phenyl]-2-(2,4-dichlorobenzyl)-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 97.1%.

Colorless prisms (ethyl acetate-hexane). Melting point: 154.5–155.0° C. Mass (m/e): 486,488,490 (M$^+$). $^1$H-NMR (CDCl$_3$) δ: 2.46(3H,s), 5.51(2H,s), 6.94(1H,s), 7.04(2H,d, J=8.55 Hz), 7.09(2H,d,J=8.55 Hz), 7.08(2H,d,J=8.79 Hz), 7.22(1H,dd,J=8.30,1.83 Hz), 7.24–7.33(3H,m), 7.43(1H,d, J=1.83 Hz). IR (KBr) cm$^{-1}$: 1660,1585,1484,1095,829,819.

Example 55

Preparation of 5-(4-chlorophenyl)-6-[4-(methylthio) phenyl]-2-(3-pyridylmethyl)-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 65.6%.

Pale yellow prisms (ethyl acetate-hexane). Melting point: 148.4–148.5° C. Mass (m/e): 419 (M$^+$). $^1$H-NMR (CDCl$_3$) δ: 2.47(3H,s), 5.42(2H,s), 6.91(1H,s), 7.03–7.13(6H,m), 7.27–7.32(3H,m), 7.88(1H,tt,J=7.81,1.95 Hz), 8.57(1H,dd, J=4.88,1.71 Hz), 8.79(1H,d,J=1.95 Hz). IR (KBr) cm$^{-1}$: 1665,1580,1490,1428,1311,1093,834.

Example 56

Preparation of 5-(4-chlorophenyl)-6-[4-(methylthio) phenyl]-2-cinnamyl-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 73.9%.

Colorless prisms (chloroform-hexane). Melting point: 109.3–110.2° C. Mass (m/e): 444,446 (M$^+$). $^1$H-NMR (CDCl$_3$) δ: 2.47(3H,s), 5.01(2H,dd,J=6.71,1.10 Hz), 6.48 (1H,dt,J=15.75,6.71 Hz), 6.75(1H,d,J=15.75 Hz), 6.93(1H, s), 7.00–7.14(6H,m), 7.20–7.33(5H,m), 7.34–7.42(2H,m). IR (KBr) cm$^{-1}$: 1665,1598,1582,1493,1095,967,948.

Example 57

Preparation of 5-(4-chlorophenyl)-6-[4-(methylthio) phenyl]-2-(3-phenylpropyl)-2H-pyridazin-3-one Using 5-(4-chlorophenyl)-6-[4-(methylthio)phenyl]-2H-pyridazin-3-one as a starting material, the procedures of Example 51 were repeated likewise, whereby the title compound was obtained in a yield of 97.5%.

Pale yellow oil. Mass (m/e): 446,448 (M$^+$). $^1$H-NMR (CDCl$_3$) δ: 2.23(2H,q,J=7.48 Hz), 2.47(3H,s), 2.76(2H,t,J= 7.48 Hz), 4.32(2H,t,J=7.48 Hz), 6.87(1H,s), 7.02–7.31(13H, m). IR (KBr) cm$^{-1}$: 1665,1598,1582,1493,1095,967,948.

Example 58

Preparation of 5-(4-fluorophenyl)-6-[4-(methylthio) phenyl]-2-cyclopropylmethyl-2H-pyridazin-3-one Using 5-(4-fluorophenyl)-6-[4-(methylthio)phenyl]-2H-pyridazin-3-one as a starting material, the procedures of Example 51 were repeated likewise, whereby the title compound was obtained in a yield of 99.7%.

Yellow amorphous. $^1$H-NMR (CDCl$_3$) δ: 0.48–0.60(4H, m), 1.43–1.49(1H,m), 2.73(3H,s), 4.14(2H,d,J=7.32 Hz), 6.92(1H,s), 7.01(2H,t,J=8.54 Hz), 7.09–7.12(2H,m), 7.36 (2H,d,J=8.05 Hz), 7.56(2H,d,J=8.29 Hz). IR (KBr) cm$^{-1}$: 1664,1599,1578,1510,1229,1093,840.

Example 59

Preparation of 5-(4-fluorophenyl)-6-[4-(methylthio) phenyl]-2-cyclopentylmethyl-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 76.6%.

Colorless amorphous. Mass (m/e): 394 (M$^+$). $^1$H-NMR (CDCl$_3$) δ: 1.36–1.45(2H,m), 1.54–1.60(2H,m), 1.66–1.80 (4H,m), 2.46(3H,s), 2.53–2.64(1H,m), 4.21(2H,d,J=7.56 Hz), 6.90(1H,s), 7.00(2H,t,J=8.54 Hz), 7.07–7.13(6H,m). IR (KBr) cm$^{-1}$: 1669,1598,1578,1510,1228,1160,1096,840, 680.

Example 60

Preparation of 5-(4-fluorophenyl)-6-[4-(methylthio)phenyl]-2-(2,2,2-trifluoroethyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 72.3%.

Colorless amorphous. Mass (m/e): 394,395 (M$^+$). $^1$H-NMR (CDCl$_3$) δ: 2.47(3H,s), 4.88(2H,q,J=8.40 Hz), 6.95(1H,s), 6.99–7.14(8H,m). IR (KBr) cm$^{-1}$: 1678,1597, 1513,1335,1263,1088,843,827.

Example 61

Preparation of 5-(4-fluorophenyl)-6-[4-(methylthio)phenyl]-2-benzyl-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 82.0%.

Colorless needles (ethyl acetate-hexane). Melting point: 140.6–140.7° C. Mass (m/e): 402 (M$^+$). $^1$H-NMR (CDCl$_3$) δ: 2.46(3H,s), 5.42(2H,s), 6.90(1H,s), 6.95–7.12(8H,m), 7.31–7.39(3H,m), 7.52–7.55(2H,m). IR (KBr) cm$^{-1}$: 1664, 1601,1509,1232,1098,841,699.

Example 62

Preparation of 5-(4-fluorophenyl)-6-[4-(methylthio)phenyl]-2-(4-methoxybenzyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 96.2%.

Colorless needles (ethyl acetate-hexane). Melting point: 165.3–165.7° C. Mass (m/e): 432 (M$^+$). $^1$H-NMR (CDCl$_3$) δ: 2.46(3H,s), 3.80(3H,s), 5.35(2H,s), 6.87(1H,s), 6.88(2H,d,J=6.83 Hz), 6.98(2H,t,J=8.66 Hz), 7.01–7.16(6H,m), 7.50 (2H,d,J=8.78 Hz). IR (KBr) cm$^{-1}$: 1663,1511,1246,1233, 842.

Example 63

Preparation of 5-(4-fluorophenyl)-6-[4-(methylthio)phenyl]-2-[4-(methylthio)benzyl]-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 80.3%.

Colorless plate crystals (ethyl acetate-hexane). Melting point: 116.0–116.1° C. Mass (m/e): 448 (M$^+$). $^1$H-NMR (CDCl$_3$) δ: 2.47(6H,s), 5.36(2H,s), 6.89(1H,s), 6.99(2H,t,J=8.69 Hz), 7.04–7.12(6H,m), 7.24(2H,d,J=8.40 Hz), 7.47(2H,d,J=8.40 Hz). IR (KBr) cm$^{-1}$: 1660,1599,1576,1511,1495, 1233,1161,1093, 950,841,678.

Example 64

Preparation of 5-(4-fluorophenyl)-6-[4-(methylthio)phenyl]-2-(4-fluorobenzyl)-2H-pyridazin-3-one Using 5-(4-fluorophenyl)-6-[4-(methylthio)-phenyl]-2H-pyridazin-3-one as a starting material, the procedures of Example 58 were repeated likewise, whereby the title compound was obtained in a yield of 89.8%.

Colorless needles (ethyl acetate-hexane). Melting point: 155.9–156.2° C. Mass (m/e): 448,449 (M$^+$). $^1$H-NMR (CDCl$_3$) δ: 2.46(3H,s), 5.37(2H,s), 6.89(1H,s), 6.95–7.13 (9H,m), 7.30–7.35(1H,m), 7.52(2H,dd,J=8.54,5.37 Hz). IR (KBr) cm$^{-1}$: 1664,1602,1510,1225,847,812.

Example 65

Preparation of 5-(4-fluorophenyl)-6-[4-(methylthio)phenyl]-2-(2,4-dichlorobenzyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 61.7%.

Colorless needles (ethyl acetate-hexane). Melting point: 139.3–139.5° C. Mass (m/e): 470,472 (M$^+$). $^1$H-NMR (CDCl$_3$) δ: 2.44(3H,s), 5.51(2H,s), 6.94(1H,s), 6.97–7.43 (11H,m). IR (KBr) cm$^{-1}$: 1665,1583,1510,1233,1098,828.

Example 66

Preparation of 5-(4-fluorophenyl)-6-[4-(methylthio)phenyl]-2-(2,4-difluorobenzyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 21.0%.

Colorless oil. $^1$H-NMR (CDCl$_3$) δ: 2.46(3H,s), 5.45(2H, s), 6.78–6.88(2H,m), 6.91(1H,s), 6.98–7.12(8H,m), 7.37–7.49(1H,m). IR (KBr) cm$^{-1}$: 1652,1605,1575,1507, 1235,1091,972,842.

Example 67

Preparation of 5-(4-fluorophenyl)-6-[4-(methylthio)phenyl]-2-(3-pyridylmethyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 31.7%.

Colorless needles (acetone-water). Melting point: 159.8–160.7° C. Mass (m/e): 403 (M$^+$). $^1$H-NMR (CDCl$_3$) δ: 2.46(3H,s), 5.43(2H,s), 6.91(1H,s), 6.96–7.13(8H,m), 7.30(1H,dd,J=8.30,5.37 Hz), 7.89(1H,dt,J=7.80,1.96 Hz), 8.58(1H,dd,J=4.77,1.51 Hz), 8.79(1H,d,J=1.71 Hz).

IR (KBr) cm$^{-1}$: 1661,1580,1509,1216,1095,955,852,832, 680.

Example 68

Preparation of 5-(4-fluorophenyl)-6-[4-(methylthio)phenyl]-2-(4-pyridylmethyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 23.5%.

Colorless crystals. Melting point: 223.4–224.3% Mass (m/e): 403 (M$^+$). $^1$H-NMR (DMSO-D$_6$) δ: 2.44(3H,s), 5.39 (2H,s), 7.04(1H,s), 7.08(2H,d,J=8.29 Hz), 7.16(2H,d,J=8.54 Hz), 7.19–7.29(4H,m), 7.34(2H,d,J=5.61 Hz), 8.35(2H,d,J=5.85 Hz).

IR (KBr) cm$^{-1}$: 1664,1601,1582,1562,1510,1417,1219, 852, 683.

Example 69

Preparation of 5-(4-fluorophenyl)-6-[4-(methylthio)phenyl]-2-(2,4-difluorocinnamyl)-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 49.5%.

Colorless amorphous. Mass (m/e): 464 (M$^+$). $^1$H-NMR (CDCl$_3$) δ: 2.46(3H,s), 5.02(2H,d,J=6.34 Hz), 6.48(1H,dt, J=16.11,6.59 Hz), 6.74–6.85(3H,m), 6.93(1H,s), 6.97–7.14 (8H,m), 7.39–7.45(1H,m). IR (KBr) cm$^{-1}$: 1664,1554,1502, 1273,1232,1094,966,841.

Example 70

Preparation of 2-(4-chlorocinnamyl)-5-(4-fluorophenyl)-6-[4-(methylthio)phenyl]-2H-pyridazin-3-one Using 5-(4-fluorophenyl)-6-[4-(methylthio)phenyl]-2H-pyridazin-3-one as a starting material, the procedures of Example 58 were repeated likewise, whereby the title compound was obtained in a yield of 67.5%.

Colorless needles (ethyl acetate-hexane). Melting point: 118.6–118.9° C. $^1$H-NMR (CDCl$_3$) δ: 2.46(3H,s), 5.00(2H, d,J=5.62 Hz), 6.44(1H,dt,J=15.87,6.59 Hz), 6.70(1H,d,J= 16.12 Hz), 6.93(1H,s), 6.97–7.13(8H,m), 7.26(2H,d,J=5.79 Hz), 7.33(2H,d,J=8.55 Hz). IR (KBr) cm$^{-1}$: 1669,1605, 1575,1509,1492,1095,841,830.

Example 71

Preparation of 2-benzyl-6-[4-(methylthio)phenyl]-5-phenyl-2H-pyridazin-3-one

Using 6-[4-(methylthio)phenyl]-5-phenyl-2H-pyridazin-3-one as a starting material, the procedures of Example 51 were repeated likewise, whereby the title compound was obtained in a yield of 55.3%.

Colorless needles (ethyl acetate). Melting point: 157.3–158.4° C. Mass (m/e): 384,386 (M$^+$). $^1$H-NMR (CDCl$_3$) δ: 2.45(3H,s), 5.43(2H,s), 6.92(1H,s), 7.05–7.12 (6H,m), 7.25–7.40(6H,m), 7.51–7.57(2H,m). IR (KBr) cm$^{-1}$: 1665,1597,1585,1493,775,711.

Example 72

Preparation of 2-acetonyl-6-(4-methoxyphenyl)-5-(4-pyridyl)-2H-pyridazin-3-one

Using 6-(4-methoxyphenyl)-5-(4-pyridyl)-2H-pyridazin-3-one as a starting material, propargyl chloride was treated in a similar manner as in Example 12, whereby the title compound was obtained in a yield of 29.3%.

Colorless crystalline powder (diethyl ether-hexane). Melting point: 68.3–70.6° C. $^1$H-NMR (CDCl$_3$) δ: 2.30(3H,s), 3.78(3H,s), 5.07(2H,s), 6.77(2H,d,J=8.54 Hz), 6.98(1H,s), 7.04–7.10(4H,m), 8.58(2H,td,J=0.85,4.39 Hz). IR (KBr) cm$^{-1}$: 1734,1669,1610,1517,1250,1170.

Example 73

Preparation of 2-cyclopropylmethyl-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 70.8%.

Colorless needles (ethyl acetate-hexane). Melting point: 128.3–130.1° C. $^1$H-NMR (CDCl$_3$) δ: 0.47–0.54(2H,m), 0.55–0.62(2H,m), 1.40–1.52(1H,m), 3.79(3H,s), 4.14(2H,d, J=7.08 Hz), 6.79(2H,d,J=8.92 Hz), 6.95(1H,s), 7.07(2H,dd, J=1.65,4.91 Hz), 7.09(2H,d,J=8.92 Hz), 8.58(2H,dd,J=1.65, 4.91 Hz). IR (KBr) cm$^{-1}$: 1664,1610,1582,1572,1517,1254, 1024,834.

Example 74

Preparation of 2-cyclopentylmethyl-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 32.0%.

Colorless prisms (methylene chloride-hexane). Melting point: 119.3–120.2° C. $^1$H-NMR (CDCl$_3$) δ: 1.33–1.49(2H, m), 1.52–1.64(2H,m), 1.65–1.84(4H,m), 2.59(1H,septet,J= 7.61 Hz), 3.79(3H,s), 4.22(2H,d,J=7.61 Hz), 6.79(2H,d,J= 8.85 Hz), 6.94(1H,s), 7.07(2H,dd,J=1.71,4.44 Hz), 7.09(2H, d,J=8.88 Hz), 8.57(2H,dd,J=1.71,4.44 Hz). IR (KBr) cm$^{-1}$: 1668,1610,1601,1572,1517,1250,1180,827.

Example 75

Preparation of 2-benzyl-6-(4-methoxyphenyl)-5-(4-pyridyl)-2H-pyridazin-3-one

Using 6-(4-methoxyphenyl)-5-(4-pyridyl)-2H-pyridazin-3-one as a starting material, the procedures of Example 72 were repeated likewise, whereby the title compound was obtained in a yield of 43.1%.

Pale yellow needles (ethyl acetate-hexane). Melting point: 153.9–155.1° C. $^1$H-NMR (CDCl$_3$) δ: 3.78(3H,s), 5.42(2H, s), 6.78(2H,d,J=8.66 Hz), 6.93(1H,s), 7.03(2H,d,J=5.73 Hz), 7.06(2H,d,J=8.66 Hz), 7.35–7.39(3H,m), 7.54(2H,d,J=7.07 Hz), 8.56(2H,d,J=5.73 Hz). IR (KBr) cm$^{-1}$: 1668,1601, 1517,1251,1182,826,761.

Example 76

Preparation of 2-(4-methoxybenzyl)-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 37.2%.

Colorless prisms (ethyl acetate-hexane). Melting point: 142.6–143.3° C. $^1$H-NMR (CDCl$_3$) δ: 3.78(6H,s), 5.36(2H, s), 6.78(2H,d,J=8.66 Hz), 6.88(2H,d,J=8.42 Hz), 6.92(1H, d,J=1.46 Hz), 7.02(2H,d,J=4.64 Hz), 7.07(2H,d,J=8.66 Hz), 7.50(2H,d,J=8.42 Hz), 8.56(2H,d,J=3.64 Hz). IR (KBr) cm$^{-1}$: 1665,1609,1598,1570,1514,1296,1250,1179, 1025, 844,829.

Example 77

Preparation of 2-(4-fluorobenzyl)-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 42.2%.

Colorless prisms (ethyl acetate-hexane). Melting point: 154.3–155.2° C. $^1$H-NMR (CDCl$_3$) δ: 3.78(3H,s), 5.38(2H, s), 6.79(2H,d,J=8.78 Hz), 6.93(1H,s), 6.98–7.04(4H,m), 7.07(2H,d,J=8.78 Hz), 7.53(2H,dd.J=8.54,5.61 Hz), 7.56 (2H,d,J=5.86 Hz). IR (KBr) cm$^{-1}$: 1666,1609,1601,1572, 1517,1509,1297,1253, 1226,1182,1158,1028,842,826.

Example 78

Preparation of 2-(4-chlorobenzyl)-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 81.2%.

Orange prisms (ethyl acetate-hexane). Melting point: 175.4–176.1° C. $^1$H-NMR (CDCl$_3$) δ: 3.79(3H,s), 5.38(2H, s), 6.79(2H,d,J=8.90 Hz), 6.93(1H,s), 7.03(2H,dd,J=1.70, 4.37 Hz), 7.05(2H,d,J=8.90 Hz), 7.33(2H,d,J=8.42 Hz), 7.48 (2H,d,J=8.42 Hz), 8.56(2H,dd,J=1.70,4.37 Hz). IR (KBr) cm$^{-1}$: 1665,1608,1598,1571,1517,1492,1252,1181, 843, 827.

Example 79

Preparation of 2-(2,4-dichlorobenzyl)-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 47.2%.

Pale yellowish-brown prisms (methanol-diethyl ether). Melting point: 151.3–153.0° C. $^1$H-NMR (CDCl$_3$) δ: 3.78 (3H,s), 5.53(2H,s), 6.77(2H,d,J=8.79 Hz), 6.98(1H,s), 7.04 (2H,d,J=8.79 Hz), 7.07(2H,d,J=6.10 Hz), 7.22(1H,dd,J=1.96,8.31 Hz), 7.29(2H,d,J=8.31 Hz), 7.44(1H,d,J=1.96 Hz), 8.59(2H,d,J=6.10 Hz). IR (KBr) cm$^{-1}$: 1658,1610,1596, 1517,1490,1250,1185.

Example 80

Preparation of 6-(4-methoxyphenyl)-5-(4-pyridyl)-2-(3-pyridylmethyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 55.1%.

Colorless prisms (ethyl acetate-hexane). Melting point: 161.7–162.3° C. $^1$H-NMR (CDCl$_3$) δ: 3.79(3H,s), 5.44(2H, s), 6.79(2H,d,J=8.78 Hz), 6.95(1H,s), 7.04(2H,dd,J=1.71, 4.39 Hz), 7.06(2H,d,J=8.78 Hz), 7.31(1H,ddd,J=0.73,4.88, 7.81 Hz), 7.91(1H,td,J=1.95,7.81 Hz), 8.56–8.60(3H,m), 8.81(1H,d,J=1.95 Hz). IR (KBr) cm$^{-1}$: 1665,1610,1599, 1587,1574,1518,1264,1252, 1181,1023,839,829,716.

Example 81

Preparation of 6-(4-methoxyphenyl)-5-(4-pyridyl)-2-(4-pyridylmethyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 45.4%.

Colorless prisms (chloroform-hexane). Melting point: 192.8–194.4° C. $^1$H-NMR (CDCl$_3$) δ: 3.79(3H,s), 5.42(2H, s), 6.79(2H,d,J=8.90 Hz), 6.98(1H,s), 7.06(2H,dd,J=1.71, 4.39 Hz), 7.06(2H,d,J=8.90 Hz), 7.38(2H,dd,J=1.71,4.39 Hz), 8.58(2H,dd,J=1.71,4.39 Hz), 8.60(2H,dd,J=1.71,4.39 Hz). IR (KBr) cm$^{-1}$: 1665,1602,1585,1516,1417,1301,1250, 1174, 838,720.

Example 82

Preparation of 2-cinnamyl-6-(4-methoxyphenyl)-5-(4-pyridyl)-2H-pyridazin-3-one

Using 6-(4-methoxyphenyl)-5-(4-pyridyl)-2H-pyridazin-3-one as a starting material, the procedures of Example 72 were repeated likewise, whereby the title compound was obtained in a yield of 29.9%.

Pale yellow amorphous. $^1$H-NMR (CDCl$_3$) δ: 3.79(3H,s), 5.02(2H,dd,J=0.98,6.59 Hz), 6.47(1H,td,J=6.59,15.86 Hz), 6.77(1H,dd,J=0.98,15.86 Hz), 6.79(2H,d,J=8.79 Hz), 6.96 (1H,s), 7.05(2H,d,J=6.11 Hz), 7.09(2H,d,J=8.79 Hz), 7.21–7.31(3H,m), 7.33–7.40(2H,m), 8.57(2H,d,J=6.11 Hz). IR (KBr) cm$^{-1}$: 1668,1609,1516,1485,1482,1251,1178.

Example 83

Preparation of 6-(4-methoxyphenyl)-5-(4-pyridyl)-2-(3-phenylpropyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 70.7%. Reddish brown prisms (ethyl acetate-diethyl ether-hexane). Melting point: 67.7–68.3° C. $^1$H-NMR (CDCl$_3$) δ: 2.26(2H,quintet,J=7.33 Hz), 2.77(2H, t,J=7.33 Hz), 3.79(3H,s), 4.33(2H,t,J=7.33 Hz), 6.79(2H,d, J=8.79 Hz), 6.90(1H,s), 7.01(2H,d,J=6.11 Hz), 7.06(2H,d, J=8.79 Hz), 7.15–7.30(5H,m), 8.57(2H,d,J=6.11 Hz). IR (KBr) cm$^{-1}$: 1665,1608,1517,1496,1298,1252,1181.

Example 84

Preparation of 2-(2,4-difluorocinnamyl)-6-(4-methoxyphenyl)-5-(4-pyridyl)-2H-pyridazin-3-one Using 6-(4-methoxyphenyl)-5-(4-pyridyl)-2H-pyridazin-3-one as a starting material, the procedures of Example 72 were repeated likewise, whereby the title compound was obtained in a yield of 30.7%.

Colorless crystalline powder (ethyl acetate-diethyl ether). Melting point: 55.4–56.9° C. $^1$H-NMR (CDCl$_3$) δ: 3.79(3H, s), 5.03(2H,d,J=6.59 Hz), 6.49(1H,td,J=6.59,16.03 Hz), 6.73–6.88(5H,m), 6.98(1H,s), 7.02–7.15(4H,m), 7.43(1H, dd,J=8.67,15.02 Hz), 8.58(2H,brs). IR (KBr) cm$^{-1}$: 1668, 1610,1516,1502,1297,1251,1178,965, 829.

Example 85

Preparation of 2-benzyl-5-(4-chlorophenyl)-6-[4-(methylsulfinyl)phenyl]-2H-pyridazin-3-one 2-Benzyl-5-(4-chlorophenyl)-6-[4-(methylthio)phenyl]-2H-pyridazin-3-one (100 mg, 0.239 mmol) was dissolved in dichloromethane (5 ml). Under cooling at −20° C., methachloroperbenzoic acid (60%) (68.7 mg, 0.239 mmol) was added. The resulting mixture was stirred through the night until its temperature arose to room temperature. A saturated aqueous solution of sodium hydrogencarbonate was added. After the resulting mixture was extracted with chloroform, the extract was washed with water and then dried over anhydrous sodium sulfate. The solvent was distilled off, and the residue so obtained was then separated and purified by silica gel preparative chromatography [hexane/ethyl acetate (1/2)], whereby the title compound (91.8 mg, 88.4%) was obtained.

Colorless crystalline powder (hexane-diethyl ether) Melting point: 143.7–144.7° C. Mass (m/e): 434,436 (M$^+$). $^1$H-NMR (CDCl$_3$) δ: 2.72(3H,s), 5.43(2H,s), 6.94(1H,s), 7.02(2H,d,J=8.59 Hz), 7.27(2H,d,J=8.30 Hz), 7.29–7.40 (5H,m), 7.49–7.52(2H,m), 7.55(2H,d,J=8.54 Hz). IR (KBr) cm$^{-1}$: 1665,1583,1494,1091,1050,1015,951,833.

Example 86

Preparation of 5-(4-chlorophenyl)-2-cyclopropylmethyl-6-[4-(methylsulfinyl)phenyl]-2H-pyridazin-3-one Using 5-(4-chlorophenyl)-2-cyclopropylmethyl-6-[4-(methylthio)phenyl]-2H-pyridazin-3-one as a starting material, the procedures of Example 85 were repeated likewise, whereby the title compound was obtained in a yield of 77.0%.

Colorless prisms (ethyl acetate-hexane). Melting point: 152.2–152.3° C. Mass (m/e): 398,400 (M$^+$). $^1$H-NMR (CDCl$_3$) δ: 0.48–0.62(4H,m), 1.42–1.49(1H,m), 2.73(3H,s), 4.14(2H,d,J=7.42 Hz), 6.95(1H,s), 7.05(2H,d,J=8.40 Hz), 7.29(2H,d,J=8.40 Hz), 7.36(2H,d,J=8.40 Hz), 7.56(2H,d,J=8.40 Hz). IR (KBr) cm$^{-1}$: 1661,1584,1494,1317,1090,1051, 838.

Example 87

Preparation of 2-cyclopropylmethyl-5-(4-fluorophenyl)-6-[4-(methylsulfinyl)phenyl]-2H-pyridazin-3-one Using 2-cyclopropylmethyl-5-(4-fluorophenyl)-6-[4-(methylthio)phenyl]-2H-pyridazin-3-one as a starting material, the procedures of Example 85 were repeated likewise, whereby the title compound was obtained in a yield of 72.1%.

Colorless prisms (ethyl acetate-hexane). Melting point: 133.3–133.5° C. Mass (m/e): 382 (M$^+$). $^1$H-NMR (CDCl$_3$) δ: 0.49–0.62(4H,m), 1.42–1.48(1H,m), 3.05(3H,s), 4.14(2H, d,J=7.42 Hz), 6.96(1H,s), 7.03(2H,t,J=8.50 Hz), 7.08–7.11 (2H,m), 7.40(2H,d,J=8.40 Hz), 7.85(2H,d,J=8.20 Hz). IR (KBr) cm$^{-1}$: 1664,1582,1511,1220,1055,840,612.

Example 88

Preparation of 2-benzyl-5-(4-fluorophenyl)-6-[4-(methylsulfinyl)phenyl]-2H-pyridazin-3-one Using 2-benzyl-5-(4-fluorophenyl)-6-[4-(methylthio) phenyl]-2H-pyridazin-3-one as a starting material, the procedures of Example 85 were repeated likewise, whereby the title compound was obtained in a yield of 24.2%.

Colorless needles (ethyl acetate-hexane). Melting point: 197.7–198.2° C. $^1$H-NMR (CDCl$_3$) δ: 2.72(3H,s), 5.44(2H, s), 6.99(1H,s), 6.97–7.07(4H,m), 7.31–7.39(5H,m), 7.52–7.56(4H,m). IR (KBr) cm$^{-1}$: 1665,1511,1231,1049, 954,840.

Example 89

Preparation of 5-(4-fluorophenyl)-2-(4-methoxybenzyl)-6-[4-(methylsulfinyl)phenyl]-2H-pyridazin-3-one Using 5-(4-fluorophenyl)-2-(4-methoxybenzyl)-6-[4-(methylthio)phenyl]-2H-pyridazin-3-one as a starting material, the procedures of Example 85 were repeated likewise, whereby the title compound was obtained in a yield of 94.3%.

Colorless powder (ethyl acetate-hexane). Melting point: 81.3–81.5° C. Mass (m/e): 448 (M$^+$). $^1$H-NMR (CDCl$_3$) δ: 2.73(3H,s), 3.79(3H,s), 5.37(2H,s), 6.89(2H,d,J=8.54 Hz), 6.92(1H,s), 6.99(2H,t,J=8.66 Hz), 7.03–7.07(2H,m), 7.33 (2H,d,J=8.54 Hz), 7.50(2H,d,J=8.78 Hz), 7.55(2H,d,J=8.54 Hz). IR (KBr) cm$^{-1}$: 1664,1512,1248,1047,840.

Example 90

Preparation of 2-(4-fluorobenzyl)-5-[4-fluorophenyl)-6-(4-(methylsulfinyl)phenyl]-2H-pyridazin-3-one Using 2-(4-fluorobenzyl)-5-(4-fluorophenyl)-6-[4-(methylthio)phenyl]-2H-pyridazin-3-one as a starting material, the procedures of Example 85 were repeated likewise, whereby the title compound was obtained in a yield of 80.6%.

Colorless needles (ethyl acetate-hexane). Melting point: 198.1–198.3° C. $^1$H-NMR (CDCl$_3$) δ: 2.73(3H,s), 5.39(2H, s), 6.94(1H,s), 6.94–7.08(6H,m), 7.32(2H,d,J=8.06 Hz), 7.50–7.57(2H,m). IR (KBr) cm$^{-1}$: 1665,1511,1225,1157, 1051,850,842.

Example 91

Preparation of 2-(2,4-difluorobenzyl)-5-(4-chlorophenyl)-6-[4-(methylsulfinyl)phenyl]-2H-pyridazin-3-one Using 2-(2,4-difluorobenzyl)-5-(4-chlorophenyl)-6-[4-(methylthio)phenyl]-2H-pyridazin-3-one as a starting material, the procedures of Example 85 were repeated likewise, whereby the title compound was obtained in a yield of 81.1%.

Colorless prisms (ethyl acetate-hexane). Melting point: 155.6–155.7° C. Mass (m/e): 470,472 (M$^+$). $^1$H-NMR (CDCl$_3$) δ: 2.72(3H,s), 5.46(2H,s), 6.83–6.90(2H,m), 6.95 (1H,s), 7.03(2H,d,J=8.59 Hz), 7.29(2H,d,J=8.40 Hz), 7.31 (2H,d,J=8.20 Hz), 7.50–7.52(1H,m), 7.55(2H,d,J=8.20 Hz). IR (KBr) cm$^{-1}$: 1667,1604,1506,1272,1052,971,951,838.

Example 92

Preparation of 5-(4-chlorophenyl)-2-(2,4-dichlorobenzyl)-6-[4-(methylsulfinyl)phenyl]-2H-pyridazin-3-one Using 5-(4-chlorophenyl)-2-(2,4-dichlorobenzyl)-6-[4-(methylthio)phenyl]-2H-pyridazin-3-one as a starting material, the procedures of Example 85 were repeated likewise, whereby the title compound was obtained in a yield of 71.6%.

Colorless needles (chloroform-hexane). Melting point: 236.5–237.3° C. Mass (m/e): 502,504 (M$^+$). $^1$H-NMR (CDCl$_3$) δ: 2.72(3H,s), 5.53(2H,s), 6.98(1H,s), 7.05(2H,d, J=8.55 Hz), 7.24(1H,dd,J=8.30,2.03 Hz), 7.27–7.34(5H,m), 7.45(1H,d,J=8.03 Hz), 7.54(2H,d,J=8.79 Hz). IR (KBr) cm 1: 1665,1588,1492,1473,1091,1051,1016,954, 835.

Example 93

Preparation of 2-(2,4-dichlorobenzyl)-5-(4-fluorophenyl)-6-[4-(methylsulfinyl)phenyl]-2H-pyridazin-3-one Using 2-(2,4-dichlorobenzyl)-5-(4-fluorophenyl)-6-[4-(methylthio)phenyl]-2H-pyridazin-3-one as a starting material, the procedures of Example 85 were repeated likewise, whereby the title compound was obtained in a yield of 86.5%.

Colorless needles (ethyl acetate-hexane). Melting point: 214.4–214.5° C. $^1$H-NMR (CDCl$_3$) δ: 2.71(3H,s), 5.53(2H, s), 6.98(1H,s), 6.99–7.12(4H,m), 7.22–7.31(4H,m), 7.44 (1H,d,J=1.95 Hz), 7.54(2H,d,J=8.05 Hz). IR (KBr) cm$^{-1}$: 1668,1510,1235,1047,840,609.

Example 94

Preparation of 5-(4-chlorophenyl)-6-[4-(methylsulfinyl)phenyl]-2-(3-pyridylmethyl)-2H-pyridazin-3-one Using 5-(4-chlorophenyl)-6-(4-(methylthio)phenyl]-2-(3-pyridylmethyl)-2H-pyridazin-3-one as a starting material, the procedures of Example 85 were repeated likewise, whereby the title compound was obtained in a yield of 98.5%.

Colorless prisms (ethyl acetate-hexane). Melting point: 154.6–154.7° C. Mass (m/e): 435,437 (M$^+$). $^1$H-NMR (CDCl$_3$) δ: 2.74(3H,s), 5.45(2H,s), 6.96(1H,s), 7.03(2H,d,J=8.59 Hz), 7.23–7.34(5H,m), 7.57(2H,d,J=8.40 Hz), 7.89 (1H,tt,J=7.81,1.95 Hz), 8.58(1H,dd,J=4.88,1.66 Hz), 8.79 (1H,d,J=1.56 Hz). IR (KBr) cm$^{-1}$: 1664,1584,1494,1090, 1050,837.

Example 95

Preparation of 5-(4-fluorophenyl)-6-[4-(methylsulfinyl)phenyl]-2-(4-pyridylmethyl)-2H-pyridazin-3-one Using 5-(4-fluorophenyl)-6-[4-(methylthio)phenyl]-2-(4-pyridylmethyl)-2H-pyridazin-3-one as a starting material, the procedures of Example 85 were repeated likewise, whereby the title compound was obtained. The title compound was then converted into its methanesulfonate (yield: 88.1%).

Colorless needles (methanol-diethyl ether). Melting point: 212.8–218.5° C. (decomposed) $^1$H-NMR (CDCl$_3$–CD$_3$OD) δ: 2.45(3H,s), 2.69(3H,s), 5.73(2H,s), 7.06(1H,s), 7.08(2H,d,J=8.77 Hz), 7.14(4H,s), 7.25(2H,dd,J=8.79,5.12 Hz), 8.05(2H,d,J=6.10 Hz), 8.82(2H,d,J=6.83 Hz). IR (KBr) cm$^{-1}$: 1664,1601,1510,1210,1192,1050,843.

Example 96

Preparation of 2-(2,4-difluorocinnamyl)-5-(4-fluorophenyl)-6-[4-(methylsulfinyl)phenyl]-2H-pyridazin-3-one Using 2-(2,4-difluorocinnamyl)-5-(4-fluorophenyl)-6-[4-(methylthio)phenyl]-2H-pyridazin-3-one as a starting material, the procedures of Example 85 were repeated likewise, whereby the title compound was obtained in a yield of 58.1%.

Colorless amorphous. $^1$H-NMR (CDCl$_3$–CD$_3$OD) δ: 2.72 (3H,s), 5.03(2H,d,J=6.59 Hz), 6.49(1H,dt,J=15.87,6.65 Hz), 6.77–6.85(3H,m), 6.96(1H,s), 6.99–7.10(4H,m), 7.35(2H,d, J=8.30 Hz), 7.44(1H,dd,J=15.01,8.42 Hz), 7.56(2H,d,J=8.06 Hz). IR (KBr) cm$^{-1}$: 1665,1502,1274,1230,1050,966,841.

Example 97

Preparation of 2-benzyl-5-(4-chlorophenyl)-6-[4-(methylsulfonyl)phenyl]-2H-pyridazin-3-one 2-Benzyl-5-(4-chlorophenyl)-6-[4-(methylthio)phenyl]-2H-pyridazin-3-one (159.2 mg, 0.380 mmol) and sodium periodate (325.2 mg, 1.402 mmol) were dissolved in a mixed solvent of acetone (40 ml)-water (20 ml)-chloroform (5 ml). Under ice cooling, osmium tetraoxide/tert-butanol (1 g/25 ml) (0.24 ml) was added, and the mixture was stirred through the night until its temperature arose to room temperature. The reaction mixture was concentrated, and the residue was extracted with chloroform. The extract was dried over anhydrous sodium sulfate and then concentrated. The residue was separated and purified by silica gel preparative chromatography [hexane/ethyl acetate (1/1)], whereby the title compound (151.1 mg, 88.2%) was obtained.

Colorless crystalline powder (ethyl acetate-hexane) Melting point: 103.2–105.7° C. Mass (m/e): 450,452 (M$^+$). $^1$H-NMR (CDCl$_3$–CD$_3$OD) δ: 3.06(3H,s), 5.43(2H,s), 6.95 (1H,s), 7.01(2H,d,J=8.59 Hz), 7.30(2H,d,J=8.59 Hz), 7.33–7.41(5H,m), 7.49–7.55(2H,m), 7.84(2H,d,J=8.79 Hz). IR (KBr) cm$^{-1}$: 1668,1316,1153,1091,951.

Example 98

Preparation of 5-(4-chlorophenyl)-6-[4-(methylsulfonyl)phenyl]-2H-pyridazin-3-one Using 5-(4-chlorophenyl)-6-[4-(methylthio)phenyl]-2H-pyridazin-3-one as a starting material, the procedures of Example 97 were repeated likewise, whereby the title compound was obtained in a yield of 60.9%.

Colorless prisms (methylene chloride-methanol-hexane). Melting point: 254.0–254.7° C. Mass (m/e): 360,362 (M$^+$) $^1$H-NMR (CDCl$_3$) δ: 3.07(3H,s), 7.02(1H,s), 7.06(2H,d,J= 8.55 Hz), 7.33(2H,d,J=8.55 Hz), 7.42(2H,d,J=8.55 Hz), 7.86 (2H,d,J=8.55 Hz), 12.40(1H,brs). IR (KBr) cm$^{-1}$: 1661, 1587,1316,1153,1095.

Example 99

Preparation of 5-(4-chlorophenyl)-2-cyclopropylmethyl-6-[4-(methylsulfonyl)phenyl]-2H-pyridazin-3-one Using 5-(4-chlorophenyl)-2-cyclopropylmethyl-6-[4-(methylthio)phenyl]-2H-pyridazin-3-one as a starting material, the procedures of Example 97 were repeated likewise, whereby the title compound was obtained in a yield of 20.6%.

Colorless needles (ethyl acetate-hexane). Melting point: 139.7–139.8° C. Mass (m/e): 414,416 (M$^+$). $^1$H-NMR (CDCl$_3$) δ: 0.49–0.63(4H,m), 1.41–1.49(1H,m), 3.06(3H,s), 4.14(2H,d,J=7.22 Hz), 6.96(1H,s), 7.05(2H,d,J=8.59 Hz), 7.31(2H,d,J=8.59 Hz), 7.41(2H,d,J=8.59 Hz), 7.86(2H,d,J= 8.59 Hz). IR (KBr) cm$^{-1}$: 1664,1584,1313,1303,1151.

Example 100

Preparation of 2-cyclopropylmethyl-5-(4-fluorophenyl)-6-[4-(methylsulfonyl)phenyl]-2H-pyridazin-3-one Using 2-cyclopropylmethyl-5-(4-fluorophenyl)-6-[4-(methylthio)phenyl]-2H-pyridazin-3-one as a starting material, the procedures of Example 97 were repeated likewise, whereby the title compound was obtained in a yield of 87.1%.

Colorless prisms (ethyl acetate-hexane). Melting point: 123.8–123.9° C. Mass (m/e): 398 (M$^+$). $^1$H-NMR (CDCl$_3$) δ: 0.48–0.63(4H,m), 1.42–1.48(1H,m), 3.05(3H,s), 4.14(2H, d,J=7.42 Hz), 6.96(1H,s), 7.03(2H,t,J=8.50 Hz), 7.08–7.11 (2H,m), 7.40(2H,d,J=8.40 Hz), 7.85(2H,d,J=8.20 Hz).

IR (KBr) cm$^{-1}$: 1664,1511,1316,1229,1153,954,852,613.

Example 101

Preparation of 2-benzyl-5-(4-fluorophenyl)-6-[4-(methylsulfonyl)phenyl]-2H-pyridazin-3-one Using 2-benzyl-5-(4-fluorophenyl)-6-[4-(methylthio) phenyl]-2H-pyridazin-3-one as a starting material, the procedures of Example 97 were repeated likewise, whereby the title compound was obtained in a yield of 99.0%.

Pale yellow needles (ethyl acetate-hexane). Melting point: 187.6–188.0° C. $^1$H-NMR (CDCl$_3$) δ: 3.05(3H,s), 5.43(2H, s), 6.95(1H,s), 7.01–7.07(4H,m), 7.33–7.40(5H,m), 7.53

(2H,dd,J=7.69,1.83 Hz), 7.84(2H,d,J=8.55 Hz). IR (KBr) cm$^{-1}$: 1668,1595,1582,1510,1313,1154,955,849, 779.

Example 102

Preparation of 5-(4-fluorophenyl)-2-(4-methoxybenzyl)-6-[4-(methylsulfonyl)phenyl]-2H-pyridazin-3-one Using 5-(4-fluorophenyl)-2-(4-methoxybenzyl)- 6-[4-(methylthio)phenyl]-2H-pyridazin-3-one as a starting material, the procedures of Example 97 were repeated likewise, whereby the title compound was obtained in a yield of 99.0%.

Colorless amorphous. Mass (m/e): 464 (M$^+$). $^1$H-NMR (CDCl$_3$) δ: 3.05(3H,s), 3.80(3H,s), 5.37(2H,s), 6.89(2H,d, J=8.01 Hz), 6.93(1H,s), 7.01–7.05(4H,m), 7.36(2H,d,J=8.20 Hz), 7.48(2H,d,J=8.01 Hz), 7.83(2H,d,J=8.01 Hz). IR (KBr) cm$^{-1}$: 1668,1512,1315,1248,1153,842.

Example 103

Preparation of 2-(2,4-difluorobenzyl)-5-(4-chlorophenyl)-6-[4-(methylsulfonyl)phenyl]-2H-pyridazin-3-one Using 2-(2,4-difluorobenzyl)-5-(4-chlorophenyl)-6-[4-(methylthio)phenyl]-2H-pyridazin-3-one as a starting material, the procedures of Example 97 were repeated likewise, whereby the title compound was obtained in a yield of 94.5%.

Colorless needles (ethyl acetate-hexane). Melting point: 173.8–173.9° C. Mass (m/e): 486,488 (M$^+$). $^1$H-NMR (CDCl$_3$) δ: 3.05(3H,s), 5.46(2H,s), 6.83–6.90(2H,m), 6.96 (1H,s), 7.03(2H,d,J=8.40 Hz), 7.31(2H,d,J=8.40 Hz), 7.35 (2H,d,J=8.20 Hz), 7.48–7.54(1H,m), 7.84(2H,d,J=8.20 Hz). IR (KBr) cm$^{-1}$: 1668,1507,1316,1153,1093,972,837.

Example 104

Preparation of 5-(4-chlorophenyl)-2-(2,4-dichlorobenzyl)-6-[4-(methylsulfonyl)phenyl]-2H-pyridazin-3-one Using 5-(4-chlorophenyl)-2-(2,4-dichlorobenzyl)-6-[4-(methylthio)phenyl]-2H-pyridazin-3-one as a starting material, the procedures of Example 97 were repeated likewise, whereby the title compound was obtained in a yield of 53.3%.

Colorless scales (chloroform-hexane). Melting point: 232.7–234.5° C. Mass (m/e): 518,520 (M$^+$). $^1$H-NMR (CDCl$_3$) δ: 3.05(3H,s), 5.54(2H,s), 6.99(1H,s), 7.03(2H,d, J=8.30 Hz), 7.25(1H,dd,J=8.30,2.12 Hz), 7.28–7.40(5H,m), 7.45(1H,d,J=2.12 Hz), 7.83(2H,d,J=8.30 Hz). IR (KBr) cm$^{-1}$: 1665,1324,1314,1158,1093.

Example 105

Preparation of 2-(2,4-dichlorobenzyl)-5-(4-fluorophenyl)-6-(4-(methylsulfonyl)phenyl]-2H-pyridazin-3-one Using 2-(2,4-dichlorobenzyl)-5-( 4-fluorophenyl)-6-[4-(methylthio)phenyl]-2H-pyridazin-3-one as a starting material, the procedures of Example 97 were repeated likewise, whereby the title compound was obtained in a yield of 10.3%.

Colorless needles (ethyl acetate-hexane) Melting point: 211.8–212.2° C. $^1$H-NMR (CDCl$_3$) δ: 3.04(3H,s), 5.54(2H, s), 6.99(1H,s), 7.01–7.11(4H,m), 7.23–7.35(5H,m), 7.45 (1H,d,J=2.20 Hz), 7.82(2H,d,J=6.59 Hz). IR (KBr) cm$^{-1}$: 1669,1590,1510,1314,1236,1156,954,842, 554.

Example 106

Preparation of 5-(4-chlorophenyl)-6-[4-(methylsulfonyl)phenyl]-2-(3-pyridylmethyl)-2H-pyridazin-3-one Using 5-(4-chlorophenyl)-6-[4-(methylthio)phenyl]-2-(3-pyridylmethyl)-2H-pyridazin-3-one as a starting material, the procedures of Example 97 were repeated likewise, whereby the title compound was obtained in a yield of 57.5%.

Colorless crystalline powder (ethyl acetate-hexane) Melting point: 248.0–248.1° C. Mass (m/e): 451 (M$^+$). $^1$H-NMR (CDCl$_3$) δ: 3.08(3H,s), 5.37(2H,s), 6.98(1H,s), 7.03(2H,d, J=8.40 Hz), 7.30–7.33(1H,m), 7.32(2H,d,J=8.40 Hz), 7.49 (1H,d,J=7.81 Hz), 7.86(2H,d,J=8.40 Hz), 8.17(2H,d,J=6.44 Hz), 8.34(1H,s). IR (KBr) cm$^{-1}$: 1664,1555,1314,1278, 1153,1091.

Example 107

Preparation of 5-(4-fluorophenyl)-6-[4-(methylsulfonyl)phenyl]-2-(4-pyridylmethyl)-2H-pyridazin-3-one Using 5-(4-fluorophenyl)-6-[4-(methylthio)phenyl]-2-(4-pyridylmethyl)-2H-pyridazin-3-one as a starting material, the procedures of Example 97 were repeated likewise, whereby the title compound was obtained in a yield of 89.1%.

Pale yellow prisms (ethyl acetate-hexane) Melting point: 253.3–254.5° C. Mass (m/e): 435 (M$^+$). $^1$H-NMR (CDCl$_3$) δ: 3.05(3H,s), 5.42(2H,d,J=4.15 Hz), 7.00(1H,s), 7.03–7.10 (4H,m), 7.35–7.38(4H,m), 7.85(2H,d,J=8.30 Hz), 8.61(2H, d,J=5.81 Hz). IR (KBr) cm$^{-1}$: 1666,1602,1582,1511,1315, 1237,1154,944, 848.

Example 108

Preparation of 5-(4-chlorophenyl)-6-[4-(methylsulfonyl)phenyl]-2-(3-phenylpropyl)-2H-pyridazin-3-one Using 5-(4-chlorophenyl)-6-[4-(methylthio)phenyl]-2-(3-phenylpropyl)-2H-pyridazin-3-one as a starting material, the procedures of Example 97 were repeated likewise, whereby the title compound was obtained in a yield of 72.5%.

Colorless crystalline powder (ethyl acetate-hexane) Melting point: 70.2–71.6° C. Mass (m/e): 478,480 (M$^+$). $^1$H-NMR (CDCl$_3$) δ: 2.26(2H,q,J=7.45 Hz), 2.77(2H,t,J= 7.45 Hz), 3.06(3H,s), 4.34(2H,t,J=7.45 Hz), 6.91(1H,s), 7.02(2H,d,J=8.79 Hz), 7.14–7.33(7H,m), 7.38(2H,d,J=8.54 Hz), 7.85(2H,d,J=8.54 Hz). IR (KBr) cm$^{-1}$: 1664,1584, 1494,1314,1152,1091,835,540.

Example 109

Preparation of 2-benzyl-6-[4-(methylsulfonyl)phenyl]-5-phenyl-2H-pyridazin-3-one Using 2-benzyl-6-[4-(methylthio)phenyl]-5-phenyl-2H-pyridazin-3-one as a starting material, the procedures of Example 97 were repeated likewise, whereby the title compound was obtained in a yield of 72.4%.

Colorless needles (chloroform-hexane) Melting point: 211.0–212.0° C. Mass (m/e): 416,418 (M$^+$). $^1$H-NMR (CDCl$_3$) δ: 3.04(3H,s), 5.44(2H,s), 6.97(1H,s), 7.04–7.09 (2H,m), 7.24–7.41(8H,m), 7.50–7.56(2H,m), 7.81(2H,d,J= 8.54 Hz). IR (KBr) cm$^{-1}$: 1663,1590,1497,1320,1311,1304, 1154,957, 779,720,707.

Example 110

Preparation of 2-(4-aminobenzyl)-5,6-bis(4-methoxyphenyl)-2H-pyridazin-3-one

10% palladium on charcoal (200 mg) was added to a solution of 5,6-bis(4-methoxyphenyl)-2-(4-nitrobenzyl)-2H-pyridazin-3-one (300 mg, 0.68 mmol) in ethyl acetate (30 ml), followed by catalytic reduction at room temperature and atmospheric pressure. Ninety minutes later, the reaction mixture was filtered. After the catalyst was washed with ethyl acetate, the filtrate and the washing were combined. The solvent was distilled off, whereby a pale yellow oil (253 mg) was obtained. The oil (253 mg) was separated and purified by silica gel preparative chromatography [developer: chloroform/methanol (20/1)], whereby the title compound (250 mg, 89.2%) was obtained as pale yellow amorphous. $^1$H-NMR (CDCl$_3$) δ: 3.70(2H,brs), 3.79(6H,s), 5.29(2H,d,J=8.30 Hz), 6.77(2H,d,J=9.03 Hz), 6.79(2H,d,J= 8.79 Hz), 6.85(1H,s), 7.00(2H,d,J=9.03 Hz), 7.10(2H,d,J= 8.79 Hz), 7.37(2H,d,J=8.54 Hz). Melting point: 171.0–173.0° C. (decomposed) IR (KBr) cm$^{-1}$: 3668,3419, 2906,2835,1641,1606,1510,1257, 1176,1025,834.

Example 111

Preparation of 5,6-bis(4-methoxyphenyl)-2-[4-(dimethylamino)benzyl]-2H-pyridazin-3-one and 5,6-bis(4-methoxyphenyl)-2-[4-(methylamino)benzyl]-2H-pyridazin-3-one To a solution of 2-(4-aminobenzyl)-5,6-bis(4-methoxyphenyl)-2H-pyridazin-3-one (245 mg, 0.6 mmol) in acetone/N,N-dimethylformamide (5/1) (6 ml), sodium hydrogencarbonate (378 mg, 4.5 mmol) and a solution of dimethyl sulfate in acetone [an acetone solution of dimethyl sulfate (631 mg) (total volume: 5 ml); 3.0 ml, 3.0 mmol)] was added, followed by stirring under heat at 60° C. for 90 minutes. After the acetone was distilled off, the residue was extracted with ethyl acetate. The organic layer was washed successively with water and a brine, and was then dried over anhydrous sodium sulfate. The solvent was distilled off. The pale orange oil (238 mg) was separated and purified by silica gel preparative chromatography [developer: chloroform/ methanol (20/1)], whereby 5,6-bis(4-methoxyphenyl)-2-[4-(dimethylamino)benzyl]-2H-pyridazin-3-one (80.6 mg, 30.8%) was obtained as a reddish brown oil from fractions having large Rf values. $^1$H-NMR (CDCl$_3$) δ: 2.94(6H,s), 3.79(6H,s), 5.32(2H,s), 6.71(2H,d,J=8.79 Hz), 6.78(2H,d,J= 8.79 Hz), 6.79(2H,d,J=9.03 Hz), 6.85(1H,s), 7.07(2H,d,J= 8.79 Hz), 7.11(2H,d,J=9.03 Hz), 7.48(2H,d,J=8.79 Hz).

In a manner known per se in the art, the hydrochloride of 5,6-bis(4-methoxyphenyl)-2-[4-(dimethylamino)benzyl]-2H-pyridazin-3-one was obtained in a yield of 67.7%.

Yellow needles (methanol-diethyl ether). Melting point: 122–126° C. $^1$H-NMR (DMSO-D$_6$+D$_2$O) δ: 3.06(6H,s), 3.74 (3H,s), 3.75(3H,s), 5.33(2H,s), 6.86(2H,d,J=8.79 Hz), 6.89 (2H,d,J=8.30 Hz), 6.91(1H,s), 7.11(4H,d,J=8.79 Hz), 7.30 (2H,d,J=8.79 Hz), 7.46(2H,d,J=8.79 Hz). IR (KBr) cm$^{-1}$: 3668,3383,1655,1609,1513,1298,1247,1182, 1174,837,827.

From fractions having small Rf values, 5,6-bis(4-methoxyphenyl)-2-[4-(methylamino)benzyl]-2H-pyridazin-3-one (47.4 mg, 18.7%) was obtained as a pale brown oil.

$^1$H-NMR (CDCl$_3$) δ: 2.82(3H,s), 3.79(6H,s), 5.30(2H,s), 6.58(2H,d,J=8.54 Hz), 6.77(2H,d,J=9.03 Hz), 6.79(2H,d,J= 8.79 Hz), 6.85(1H,s), 7.00(2H,d,J=8.79 Hz), 7.11(2H,d,J= 8.78 Hz), 7.42(2H,d,J=8.54 Hz). IR (film) cm$^{-1}$: 3410,3373, 1652,1610,1515,1296,1249, 1181,1029,833,754.

Example 112

Preparation of 5,6-bis(4-methoxyphenyl)-2-(4-carboxybenzyl)-2H-pyridazin-3-one

To a solution of 5,6-bis(4-methoxyphenyl)-2-(4-methoxycarbonylbenzyl)-2H-pyridazin-3-one (168 mg, 0.37 mmol) in methanol (4 ml), a 1 N aqueous solution of sodium hydroxide (1.84 ml) was added, followed by stirring under heat at 40° C. for 4 hours. The methanol was distilled off, and to the residue, a 2 N aqueous solution of hydrochloric acid was added to acidify the residue (pH<1). The thus-acidified mixture was extracted with ethyl acetate. The organic layer was washed successively with water and a brine, and was then dried over anhydrous sodium sulfate. The solvent was distilled off and the thus-obtained residue (161 mg) was recrystallized from chloroform-methanol, whereby the title compound (138 mg, 84.7%) was obtained as colorless needles.

Melting point: 241.0–242.0° C. Mass (m/e): 442 (M$^+$). $^1$H-NMR (CDCl$_3$) δ: 3.79(3H,s), 3.80(3H,s), 5.48(2H,s), 6.78(2H,d,J=8.79 Hz), 6.80(2H,d,J=8.79 Hz), 6.93(1H,s), 7.04(2H,d,J=8.79 Hz), 7.10(2H,d,J=8.79 Hz), 7.59(2H,d,J= 8.55 Hz), 8.08(2H,d,J=8.30 Hz). IR (KBr) cm$^{-1}$: 1706,1632, 1611,1553,1254,1180,1025,829.

Example 113

Preparation of 5,6-bis(4-methoxyphenyl)-2-[2-(4-methylpiperadinocarbonyl)ethyl]-2H-pyridazin-3-one (1) Preparation of 5,6-bis(4-methoxyphenyl)-2-(2-ethoxycarbonylethyl)-2H-pyridazin-3-one:

To a solution of 5,6-bis(4-methoxyphenyl)-2H-pyridazin-3-one (308 mg, 1 mmol) in N,N-dimethylformamide (3 ml), potassium carbonate (276 mg, 2 mmol) and ethyl 3-chloropropionate (273 mg, 2 mmol) were added, followed by stirring at 80° C. for 16 hours. After the reaction mixture was allowed to cool down, water was added to the reaction mixture and the mixture was extracted with ethyl acetate. The organic layer was washed successively with water and a brine, and was then dried over anhydrous sodium sulfate. The solvent was distilled off and the residue (416 mg) was separated and purified by chromatography on a silica gel column [silica gel: 11 g, chloroform/ methanol (20/1)], whereby the title compound (390 mg, 97%) was obtained as a pale yellow oil.

$^1$H-NMR (CDCl$_3$) δ: 1.22(3H,t,J=7.08 Hz), 2.91(2H,t,J= 7.32 Hz), 3.79(3H,s), 3.81(3H,s), 4.14(2H,q,J=7.08 Hz), 4.55(2H,t,J=7.32 Hz), 6.78(2H,d,J=8.79 Hz), 6.81(2H,d,J= 8.79 Hz), 6.88(1H,s), 7.04(2H,d,J=8.79 Hz), 7.11(2H,d,J= 8.79 Hz). IR (KBr) cm$^{-1}$: 1733,1659,1607,1515,1297,1250, 1179, 1029,845.

(2) Preparation of 5,6-bis(4-methoxyphenyl)-2-(2-carboxyethyl)-2H-pyridazin-3-one:

A 2 N aqueous solution of sodium hydroxide was added to a solution of 5,6-bis(4-methoxyphenyl)-2-(2-ethoxycarbonylethyl)-2H-pyridazin-3-one (390 mg, 0.97 mmol) in methanol (7 ml). The mixture was heated to dissolve precipitated crystals, followed by stirring at room temperature for 25 hours. After the methanol was distilled off, the residue was dissolved in water. A 2 N aqueous solution of hydrochloric acid was added to the resulting mixture to acidify the same. The mixture was extracted with ethyl acetate. The organic layer was washed successively with water and a brine, and was then dried over anhydrous sodium sulfate. The solvent was distilled off, and the residue (377 mg) was separated and purified by chromatography on a silica gel column [silica gel: 2 g, chloroform/methanol (10/1)], whereby the title compound (356 mg, 96.5%) was obtained as a pale yellow amorphous.

Mass (m/e): 380 (M$^+$). $^1$H-NMR (CDCl$_3$) δ: 2.97(2H,t, J=7.08 Hz), 3.78(3H,s), 3.80(3H,s), 4.57(2H,t,J=7.08 Hz), 6.77(2H,d,J=8.79 Hz), 6.80(2H,d,J=8.79 Hz), 6.93(1H,s), 7.03(2H,d,J=8.79 Hz), 7.11(2H,d,J=8.79 Hz). IR (KBr) cm$^{-1}$: 3427,1637,1609,1511,1297,1249,1178,834.

(3) Preparation of 5,6-bis(4-methoxyphenyl)-2-[2-(4-methylpiperadinocarbonyl)ethyl]-2H-pyridazin-3-one:

To a solution of 5,6-bis(4-methoxyphenyl)-2-(2-carboxyethyl)-2H-pyridazin-3-one (266 mg, 0.7 mmol) in tetrahydrofuran (1.3 ml), oxalyl chloride (133 mg, 1.5 eq) was gradually added dropwise under ice cooling. The mixture was stirred at room temperature for 90 minutes. A solution of triethylamine (283 mg, 4.0 eq) and N-methylpiperazine (102 mg, 1.5 eq) in tetrahydrofuran (2 ml) was then added, followed by stirring at room temperature for 4 hours. The tetrahydrofuran was distilled off and the residue was extracted with ethyl acetate. The organic layer was washed successively with a saturated aqueous solution of sodium hydrogencarbonate, water and a brine, and was then dried over anhydrous sodium sulfate. The solvent was distilled off, and the residue (293 mg) was separated and purified by chromatography on a silica gel column [silica gel: 9 g, chloroform/methanol (50/1)], whereby the title compound (272 mg, 84.0%) was obtained as a pale yellow amorphous.

Mass (m/e): 462 (M$^+$). $^1$H-NMR (CDCl$_3$) δ: 2.28(3H,s), 2.36–2.38(4H,m), 2.94(2H,t,J=7.81 Hz), 3.48–3.52(2H,m), 3.63–3.66(2H,m), 3.79(3H,s), 3.81(3H,s), 4.56(2H,t,J=7.81 Hz), 6.78(2H,d,J=9.04 Hz), 6.81(2H,d,J=7.89 Hz), 6.88(1H, s), 7.04(2H,d,J=8.79 Hz), 7.12(2H,d,J=8.78 Hz). IR (KBr) cm$^{-1}$: 1652,1609,1513,1460,1259,1249,1175,1028, 834.

Example 114

Preparation of 5,6-bis(4-methoxyphenyl)-2-(4-methylpiperazinocarbonylmethyl)-2H-pyridazin-3-one After 5,6-bis(4-methoxyphenyl)-2-carboxymethyl)-2H-pyridazin-3-one (Eur. J. Med. Chem., 14, 53, 1979) was reacted with oxalyl chloride in a similar manner as in Example 113-(3), a further reaction was conducted with 4-methylpiperazine, whereby the title compound was obtained in a yield of 20.7%.

Orange amorphous. $^1$H-NMR (CDCl$_3$) δ: 2.30(3H,s), 2.45(4H,m), 3.66–3.71(4H,m), 3.79(3H,s), 3.81(3H,s), 5.32 (2H,s), 6.78(2H,d,J=8.79 Hz), 6.82(2H,d,J=8.79 Hz), 6.90 (1H,s), 7.06(2H,d,J=8.79 Hz), 7.13(2H,d,J=8.79 Hz). IR (KBr) cm$^{-1}$: 1659,1609,1513,1463,1294,1259,1176,1028, 834.

Example 115

Preparation of 5,6-bis(4-methoxyphenyl)-2-[2-(benzylaminocarbonyl)ethyl]-2H-pyridazin-3-one After 5,6-bis(4-methoxyphenyl)-2-(2-carboxyethyl)-2H-pyridazin-3-one was reacted with oxalyl chloride in a similar manner as in Example 113-(3), a further reaction was conducted with benzylamine, whereby the title compound was obtained in a yield of 52.2%.

Colorless fine needles (ethyl acetate-hexane). Melting point: 135.0–137.0° C. Mass (m/e): 469 (M$^+$). $^1$H-NMR (CDCl$_3$) δ: 2.88(2H,t,J=6.83 Hz), 3.79(3H,s), 3.81(3H,s), 4.43(2H,d,J=5.85 Hz), 4.57(2H,t,J=6.83 Hz), 6.71(1H,m), 6.76(2H,d,J=8.79 Hz), 6.81(2H,d,J=8.79 Hz), 6.85(1H,s), 7.01(2H,d,J=8.79 Hz), 7.10(2H,d,J=8.79 Hz), 7.24–7.38 (5H,m). IR (KBr) cm$^{-1}$: 3434,3297,1642,1609,1510,1247, 1177,1029, 831.

Example 116

Preparation of 5,6-bis(4-methoxyphenyl)-2-[2-(4-methylpiperazino)ethyl]-2H-pyridazin-3-one (1) Preparation of 5,6-bis(4-methoxyphenyl)-2-(2-hydroxyethyl)-2H-pyridazin-3-one:

To a solution of 5,6-bis(4-methoxyphenyl)-2H-pyridazin-3-one (154 mg, 0.5 mmol) in N,N-dimethylformamide (0.03 ml), tetraethylammonium iodide (413 mg, 1.5 mmol) and ethylene carbonate (132 mg, 1.5 mmol) were added, followed by stirring at 145–150° C. for 2 hours. After the reaction mixture was allowed to cool down, water was added to the reaction mixture and the mixture was extracted with ethyl acetate. The organic layer was washed successively with water and a brine, and was then dried over anhydrous sodium sulfate. The solvent was distilled off and the residue (100 mg) was separated and purified twice by chromatography on a silica gel column (silica gel: 4 g, ethyl acetate), whereby the title compound (165 mg, 94%) was obtained as a pale brown oil.

$^1$H-NMR (CDCl$_3$) δ: 3.58(1H,t,J=5.86 Hz), 3.80(3H,s), 3.81(3H,s), 4.05–4.15(2H,m), 4.48(2H,dd,J=4.88,4.88 Hz), 6.79(2H,d,J=8.79 Hz), 6.82(2H,d,J=8.79 Hz), 6.94(1H,s), 7.05(2H,d,J=8.79 Hz), 7.12(2H,d,J=9.28 Hz).

(2) Preparation of 5,6-bis(4-methoxyphenyl)-2-[2-(4-methylpiperazino)ethyl]-2H-pyridazin-3-one:

To a solution of para-toluenesulfonyl chloride (357 mg, 4 eq) in pyridine (0.5 ml), a solution of 5,6-bis(4-methoxyphenyl)-2-(2-hydroxyethyl)-2H-pyridazin-3-one (165 mg, 0.47 mmol) in pyridine (1.0 ml) was added, followed by stirring at room temperature for 2 hours. The reaction mixture was poured into ice water, followed by extraction with ethyl acetate. The organic layer was washed successively with water and a brine, and was then dried over anhydrous sodium sulfate. The solvent was distilled off, and N-methylpiperazine (0.15 ml, 3 eq) was added to the residue. The resulting mixture was stirred at 90–100° C. for 2 hours. After water was added to the reaction mixture, the mixture was extracted with ethyl acetate. The organic layer was washed successively with water and a brine, and then dried over anhydrous sodium sulfate. The solvent was distilled off, and ethanol was added to the residue. The resulting mixture was azeotropically boiled three times with ethanol to drive off water. The thus-obtained residue (256 mg) was separated and purified by chromatography on a silica gel column [silica gel: 8 g, chloroform/methanol (20/1)], whereby a yellow oil (165 mg, 81%) was obtained. The oil was left over in a refrigerator. Precipitated crystals were washed with a mixed solvent of methanol and diethyl ether, whereby the title compound (65 mg, 32%) was obtained as pale yellow prisms. Melting point: 109.7–110.8° C. $^1$H-NMR (CDCl$_3$) δ: 2.29(3H,s), 2.46(4H,brs), 2.64(4H, brs), 2.87(2H,t,J=6.83 Hz), 3.80(3H,s), 3.81(3H,s), 4.40(2H, t,J=6.84 Hz), 6.79(2H,d,J=9.03 Hz), 6.81(2H,d,J=8.78 Hz), 6.87(1H,s), 7.02(2H,d,J=8.79 Hz), 7.12(2H,d,J=9.03 Hz). IR (KBr) cm$^{-1}$: 1659,1608,1513,1295,1250,1177,1013.

Example 117

Preparation of 5,6-bis(4-methoxyphenyl)-2-[2-(morpholino)ethyl]-2H-pyridazin-3-one After 5,6-bis(4-methoxyphenyl)-2-(2-hydroxyethyl)-2H-pyridazin-3-one was reacted with paratoluenesulfonyl chloride in a similar manner as in Example 116-(2), a further reaction was conducted with morpholine, whereby the title compound was obtained in a yield of 42.6%.

Pale yellow needles (methanol-diethyl ether). Melting point: 145.1–145.8° C. $^1$H-NMR (CDCl$_3$) δ: 2.59(4H,t,J=4.64 Hz), 2.86(2H,t,J=6.83 Hz), 3.75(4H,t,J=4.64 Hz), 3.81(3H,s), 3.81(3H,s), 4.40(2H,t,J=7.08 Hz), 6.79(2H,d,J=8.79 Hz), 6.81(2H,d,J=8.79 Hz), 6.88(1H,s), 7.05(2H,d,J=8.79 Hz), 7.12(2H,d,J=8.78 Hz). IR (KBr) cm$^{-1}$: 1664,1608, 1513,1247,1181,1119,834.

Example 118

Preparation of 5,6-bis(4-methoxyphenyl)-2-[2-(piperidino)ethyl]-2H-pyridazin-3-one After 5,6-bis(4-methoxyphenyl)-2-(2-hydroxyethyl)-2H-pyridazin-3-one was reacted with paratoluenesulfonyl chloride in a similar manner as in Example 116-(2), a further reaction was conducted with piperidine, whereby the title compound was obtained in a yield of 38.1%.

Yellow oil. Mass (m/e): 419 (M$^+$). $^1$H-NMR (CDCl$_3$) δ: 1.44–1.46(2H,m), 1.56–1.64(4H,m), 2.52–2.56(4H,m), 2.84 (2H,t,J=7.33 Hz), 3.79(3H,s), 3.80(3H,s), 4.40(2H,t,J=7.33 Hz), 6.78(2H,d,J=8.79 Hz), 6.81(2H,d,J=8.30 Hz), 6.87(1H, s), 7.04(2H,d,J=8.79 Hz), 7.13(2H,d,J=8.79 Hz). IR (film) cm$^{-1}$: 1660,1609,1514,1296,1250,1177,1033,834.

Example 119

Preparation of 5,6-bis(4-methoxyphenyl)-2-(3-piperidylmethyl)-2H-pyridazin-3-one (1) Preparation of 3-(hydroxymethyl)-1-(tert-butoxycarbonyl)piperidine:

Triethylamine (2.8 ml, 20 mmol) was added to a solution of 3-(hydroxymethyl)piperidine (1.15 g, 10 mmol) in tetrahydrofuran (15 ml), followed by the addition of a solution of di-tert-butyl carbonate (2.62 g, 10 mmol) in tetrahydrofuran (5 ml) at room temperature under stirring. The mixture was stirred at room temperature for 20 hours. The solvent was distilled off, and the residue was dissolved in ethyl acetate (50 ml). The solution was washed successively with water and a brine, and was then dried over anhydrous sodium sulfate. The solvent was then distilled off, whereby the title compound (2.15 g, 100%) was obtained as colorless crystals.

$^1$H-NMR (CDCl$_3$) δ: 1.2–1.4(2H,m), 1.46(9H,s), 1.5–1.9 (4H,m), 2.8–3.3(2H,m), 3.51(2H,t,J=6.10 Hz), 3.6–3.9(2H, m). IR (KBr) cm$^{-1}$: 3491,1742,1674,1428,1269,1177,1153, 858, 769.

(2) Preparation of 1-(tert-butoxycarbonyl)-3-(tosyloxymethyl)piperidine:

To a solution of 3-(hydroxymethyl)-1-(tert-butoxycarbonyl)piperidine (200 mg, 0.9 mmol) in anhydrous pyridine (4 ml), para-toluenesulfonic acid (890 mg) was added in small portions while stirring the solution under cooling with ice water. Five minutes later, the resultant mixture was heated to room temperature, at which stirring was continued for 2 hours. The reaction mixture was poured into ice water, followed by extraction with ethyl acetate. The organic layer was washed successively with water and a brine, and was then dried over anhydrous sodium sulfate. The solvent was distilled off, whereby the title compound (343 mg, 100%) was obtained as a colorless oil.

$^1$H-NMR (CDCl$_3$) δ: 1.1–1.3(2H,m), 1.44(9H,m), 1.4–1.9 (2H,m), 2.46(3H,s), 2.7–2.9(1H,m), 3.8–4.1(4H,m), 3.89 (2H,d,J=6.11 Hz), 7.35(2H,d,J=8.54 Hz), 7.78(2H,d,J=8.30 Hz).

(3) Preparation of 5,6-bis(4-methoxyphenyl)-2-[3-(1-tert-butoxycarbonyl)piperidyl)methyl]-2H-pyridazin-3-one:

To a solution of 1-(tert-butoxycarbonyl)-3-(tosyloxymethyl)piperidine (200 mg, 0.65 mmol) in N,N-dimethylformamide (4 ml), 5,6-bis(4-methoxyphenyl)-2H-pyridazin-3-one (343 mg, 0.93 mmol) and potassium carbonate (276 mg, 2.0 mmol) were added, followed by stirring at 80° C. for 8 hours. After the reaction mixture was allowed to cool down, water was added to the reaction mixture. The mixture was extracted with ethyl acetate. The organic layer was washed successively with water (twice) and a brine, and was then dried over anhydrous sodium sulfate. The solvent was distilled off and the resulting reddish brown oil (405 mg) was then purified by silica gel preparative chromatography [chloroform/methanol (20/1)], whereby the title compound (383 mg, quantitative) was obtained as a pale brown oil.

$^1$H-NMR (CDCl$_3$) δ: 1.20–1.40(2H,m), 1.41(9H,s), 1.60–1.90(2H,m), 2.15–2.35(1H,m), 2.65–2.90(2H,m), 3.80 (3H,s), 3.81(3H,s), 3.85–4.25(4H,m), 6.79(2H,d,J=8.79 Hz), 6.80(2H,d,J=8.78 Hz), 7.04(2H,d,J=8.79 Hz), 7.13(2H, d,J=8.79 Hz).

(4) Preparation of 5,6-bis(4-methoxyphenyl)-2-(3-piperidylmethyl)-2H-pyridazin-3-one:

A 6 N aqueous solution of hydrochloric acid (0.2 ml, 1.2 mmol) was added to a solution of 5,6-bis(4-methoxyphenyl)-2-[3-(1-tert-butoxycarbonyl)piperidyl) methyl]-2H-pyridazin-3-one (69 mg; content: 59 mg, 0.12 mmol) in tetrahydrofuran (2 ml), followed by stirring at 70° C. for 1 hour. After the reaction mixture was allowed to cool down, the solvent was distilled off and ethanol was added to the residue. The thus-obtained mixture was azeotropically boiled three times with ethanol to drive off water. The residue (oil, 94 mg) was separated and purified by silica gel preparative chromatography [chloroform/methanol (with 10% (W/W) ammonia) (30:1)], whereby the title compound (46 mg, 97.0%) was obtained as a pale yellow oil. $^1$H-NMR (CDCl$_3$) δ: 1.20–1.40(1H,m), 1.40–1.58(1H,m), 1.65–1.80 (1H,m), 2.10–2.20(1H,m), 2.45–2.68(2H,m), 2.94–3.12(2H, m), 3.79(3H,s), 3.81(3H,s), 4.04–5.04(2H,m), 6.78(2H,d,J= 8.79 Hz), 6.81(2H,d,J=8.79 Hz), 6.88(1H,s), 7.04(2H,d,J= 8.54 Hz), 7.12(2H,d,J=8.55 Hz). IR (KBr) cm$^{-1}$: 3313,3003, 2935,2840,1668,1652,1609,1296, 1251,1178,1030,834.

Example 120

Preparation of 5,6-bis(4-methoxyphenyl)-2-[3-(1-methylpiperidyl)methyl]-2H-pyridazin-3-one To a solution of 5,6-bis(4-methoxyphenyl)-2-(3-piperidylmethyl)-2H-pyridazin-3-one (203 mg, 0.5 mmol) in acetone/dimethyl sulfoxide (5/1) (6 ml), an acetone solution of dimethyl sulfate (631 mg was dissolved with acetone into a solution of 5 ml in total volume) (1.0 ml, 1.0 mmol) was added, followed by stirring at 60° C. for 2 hours. After the reaction mixture was allowed to cool down, water was added to the reaction mixture. The mixture was extracted with ethyl acetate. The organic layer was washed successively with water and a brine and was then dried over anhydrous sodium sulfate. The solvent was distilled off and the residue (oil, 115 mg) was separated and purified by silica gel preparative chromatography [chloroform/methanol [with 10% (W/W) ammonia, (15:1)], whereby the title compound (63.2 mg, 30.0%) was obtained as a pale yellow oil. $^1$H-NMR (CDCl$_3$) δ: 1.50–2.00(6H,m), 2.27(3H,s), 2.25–2.42(1H,m), 2.73–2.87(2H,m), 3.80(3H,s), 3.81(3H,s), 4.10(1H,dd,J=6.35,12.69 Hz), 4.21(1H,dd,J=7.81,12.69 Hz), 6.79(2H,d,J=8.79 Hz), 6.81(2H,d,J=8.55 Hz), 6.88(1H, s), 7.05(2H,d,J=8.79 Hz), 7.12(2H,d,J=9.03 Hz). IR (film) cm$^{-1}$: 1652,1610,1514,1464,1295,1248,1176, 1029,833, 754.

Example 121

Preparation of 2-benzyl-5-(4-chlorophenyl)-4,5-dihydro-6-[4-(methylthio)phenyl]-2H-pyridazin-3-one Methyl 3-(4-chlorophenyl)-4-[4-(methylthio)phenyl]-4-oxobutanoate (525 mg, 1.505 mmol), benzyl hydrazine dihydrochloride (262.6 mg, 1.655 mmol) and sodium acetate (467.4 mg, 4.966 mmol) were dissolved in 85% ethanol (6 ml), followed by heating under reflux for 2 days. The reaction mixture was concentrated, to which a 2 N aqueous solution of hydrochloric acid was added. The mixture was extracted with chloroform. The extract was washed with water and then dried over anhydrous sodium sulfate. The solvent was distilled off and the thus-obtained residue was separated and purified by silica gel preparative chromatography [hexane/ethyl acetate (2/1)], whereby the title compound (290.3 mg, 45.8%) was obtained.

Colorless prisms (ethyl acetate-hexane) Melting point: 113.5–113.9° C. Mass (m/e): 420,422 (M$^+$). $^1$H-NMR (CDCl$_3$) δ: 2.33(3H,s), 2.68(1H,d,J=16.47 Hz), 2.86(1H,dd, J=7.42,16.47 Hz), 4.28(1H,d,J=7.42 Hz), 4.75(1H,d,14.06 Hz), 5.29(1H,d,14.06 Hz), 6.79(2H,d,J=8.20 Hz), 7.03(2H, d,J=8.20 Hz), 7.11(2H,d,J=8.30 Hz), 7.17–7.29(3H,m), 7.31–7.38(2H,m), 7.58(2H,d,J=8.30 Hz). IR (KBr) cm$^{-1}$: 1659,1593,1387,1343,1141,729.

Example 122

Preparation of 5,6-bis(4-methoxyphenyl)-2-(4-chlorocinnamyl)-2H-pyridazine-3-thione Lawesson's reagent (140 mg, 0.35 mmol) was added to a solution of 5,6-bis(4-methoxyphenyl)-2-(4-chlorocinnamyl)-2H-pyridazin-3-one (146 mg, 0.32 mmol) in toluene (5 ml), followed by stirring at 80° C. for 5 hours under a nitrogen gas atmosphere. A saturated aqueous solution of sodium hydrogencarbonate (10 ml) was added to the reaction mixture, followed by extraction with chloroform. The extract was washed with a brine, and then dried over anhydrous sodium sulfate. The solvent was distilled off, and the thus-obtained yellow oil (321 mg) was separated and purified by chromatography on a silica gel column (silica gel: 36 g, chloroform), whereby the title compound (106 mg, 70.1%) was obtained.

Orange prisms (diethyl ether-hexane) Melting point: 173.3–176.2° C. $^1$H-NMR (CDCl$_3$) δ: 3.80(3H,s), 3.81(3H, s), 5.52(2H,d,J=6.58 Hz), 6.57(1H,dt,J=15.86,6.60 Hz), 6.75 (1H,d,J=15.86 Hz), 6.81(2H,d,J=9.03 Hz), 6.82(2H,d,J= 8.79 Hz), 7.07(2H,d,J=8.79 Hz), 7.89(2H,d,J=8.79 Hz), 7.27 (2H,d,J=8.54 Hz), 7.35(2H,d,J=8.54 Hz), 7.81(1H,s). IR (KBr) cm$^{-1}$: 1608,1513,1397,1256,1178,1162,1257,1089, 836.

Example 123

Preparation of 5,6-bis(4-methoxyphenyl)-2-benzyl-2H-pyridazine-3-thione

Using 5,6-bis(4-methoxyphenyl)-2-benzyl-2H-pyridazin-3-one as a starting material, the procedures of Example 122 were repeated likewise, whereby the title compound was obtained in a yield of 83.4%.

Yellow needles (ethyl acetate-hexane). Melting point: 134.7–148.6° C. Mass (m/e): 414 (M$^+$). $^1$H-NMR (CDCl$_3$) δ: 3.80(6H,s), 6.00(2H,s), 6.80(2H,d,J=9.03 Hz), 6.81(2H, d,J=9.04 Hz), 7.06(2H,d,J=8.79 Hz), 7.16(2H,d,J=8.79 Hz), 7.31–7.36(2H,m). IR (KBr) cm$^{-1}$: 1607,1514,1396,1250, 1174,1160,1153,1029, 833.

Example 124

Preparation of 5,6-bis(4-methoxyphenyl)-2-(4-fluorobenzyl)-2H-pyridazine-3-thione Using 5,6-bis(4-methoxyphenyl)-2-(4-fluorobenzyl)-2H-pyridazin-3-one as a starting material, the procedures of Example 122 were repeated likewise, whereby the title compound was obtained in a yield of 71.3%.

Yellow needles (ethyl acetate-diethyl ether). Melting point: 137.1–137.8° C. $^1$H-NMR (CDCl$_3$) δ: 3.81(6H,s), 5.95(2H,s), 6.80(4H,d,J=8.79 Hz), 7.01–7.07(2H,m), 7.06 (2H,d,J=8.79 Hz), 7.15(2H,d,J=8.79 Hz), 7.31–7.36(3H,m), 7.60–7.65(2H,m), 7.79(1H,s). IR (KBr) cm$^{-1}$: 1609,1512, 1397,1299,1253,1176,1154,1047, 832.

Example 125

Preparation of 5,6-bis(4-methoxyphenyl)-2-(2,4-dichlorobenzyl)-2H-pyridazine-3-thione Using 5,6-bis(4-methoxyphenyl)-2-(2,4-dichlorobenzyl)-2H-pyridazin-3-one as a starting material, the procedures of Example 122 were repeated likewise, whereby the title compound was obtained in a yield of 84.4%.

Yellow needles (ethyl acetate). Melting point: 169.6–170.2° C. $^1$H-NMR (CDCl$_3$) δ: 3.79(3H,s), 3.82(3H, s), 6.01(2H,s), 6.77(2H,d,J=8.78 Hz), 6.83(2H,d,J=8.79 Hz), 7.10(2H,d,J=8.79 Hz), 7.12(2H,d,J=8.79 Hz), 7.14(2H,d,J= 8.30 Hz), 7.21(1H,dd,J=1.96,8.30 Hz), 7.45(1H,d,J=2.20 Hz), 7.83(1H,s). IR (KBr) cm$^{-1}$: 1609,1513,1472,1397, 1297,1251,1177, 1162,1045,834.

Example 126

Preparation of 5,6-bis(4-methoxyphenyl)-2-( 2,4-difluorobenzyl)-2H-pyridazine-3-thione Using 5,6-bis(4-methoxyphenyl)-2-(2,4-difluorobenzyl)-2H-pyridazin-3-one as a starting material, the title compound was obtained in a yield of 57.6% in a similar manner as in Example 122.

Yellow needles (ethyl acetate-diethyl ether). Melting point: 175.4–175.7° C. $^1$H-NMR (CDCl$_3$) δ: 3.79(3H,s), 3.81(3H,s), 5.98(2H,s), 6.78(2H,d,J=8.79 Hz), 6.82(2H,d,J= 8.79 Hz), 6.83–6.89(2H,m), 7.08(2H,d,J=8.79 Hz), 7.13(2H, d,J=8.54 Hz), 7.47–7.56(1H,m), 7.80(1H,s). IR (KBr) cm$^{-1}$: 1609,1514,1504,1397,1300,1252,1174, 1156,1046,833.

Example 127

Preparation of 5,6-bis(4-methoxyphenyl)-2-(3,4,5-trimethoxybenzyl)-2H-pyridazine-3-thione Using 5,6-bis(4-methoxyphenyl)-2-(3,4,5-trimethoxybenzyl)-2H-pyridazin-3-one as a starting material, the procedures of Example 122 were repeated likewise, whereby the title compound was obtained in a yield of 35.1%.

Yellow prisms (ethyl acetate-diethyl ether). Melting point: 142.4–146.4° C. $^1$H-NMR (CDCl$_3$) δ: 3.81(6H,s), 3.84(3H,s), 3.87(6H,s), 5.92(2H,s), 6.80(2H,d,J=9.03 Hz), 6.81(2H,d,J=9.03 Hz), 6.97(2H,s), 7.06(2H,d,J=8.79 Hz), 7.15(2H,d,J=8.79 Hz), 7.80(1H,s). IR (KBr) cm$^{-1}$: 1606, 1511,1459,1423,1250,1127,1033,842.

Example 128

Preparation of 5,6-bis(4-methoxyphenyl)-2-(3-pyridylmethyl)-2H-pyridazine-3-thione Using 5,6-bis(4-methoxyphenyl)-2-(3-pyridylmethyl)-2H-pyridazin-3-one as a starting material, the procedures of Example 122 were repeated likewise, whereby the title compound was obtained in a yield of 86.7%.

Yellow brown prisms. Melting point: 162.7–163.7° C. $^1$H-NMR (CDCl$_3$) δ: 3.81(6H,s), 6.00(2H,s), 6.80(2H,d,J=8.79 Hz), 6.81(2H,d,J=9.04 Hz), 7.06(2H,d,J=9.03 Hz), 7.15 (2H,d,J=9.03 Hz), 7.29(1H,dd,J=4.88,7.81 Hz), 7.79(1H,s), 8.02(1H,d,J=8.06 Hz), 8.57(1H,dd,J=1.46,4.76 Hz), 8.86 (1H,d,J=1.46). IR (KBr) cm$^{-1}$: 1608,1514,1397,1249,1181, 1152,1020,837.

Example 129

Preparation of 5,6-bis(4-methoxyphenyl)-2-(4-pyridylmethyl)-2H-pyridazine-3-thione Using 5,6-bis(4-methoxyphenyl)-2-( 4-pyridylmethyl)-2H-pyridazin-3-one as a starting material, the procedures of Example 122 were repeated likewise, whereby the title compound was obtained in a yield of 84.5%.

Yellow brown prisms (methanol-ethyl acetate). Melting point: 159.6–159.9° C. $^1$H-NMR (CDCl$_3$) δ: 3.81(3H,s), 3.82(3H,s), 5.98(2H,s), 6.81(2H,d,J=9.03 Hz), 6.82(2H,d,J= 9.03 Hz), 7.09(2H,d,J=9.04 Hz), 7.15(2H,d,J=8.79 Hz), 7.40 (2H,d,J=6.10 Hz), 7.81(1H,s), 8.60(2H,d,J=5.86 Hz).

In a manner known per se in the art, the methanesulfonate of the title compound was obtained in a yield of 56.7%.

Yellow prisms (methanol-ethyl acetate). Melting point: 198.5–199.8° C. $^1$H-NMR (CDCl$_3$) δ: 2.89(3H,s), 3.82(3H, s), 3.82(3H,s), 6.14(2H,s), 6.82(2H,d,J=9.03 Hz), 6.84(2H, d,J=9.04 Hz), 7.10(2H,d,J=9.04 Hz), 7.16(2H,d,J=9.04 Hz), 7.79(1H,s), 7.95(2H,d,J=6.83 Hz), 8.86(2H,d,J=6.59 Hz). IR (KBr) cm$^{-1}$: 1640,1606,1511,1396,1247,1175,1152, 1027, 838,800,769.

Example 130

Preparation of 5, 6-bis(4-methoxyphenyl)-2-( 2,4-difluorocinnamyl)-2H-pyridazine-3-thione Using 5,6-bis(4-methoxyphenyl)-2-(2,4-difluorocinnamyl)-2H-pyridazin-3-one as a starting material, the procedures of Example 122 were repeated likewise, whereby the title compound was obtained in a yield of 40.6%.

Yellow needles (ethyl acetate-diethyl ether). Melting point: 140.7–141.4° C. 1-H-NMR (CDCl$_3$) δ: 3.80(3H,s), 3.81(3H,s), 5.54(2H,d,J=6.59 Hz), 6.54(1H,dt,J=16.11,6.59 Hz), 6.75–6.82(2H,m), 6.81(2H,d,J=9.03 Hz), 6.82(2H,d,J= 9.04 Hz), 6.89(1H,d,J=16.12 Hz), 7.08(2H,d,J=8.79 Hz), 7.19(2H,d,J=9.03 Hz), 7.43–7.51(1H,m), 7.81(1H,s). IR (KBr) cm$^{-1}$: 1608,1502,1398,1255,1237,1180,1154,1035, 963,835.

Example 131

Preparation of 5-(4-chlorophenyl)-6-[4-(methylthio) phenyl]-2-cyclopropylmethyl-2H-pyridazine-3-thione Using 5-(4-chlorophenyl)-6-[4-(methylthio)phenyl]-2-cyclopropylmethyl-2H-pyridazin-3-one as a starting material, the procedures of Example 122 were repeated likewise, whereby the title compound was obtained in a yield of 64.5%.

Yellow prisms (ethyl acetate-hexane). Melting point: 135.3–135.4° C. Mass (m/e): 398,400 (M$^+$). $^1$H-NMR (CDCl$_3$) δ: 0.54–0.62(4H,m), 1.68–1.75(1H,m), 4.63(2H,d, J=7.42 Hz), 7.10(2H,d,J=8.20 Hz), 7.14(4H,s), 7.30(2H,d, J=8.20 Hz), 7.81(1H,s). IR (KBr) cm$^{-1}$: 1600,1490,1477, 1129,1101,828.

Example 132

Preparation of 2-benzyl-5-(4-chlorophenyl)-6-[4-(methylthio)phenyl]-2H-pyridazine-3-thione Using 2-benzyl-5-(4-chlorophenyl)-6-[4-(methylthio) phenyl]-2H-pyridazin-3-one as a starting material, the procedures of Example 122 were repeated likewise, whereby the title compound was obtained in a yield of 77.6%.

Yellow needles (ethyl acetate-hexane). Melting point: 103.2–103.3° C. Mass (m/e): 434,436 (M$^+$). $^1$H-NMR (CDCl$_3$) δ: 2.48(3H,s), 5.99(2H,s), 7.07–7.14(8H,m), 7.26–7.39(3H,m), 7.60(2H,d,J=6.64 Hz), 7.79(1H,s). IR (KBr) cm$^{-1}$: 1597,1491,1413,1345,1145,1100,825.

Example 133

Preparation of 5-(4-chlorophenyl)-2-(2,4-difluorobenzyl)-6-[4-(methylthio)phenyl]-2H-pyridazine-3-thione Using 5-(4-chlorophenyl)-2-(2,4-difluorobenzyl)-6-[4-(methylthio)phenyl]-2H-pyridazin-3-one as a starting material, the procedures of Example 122 were repeated likewise, whereby the title compound was obtained in a yield of 65.6%.

Yellow needles (ethyl acetate-hexane). Melting point: 176.5–176.6° C. Mass (m/e): 470,472 (M$^+$). $^1$H-NMR (CDCl$_3$) δ: 2.47(3H,s), 5.97(2H,s), 6.86(2H,t,J=8.30 Hz), 7.05–7.12(6H,m), 7.30(2H,d,J=8.59 Hz), 7.53(1H,dd,J= 14.64,8.20 Hz), 7.80(1H,s). IR (KBr) cm$^{-1}$: 1604,1506, 1410,1336,1154,1101,1089,829.

Example 134

Preparation of 5-(4-chlorophenyl)-2-(2,4-dichlorobenzyl)-6-[4-(methylthio)phenyl]-2H-pyridazine-3-thione Using 5-(4-chlorophenyl)-2-(2,4-dichlorobenzyl)6-[4-(methylthio)phenyl]-2H-pyridazin-3-one as a starting material, the procedures of Example 122 were repeated likewise, whereby the title compound was obtained in a yield of 77.2%.

Yellow needles (ethyl acetate-hexane). Melting point: 183.2–183.4° C. Mass (m/e): 502 (M$^+$). $^1$H-NMR (CDCl$_3$) δ: 2.46(3H,s), 6.00(2H,s), 7.04–7.32(10H,m), 7.46(1H,d,J= 2.15 Hz), 7.82(1H,s). IR (KBr) cm$^{-1}$: 1594,1477,1409,1138, 1099,824.

Example 135

Preparation of 5-(4-chlorophenyl)-6-[4-(methylthio) phenyl]-2-(3-pyridylmethyl)-2H-pyridazine-3-thione Using 5-(4-chlorophenyl)-6-[4-(methylthio)phenyl]-2-(3-pyridylmethyl)-2H-pyridazin-3-one as a starting material, the procedures of Example 122 were repeated likewise, whereby the title compound was obtained in a yield of 99%.

Yellow needles (ethyl acetate-hexane). Melting point: 130.3–131.0° C. Mass (m/e): 435,437 (M+). $^1$H-NMR (CDCl$_3$) δ: 2.48(3H,s), 5.99(2H,s), 7.06–7.15(6H,m), 7.29–7.31(3H,m), 7.78(1H,s), 8.05(1H,d,J=8.20 Hz), 8.58 (1H,d,J=3.32 Hz), 8.86(1H,s). IR (KBr) cm$^{-1}$: 1596,1413, 1147,1101,826.

Example 136

Preparation of 5-(4-fluorophenyl)-6-[4-(methylthio) phenyl]-2H-pyridazine-3-thione Using 5-(4-fluorophenyl)-6-[4-(methylthio)phenyl]-2H-pyridazin-3-one as a starting material, the procedures of Example 122 were repeated likewise, whereby the title compound was obtained in a yield of 84.3%.

Yellow prisms (ethyl acetate-hexane). Melting point: 218.7–218.9° C. Mass (m/e): 328 (M+). $^1$H-NMR (CDCl$_3$) δ: 2.47(3H,s), 7.03(2H,t,J=8.59 Hz), 7.09–7.16(6H,m). IR (KBr) cm$^{-1}$: 3133,1605,1597,1509,1388,1318,1109, 842, 827.

Example 137

Preparation of 2-cyclopropylmethyl-5-(4-fluorophenyl)-6-[4-(methylthio)phenyl]-2H-pyridazine-3-thione Using 2-cyclopropylmethyl-5-(4-fluorophenyl)-6-[4-(methylthio)phenyl]-2H-pyridazin-3-one as a starting material, the procedures of Example 122 were repeated likewise, whereby the title compound was obtained in a yield of 95.6%.

Yellow prisms (ethyl acetate-hexane). Melting point: 135.7–135.8° C. Mass (m/e): 382 (M+). $^1$H-NMR (CDCl$_3$) δ: 0.54–0.64(4H,m), 1.67–1.77(1H,m), 2.47(3H,s), 4.64(2H, d,J=7.32 Hz), 7.02(2H,t,J=8.66 Hz), 7.09–7.17(6H,m), 7.81 (1H,s). IR (KBr) cm$^{-1}$: 1605,1509,1476,1412,1230,1158, 1101,843.

Example 138

Preparation of 2-benzyl-5-(4-fluorophenyl)-6-[4-(methylthio)phenyl]-2H-pyridazine-3-thione Using 2-benzyl-5-(4-fluorophenyl)-6-[4-(methylthio) phenyl]-2H-pyridazin-3-one as a starting material, the procedures of Example 122 were repeated likewise, whereby the title compound was obtained in a yield of 95.6%.

Yellow prisms (diethyl ether-hexane). Melting point: 108.1–108.2° C. Mass (m/e): 418 (M+). $^1$H-NMR (CDCl$_3$) δ: 2.46(3H,s), 5.99(2H,s), 6.97–7.14(7H,m), 7.32–7.37(3H, m), 7.60(2H,d,J=6.10 Hz), 7.79(1H,s). IR (KBr) cm$^{-1}$: 1605, 1509,1417,1162,1101,836.

Example 139

Preparation of 2-benzyl-5-(4-fluorophenyl)-6-[4-(methylsulfonyl)phenyl]-2H-pyridazine-3-thione Using 2-benzyl-5-(4-fluorophenyl)-6-[4-(methylsulfonyl) phenyl]-2H-pyridazin-3-one as a starting material, the procedures of Example 122 were repeated likewise, whereby the title compound was obtained in a yield of 100%.

Yellow prisms (ethyl acetate-hexane). Melting point: 181.8–182.0° C. Mass (m/e): 450 (M+). $^1$H-NMR (CDCl$_3$) δ: 3.06(3H,s), 5.99(2H,s), 7.00–7.11(4H,m), 7.30–7.42(5H, m), 7.58(2H,dd,J=8.01,1.56 Hz), 7.84(1H,s), 7.87(2H,d,J= 10.35 Hz). IR (KBr) cm$^{-1}$: 1604,1511,1308,1163,1152, 1083,848,571.

Example 140

Preparation of 5-(4-fluorophenyl)-2-(4-methoxybenzyl)-6-(4-(methylthio)phenyl]-2H-pyridazine-3-thione Using 5-(4-fluorophenyl)-2-(4-methoxybenzyl)-6-[4-(methylthio)phenyl]-2H-pyridazin-3-one as a starting material, the procedures of Example 122 were repeated likewise, whereby the title compound was obtained in a yield of 92.2%.

Yellow powder (ethyl acetate-hexane). Melting point: 112.7–112.9° C. Mass (m/e): 448 (M+). $^1$H-NMR (CDCl$_3$) δ: 2.47(3H,s), 3.79(3H,s), 5.92(2H,s), 6.89(2H,d,J=8.54 Hz), 6.99(2H,d,J=8.54 Hz), 7.09–7.14(6H,m), 7.60(2H,d,J= 8.54 Hz), 7.78(1H,s). IR (KBr) cm$^{-1}$: 1607,1511,1248,1162, 1101.

Example 141

Preparation of 2-(2,4-dichlorobenzyl)-5-( 4-fluorophenyl)-6-[4-(methylthio)phenyl]-2H-pyridazine-3-thione Using 2-(2,4-dichlorobenzyl)-5-(4-fluorophenyl)-6-[4-(methylthio)phenyl]-2H-pyridazin-3-one as a starting material, the procedures of Example 122 were repeated likewise, whereby the title compound was obtained in a yield of 79.8%.

Yellow needles (ethyl acetate-hexane). Melting point: 154.0–154.2° C. Mass (m/e): 487 (M+). $^1$H-NMR (CDCl$_3$) δ: 2.45(3H,s), 6.00(2H,s), 7.00–7.10(6H,m), 7.13–7.22(4H, m), 7.45(1H,d,J=1.95 Hz), 7.82(1H,s). IR (KBr) cm$^{-1}$: 1597, 1509,1414,1099,839,824.

Example 142

Preparation of 2-(4-chlorobenzyl)-6-(4-methoxyphenyl)-5-(4-pyridyl)-2H-pyridazine-3-thione Using 2-(4-chlorobenzyl)-6-(4-methoxyphenyl)-5-(4-pyridyl)-2H-pyridazin-3-one as a starting material, the procedures of Example 122 were repeated likewise, whereby the title compound was obtained in a yield of 45.3%.

Yellow prisms (chloroform-hexane). Melting point: 144.4–145.1° C. $^1$H-NMR (CDCl$_3$) δ: 3.79(3H,s), 5.92(2H, s), 6.81(2H,d,J=8.90 Hz), 7.05(2H,dd,J=1.65,4.45 Hz), 7.11 (2H,d,J=8.90 Hz), 7.31(2H,d,J=8.42 Hz), 7.55(2H,d,J=8.42 Hz), 7.77(1H,s), 8.57(2H,dd,J=1.65,4.45 Hz). IR (KBr) cm$^{-1}$: 1609,1516,1491,1477,1416,1399,1343, 1252,1163, 1146.

Example 143

Preparation of 6-(3-fluoro-4-methoxyphenyl)-5-(4-methoxyphenyl)-2H-pyridazine-3-thione To a solution of sodium periodate (1.66 g) in water (10 ml), sulfuric acid (0.163 ml) was added under ice cooling, followed by the addition of a solution of tartaric acid (1.16 g) in water (3 ml). The resulting solution was stirred at room temperature for 30 minutes. Added to the solution were 3'-fluoro-4'-methoxy-2-(4-methoxyphenyl)acetophenone (2.12 g, 7.73 mmol), a solution of sodium hydroxide (0.92 g) in water (15 ml) and ethanol (20 ml), followed by stirring overnight at room temperature. After the mixture was heated at 70° C. for 40 minutes, the ethanol was distilled off, and water was then added. The mixture was washed with ethyl acetate. The water layer was acidified with hydrochloric acid, followed by extraction with ethyl acetate. The extract was washed successively with water and a brine, and was then dried over anhydrous sodium sulfate. The solvent was distilled off under reduced pressure. The crude oil (1.29 g) was dissolved in ethanol (50 ml) and subsequent to addition of hydrazine hydrate (356 mg), the resultant mixture was heated overnight under reflux. A 2 N aqueous solution of sodium hydroxide (40 ml) was added to the reaction mixture, followed by heating under reflux for 2 hours. After the reaction mixture was neutralized with hydrochloric acid, the thus-obtained mixture was extracted with ethyl acetate. The organic layer was washed with a brine and was then dried over anhydrous sodium sulfate. The solvent was distilled off. The residue was separated and purified by chromatography on a silica gel column and was then crystallized from ethanol, whereby the title compound (764 mg, 30.3%) was obtained as yellow prisms.

Melting point: 221.8–223.0° C. Mass (m/Z): 326 (M$^+$). $^1$H-NMR (CDCl$_3$) δ: 3.82(3H,s), 3.88(3H,s), 6.80–6.87(3H, m), 6.91(1H,ddd,J=8.5,2.2,1.0 Hz), 6.94(1H,s), 6.98(1H,dd, J=12.0,2.2 Hz), 7.06(2H,d,J=9.0 Hz), 11.90(1H,brs). IR (KBr) cm$^{-1}$: 1652,1610,1515,1311,1298,1271,1261,1249, 1025.

Example 144

Preparation of 2-benzyl-6-(3-fluoro-4-methoxyphenyl)-5-(4-methoxyphenyl)-2H-pyridazin-3-one Using 6-(3-fluoro-4-methoxyphenyl)-5-(4-methoxyphenyl)-2H-pyridazin-3-one and benzyl bromide as starting materials, the procedures of Example 12 were repeated likewise, whereby the title compound was obtained in a yield of 95.8%.

Pale yellow prisms (ethyl acetate-hexane). Melting point: 136.6–137.8° C. Mass (m/Z): 416 (M$^+$). $^1$H-NMR (CDCl$_3$) δ: 3.81(3H,s), 3.87(3H,s), 5.41(2H,s), 6.76–6.83(3H,m), 6.85(1H,dd,J=8.5,2.0 Hz), 6.88(1H,s), 6.97(1H,dd,J=12.0, 2.0 Hz), 7.02(2H,d,J=8.5 Hz), 7.27–7.41(3H,m), 7.53(2H, d,J=7.1 Hz). IR (KBr) cm$^{-1}$: 1671,1610,1519,1511,1432, 1304,1292,1275, 1249,1177,822.

Example 145

Preparation of 2-(4-chlorocinnamyl)-6-(3-fluoro-4-methoxyphenyl)-5-(4-methoxyphenyl)-2H-pyridazin-3-one Using 6-(3-fluoro-4-methoxyphenyl)-5-(4-methoxyphenyl)-2H-pyridazin-3-one and 4-chlorocinnamyl chloride as starting materials, the procedures of Example 12 were repeated likewise, whereby the title compound was obtained in a yield of 72.5%.

Colorless crystalline powder (ethyl acetate-hexane). Melting point: 144.0–145.4° C. Mass (m/Z): 476 (M$^+$). $^1$H-NMR (CDCl$_3$) δ: 3.81(3H,s), 3.87(3H,s), 4.99(2H,d,J= 6.6 Hz), 6.44(1H,dt,J=15.9,6.6 Hz), 6.69(1H,d,J=15.9 Hz), 6.79–6.90(4H,m), 6.91(1H,s), 7.01(1H,dd,J=12.2,2.0 Hz), 7.04(2H,d,J=8.5 Hz), 7.27(2H,d,J=8.5 Hz), 7.32(2H,d,J=8.5 Hz). IR (KBr) cm$^{-1}$: 1666,1610,1520,1512,1279,1247.

Example 146

Preparation of 2-ethyl-6-(3-fluoro-4-methoxyphenyl)-5-(4-methoxyphenyl)-2H-pyridazin-3-one To a solution of 6-(3-fluoro-4-methoxyphenyl)-5-(4-methoxyphenyl)-2H-pyridazin-3-one (150 mg, 0.46 mmol) in N,N-dimethylformamide (1.5 ml), potassium carbonate (317.6 mg) and ethyl iodide (179.2 mg) were added, followed by stirring at 70° C. for 3 hours. The reaction mixture was concentrated, followed by the addition of water. The mixture was extracted with ethyl acetate, and the extract was dried over anhydrous sodium sulfate. The solvent was distilled off under reduced pressure. The residue was separated and purified by preparative silica gel chromatography and then crystallized from ethyl acetate-hexane, whereby the title compound (156 mg, 95.8%) was obtained as pale yellow needles.

Melting point: 122.6–123.5° C. Mass (m/Z): 354 (M$^+$). $^1$H-NMR (CDCl$_3$) δ: 1.46(3H,t,J=7.2 Hz), 3.81(3H,s), 3.87 (3H,s), 4.30(2H,q,J=7.2 Hz), 6.79–6.86(3H,m), 6.87–6.92 (2H,m), 7.01(1H,dd,J=12.2,2.0 Hz), 7.04(2H,d,J=8.8 Hz). IR (KBr) cm$^{-1}$: 1659,1609,1520,1512,1305,1297,1277, 1244, 1181,1131,1022,837.

Example 147

Preparation of 6-(3-fluoro-4-methoxyphenyl)-2-isobutyl-5-(4-methoxyphenyl)-2H-pyridazin-3-one Using 6-(3-fluoro-4-methoxyphenyl)-5-(4-methoxyphenyl)-2H-pyridazin-3-one and isobutyl bromide as starting materials, the procedures of Example 146 were repeated likewise, whereby the title compound was obtained in a yield of 91.3%.

Colorless needles (diethyl ether-hexane). Melting point: 86.8–87.4° C. Mass (m/Z): 382 (M$^+$). $^1$H-NMR (CDCl$_3$) δ: 1.01(6H,d,J=6.8 Hz), 2.37(1H,tsep,J=7.3,6.8 Hz), 3.81(3H, s), 3.87(3H,s), 4.08(2H,d,J=7.3 Hz), 6.79–6.86(3H,m), 6.87 (1H,dd,J=2.1,0.6 Hz), 6.89(1H,s), 7.00(1H,dd,J=12.1,2.1 Hz), 7.05(2H,d,J=9.0 Hz). IR (KBr) cm$^{-1}$: 1660,1610,1521, 1512,1305,1297,1277, 1245,1177.

Example 148

Preparation of 2-cyclopropylmethyl-6-(3-fluoro-4-methoxyphenyl)-5-(4-methoxyphenyl)-2H-pyridazin-3-one Using 6-(3-fluoro-4-methoxyphenyl)-5-(4-methoxyphenyl)-2H-pyridazin-3-one and (chloromethyl) cyclopropane as starting materials, the procedures of Example 146 were repeated likewise, whereby the title compound was obtained in a yield of 93.0%.

Colorless prisms (ethyl acetate-hexane). Melting point: 132.2–132.6° C. Mass (m/Z): 380 (M$^+$). $^1$H-NMR (CDCl$_3$) δ: 0.46–0.62(4H,m), 1.45(1H,ttt,J=7.8,7.3,4.9 Hz), 3.82(3H, s), 3.87(3H,s), 4.11(2H,d,J=7.3 Hz), 6.80–6.91(5H,m), 7.01 (1H,dd,J=12.2,2.0 Hz), 7.06(2H,d,J=9.0 Hz). IR (KBr) cm$^{-1}$: 1660,1612,1521,1511,1306,1295,1278,1244, 1176, 1019,828.

Example 149

Preparation of 4,5-dihydro-5-(3-fluoro-4-methoxyphenyl)-6-(4-methoxyphenyl)-2H-pyridazin-3-one Using ethyl 3-(3-fluoro-4-methoxyphenyl)-4-( 4-methoxyphenyl)-4-oxobutanoate as a starting material, the procedures of Example 1 were repeated likewise, whereby the title compound was obtained in a yield of 55.3%.

Pale yellow scales (ethyl acetate-hexane). Melting point: 171.2–173.4° C. Mass (m/Z): 328 (M$^+$). $^1$H-NMR (CDCl$_3$) δ: 2.75(1H,dd,J=16.8,1.2 Hz), 2.97(1H,dd,J=16.8,7.7 Hz), 3.82(3H,s), 3.85(3H,s), 4.40(1H,dd,J=7.6,1.2 Hz), 6.85–6.98(5H,m), 7.64(2H,d,J=8.8 Hz), 8.54(1H,brs). IR (KBr) cm$^{-1}$: 1675,1660,1616,1516,1351,1278,1255,1174.

Example 150

Preparation of 5-(3-fluoro-4-methoxyphenyl)-6-(4-methoxyphenyl)-2H-pyridazin-3-one Using 4,5-dihydro-5-(3-fluoro-4-methoxyphenyl)-6-(4-methoxyphenyl)-2H-pyridazin-3-one as a starting material, the procedures of Example 7 were repeated likewise, whereby the title compound was obtained in a yield of 90.2%.

Colorless needles (ethyl acetate-hexane). Melting point: 212.8–213.4° C. Mass (m/Z): 326 (M$^+$). $^1$H-NMR (CDCl$_3$) δ: 3.80(3H,s), 3.89(3H,s), 6.79(2H,d,J=8.8 Hz), 6.85(1,d,J=11.7 Hz), 6.87–6.93(2H,m), 6.96(1H,s), 7.13(2H,d,J=8.8 Hz), 12.75(1H,brs). IR (KBr) cm$^{-1}$: 1667,1614,1520,1308, 1278,1254,1132,1022, 835.

Example 151

Preparation of 2-benzyl-5-(3-fluoro-4-methoxyphenyl)-6-(4-methoxyphenyl)-2H-pyridazin-3-one Using 5-(3-fluoro-4-methoxyphenyl)-6-(4-methoxyphenyl)-2H-pyridazin-3-one and benzyl bromide as starting materials, the procedures of Example 12 were repeated likewise, whereby the title compound was obtained in a yield of 95.6%.

Colorless needles (ethyl acetate-hexane). Melting point: 109.6–111.6° C. Mass (m/Z): 416 (M$^+$). $^1$H-NMR (CDCl$_3$) δ: 3.79(3H,s), 3.87(3H,s), 5.41(2H,s), 6.76–6.89(6H,m), 7.10(2H,d,J=8.8 Hz), 7.27–7.38(3H,m), 7.50–7.55(2H,m). IR (KBr) cm$^{-1}$: 1667,1608,1516,1462,1295,1276,1248, 1181, 1131,1021,873.

Example 152

Preparation of 2-(4-chlorocinnamyl)-5-(3-fluoro-4-methoxyphenyl)-6-(4-methoxyphenyl)-2H-pyridazin-3-one Using 5-(3-fluoro-4-methoxyphenyl)-6-(4-methoxyphenyl)-2H-pyridazin-3-one and 4-chlorocinnamyl chloride as starting materials, the procedures of Example 12 were repeated likewise, whereby the title compound was obtained in a yield of 58.7%.

Colorless crystalline powder (ethyl acetate-hexane). Melting point: 109.2–111.0° C. Mass (m/Z): 476 (M$^+$). $^1$H-NMR (CDCl$_3$) δ: 3.79(3H,s), 3.88(3H,s), 4.99(2H,d,J=6.6 Hz), 6.44(1H,dt,J=15.9,6.6 Hz), 6.68(1H,d,J=15.9 Hz), 6.80(2H,d,J=9.0 Hz), 6.82–6.90(3H,m), 6.91(1H,s), 7.13 (2H,d,J=9.0 Hz), 7.26(2H,d,J=8.5 Hz), 7.32(2H,d,J=8.5 Hz). IR (KBr) cm$^{-1}$: 1655,1611,1515,1491,1306,1275,1250, 1177, 1129.

Example 153

Preparation of 2-ethyl-5-(3-fluoro-4-methoxyphenyl)-6-(4-methoxyphenyl)-2H-pyridazin-3-one Using 5-(3-fluoro-4-methoxyphenyl)-6-(4-methoxyphenyl)-2H-pyridazin-3-one and ethyl iodide as starting materials, the procedures of Example 146 were repeated likewise, whereby the title compound was obtained in a yield of 97.8%.

Colorless needles (ethyl acetate-hexane). Melting point: 161.7–162.2° C. Mass (m/Z): 354 (M$^+$). $^1$H-NMR (CDCl$_3$) δ: 1.46(3H,t,J=7.1 Hz), 3.80(3H,s), 3.89(3H,s), 4.31(2H,q, J=7.1 Hz), 6.78–6.92(6H,m), 7.13(1H,d,J=8.8 Hz). IR (KBr) cm$^{-1}$: 1655,1612,1519,1515,1305,1297,1278,1252, 1175, 1130,1022,833.

Example 154

Preparation of 5-(3-fluoro-4-methoxyphenyl)-2-isobutyl-6-(4-methoxyphenyl)-2H-pyridazin-3-one Using 5-(3-fluoro-4-methoxyphenyl)-6-(4-methoxyphenyl)-2H-pyridazin-3-one and isobutyl iodide as starting materials, the procedures of Example 146 were repeated likewise, whereby the title compound was obtained in a yield of 75.1%.

Colorless prisms (ethyl acetate-hexane). Melting point: 124.6–125.0° C. Mass (m/Z): 382 (M$^+$). $^1$H-NMR (CDCl$_3$) δ: 1.01(6H,d,J=6.8 Hz), 2.37(1H,tsep,J=7.6,6.8 Hz), 3.80 (3H,s), 3.89(3H,s), 4.08(2H,d,J=7.6 Hz), 6.80(2H,d,J=9.0 Hz), 6.84(1H,dd,J=11.3,1.3 Hz), 6.87–6.91(3H,m), 7.12(2H, d,J=9.0 Hz). IR (KBr) cm$^{-1}$: 1660,1612,1517,1463,1443, 1308,1299,1281, 1251,1238,1178,1133,1023.

Example 155

Preparation of 2-cyclopropylmethyl-5-(3-fluoro- 4-methoxyphenyl)-6-(4-methoxyphenyl)-2H-pyridazin-3-one Using 5-(3-fluoro-4-methoxyphenyl)-6-(4-methoxyphenyl)-2H-pyridazin-3-one and (chloromethyl) cyclopropane as starting materials, the procedures of Example 146 were repeated likewise, whereby the title compound was obtained in a yield of 93.8%.

Colorless prisms (ethyl acetate-hexane). Melting point: 135.2–135.7° C. Mass (m/Z): 380 (M$^+$). $^1$H-NMR (CDCl$_3$) δ: 0.46–0.62(4H,m), 1.42(1H,ttt,J=7.8,7.3,4.9 Hz), 3.80(3H, s), 3.89(3H,s), 4.11(2H,d,J=7.3 Hz), 6.80(2H,d,J=8.8 Hz), 6.82–6.93(4H,m), 7.13(2H,d,J=8.8 Hz). IR (KBr) cm$^{-1}$: 1661,1611,1586,1519,1309,1295,1282,1249, 1181,1130, 1021,823.

Example 156

Preparation of 5,6-bis(3-fluoro-4-methoxyphenyl)-4, 5-dihydro-2H-pyridazin-3-one Using ethyl 3,4-bis(3-fluoro-4-methoxyphenyl)-4-oxobutanoate as a starting material, the procedures of Example 1 were repeated likewise, whereby the title compound was obtained in a yield of 22.9%.

Colorless needles (ethyl acetate-hexane). Melting point: 195.7–197.7° C. Mass (m/Z): 346 (M$^+$). $^1$H-NMR (CDCl$_3$) δ: 2.76(1H,d,J=17.1 Hz), 2.97(1H,dd,J=17.1,7.6 Hz), 3.85 (3H,s), 3.89(3H,s), 4.35(1H,d,J=7.6 Hz), 6.84–6.95(4H,m), 7.35(1H,d,J=8.8 Hz), 7.51(1H,dd,J=12.6,1.6 Hz), 8.71(1H, brs). IR (KBr) cm$^{-1}$: 1661,1622,1519,1351,1279.

Example 157

Preparation of 5,6-bis(3-fluoro-4-methoxyphenyl)-2H-pyridazin-3-one

Using 5,6-bis(3-fluoro-4-methoxyphenyl)-4,5-dihydro-2H-pyridazin-3-one as a starting material, the procedures of Example 7 were repeated likewise, whereby the title compound was obtained in a yield of 94.9%.

Yellow prisms (chloroform-methanol-hexane). Melting point: 204.8–205.7° C. Mass (m/Z): 344 (M$^+$). $^1$H-NMR (CDCl$_3$) δ: 3.89(3H,s), 3.91(3H,s), 6.81–6.95(6H,m), 6.97 (1H,dd,J=12.0,2.2 Hz), 12.04(1H,brs). IR (KBr) cm$^{-1}$: 1652, 1618,1589,1519,1439,1308,1278,1139, 1128,1023,815.

Example 158

Preparation of 2-benzyl-5,6-bis(3-fluoro- 4-methoxyphenyl)-2H-pyridazin-3-one

Using 5,6-bis(3-fluoro-4-methoxyphenyl)-2H-pyridazin-3-one and benzyl bromide as starting materials, the procedures of Example 12 were repeated likewise, whereby the title compound was obtained in a yield of 99.9%.

Colorless prisms (ethyl acetate-hexane). Melting point: 114.1–115.2° C. Mass (m/Z): 434 (M$^+$). $^1$H-NMR (CDCl$_3$) δ: 3.88(3H,s), 3.89(3H,s), 5.40(2H,s), 6.78–7.01(7H,m), 7.28–7.39(3H,m), 7.52(2H,dd,J=8.2,1.3 Hz). IR (KBr) cm$^{-1}$: 1671,1517,1430,1424,1308,1276,1130.

Example 159

Preparation of 5,6-bis(3-fluoro-4-methoxyphenyl)-2-(4-chlorocinnamyl)-2H-pyridazin-3-one Using 5,6-bis(3-fluoro-4-methoxyphenyl)-2H-pyridazin-3-one and 4-chlorocinnamyl chloride as starting materials, the procedures of Example 12 were repeated likewise, whereby the title compound was obtained in a yield of 42.9%.

Yellow crystalline powder (diethyl ether-hexane). Melting point: 72.5–74.9° C. Mass (m/Z): 494 (M$^+$). $^1$H-NMR (CDCl$_3$) δ: 3.88(3H,s), 3.90(3H,s), 4.99(2H,d,J=6.6 Hz), 6.43(1H,dt,J=15.9,6.6 Hz), 6.69(1H,d,J=15.9 Hz), 6.80–6.95(6H,m), 6.99(1H,dd,J=12.1,1.8 Hz), 7.27(2H,d,J= 8.5 Hz), 7.32(2H,d,J=8.5 Hz). IR (KBr) cm$^{-1}$: 1664,1619, 1589,1520,1491,1440,1307, 1278,1133,1025.

Example 160

Preparation of 5,6-bis(3-fluoro-4-methoxyphenyl)-2-ethyl-2H-pyridazin-3-one

Using 5,6-bis(3-fluoro-4-methoxyphenyl)-2H-pyridazin-3-one and ethyl iodide as starting materials, the procedures of Example 146 were repeated likewise, whereby the title compound was obtained in a yield of 97.2%.

Colorless needles (ethyl acetate-hexane). Melting point: 177.8–178.5° C. Mass (m/Z): 372 (M$^+$). $^1$H-NMR (CDCl$_3$) δ: 1.46(3H,t,J=7.1 Hz), 3.89(3H,s), 3.91(3H,s), 4.30(2H,q, J=7.1 Hz), 6.79–6.95(6H,m), 7.00(1H,dd,J=11.1,1.8 Hz). IR (KBr) cm$^{-1}$: 1655,1519,1306,1286,1275,1133,1127,1023.

Example 161

Preparation of 5,6-bis(3-fluoro-4-methoxyphenyl)-2-isobutyl-2H-pyridazin-3-one

Using 5,6-bis(3-fluoro-4-methoxyphenyl)- 2H-pyridazin-3-one and isobutyl iodide as starting materials, the procedures of Example 146 were repeated likewise, whereby the title compound was obtained quantitatively.

Colorless prisms (ethyl acetate-hexane). Melting point: 154.0–154.5° C. Mass (m/Z): 400 (M$^+$). $^1$H-NMR (CDCl$_3$) δ: 1.01(6H,d,J=6.8 Hz), 2.36(1H,tsep,J=7.3,6.8 Hz), 3.89 (3H,s), 3.91(3H,s), 4.08(2H,d,J=7.3 Hz), 6.81–6.94(6H,m), 6.99(1H,dd,J=12.3,1.8 Hz). IR (KBr) cm$^{-1}$: 1660,1521, 1438,1308,1289,1274,1134,1021.

Example 162

Preparation of 5,6-bis(3-fluoro-4-methoxyphenyl)-2-cyclopropylmethyl-2H-pyridazin-3-one Using 5,6-bis(3-fluoro-4-methoxyphenyl)-2H-pyridazin-3-one and (chloromethyl)cyclopropane as starting materials, the procedures of Example 146 were repeated likewise, whereby the title compound was obtained quantitatively.

Colorless prisms (ethyl acetate-hexane). Melting point: 142.3–142.7° C. Mass (m/Z): 398 (M$^+$). $^1$H-NMR (CDCl$_3$) δ: 0.45–0.52(2H,m), 0.54–0.62(2H,m), 1.44(1H,ttt,J=7.6, 7.3,4.9 Hz), 3.89(3H,s), 3.91(3H,s), 4.11(2H,d,J=7.3 Hz), 6.81–6.94(6H,m), 7.00(1H,dd,J=12.1,1.8 Hz). IR (KBr) cm$^{-1}$: 1660,1590,1522,1515,1447,1427,1308,1278, 1145, 1129,1018,862,761.

Example 163

Preparation of 5,6-bis(4-methoxyphenyl)-2-ethyl-2H-pyridazin-3-one

Ethyl iodide (280 mg, 1.8 mmol) was added to a suspension of 5,6-bis(4-methoxyphenyl)-2H-pyridazin-3-one (463 mg, 1.5 mmol) and potassium carbonate (311 mg, 2.25 mmol) in N,N-dimethylformamide (5 ml), followed by heating at 70° C. under stirring for 9.5 hours. Water was added to the reaction mixture, and the thus-obtained mixture was extracted with ethyl acetate. The extract was washed successively with water and a brine, and was then dried over anhydrous sodium sulfate. The solvent was distilled off, and the residue so obtained was separated and purified by chromatography on a silica gel column (silica gel: 11 g), whereby yellow crystals (466 mg) were obtained. The crystals were recrystallized from ethyl acetate-n-hexane, whereby the title compound (360 mg, 78.3%) was obtained as pale yellow prisms.

Melting point: 142.8–143.4° C. $^1$H-NMR (CDCl$_3$) δ: 1.46(3H,t,J=7.08 Hz), 3.80(3H,s), 3.81(3H,s), 4.31(2H,q,J= 7.08 Hz), 6.79(2H,d,J=9.03 Hz), 6.81(2H,d,J=8.79 Hz), 6.89 (1H,s), 7.04(2H,d,J=8.79 Hz), 7.14(2H,d,J=9.03 Hz). IR (KBr) cm$^{-1}$: 3447,1656,1608,1513,1294,1249,1183,1023, 840.

Example 164

Preparation of 5,6-bis(4-methoxyphenyl)-2-methyl-2H-pyridazin-3-one

Similarly to Example 163, the title compound was obtained in a yield of 100%.

Colorless oil. $^1$H-NMR (CDCl$_3$) δ: 3.79(3H,s), 3.80(3H, s), 3.88(3H,s), 6.79(2H,d,J=8.79 Hz), 6.81(2H,d,J=8.79 Hz), 6.91(1H,s), 7.04(2H,d,J=8.78 Hz), 7.14(2H,d,J=9.03 Hz). IR (film) cm$^{-1}$: 3479,2972,2937,2839,1660,1609,1184, 1296,1247,1180,1032,997,834.

Example 165

Preparation of 5,6-bis(4-methoxyphenyl)-2-isopropyl-2H-pyridazin-3-one

Similarly to Example 163, the title compound was obtained in a yield of 100%.

Pale yellow amorphous. $^1$H-NMR (CDCl$_3$) δ: 1.44(6H,d, J=6.54 Hz), 3.80(3H,s), 3.81(3H,s), 5.39(1H,seplet,J=6.60 Hz), 6.79(2H,d,J=8.79 Hz), 6.83(2H,d,J=8.79 Hz), 6.87(1H, s), 7.06(2H,d,J=8.79 Hz), 7.50(2H,d,J=9.04 Hz). IR (KBr) cm$^{-1}$: 1656,1609,1513,1295,1248,1176,1026,833.

Example 166

Preparation of 5,6-bis(4-methoxyphenyl)-2-isopropyl-2H-pyridazin-3-one

Similarly to Example 163, the title compound was obtained in a yield of 68.1%.

Colorless prisms (ethyl acetate-diethyl ether). Melting point: 128.3–129.1° C. $^1$H-NMR (CDCl$_3$) δ: 1.00(3H,s), 1.02(3H,s), 2.35–2.40(1H,m), 3.79(3H,s), 3.81(3H,s), 4.08 (2H,d,J=7.57 Hz), 6.79(2H,d,J=8.79 Hz), 6.81(2H,d,J=8.79 Hz), 6.89(1H,s), 7.05(2H,d,J=8.79 Hz), 7.12(2H,d,J=9.04 Hz). IR (KBr) cm$^{-1}$: 2958,1660,1606,1515,1248,1177,1027, 837.

Example 167

Preparation of 2-allyl-5,6-bis(4-methoxyphenyl)-2H-pyridazin-3-one

Similarly to Example 163, the title compound was obtained in a yield of 40.2%.

Pale yellow needles (ethyl acetate-n-hexane). Melting point: 114.0–115.0° C. $^1$H-NMR (CDCl$_3$) δ: 3.79(3H,s), 3.81(3H,s), 4.86(2H,d,J=5.86 Hz), 5.28(1H,d,J=10.25 Hz), 5.33(1H,d,J=17.09 Hz), 6.10(1H,tdd,J=5.86,10.25,17.09 Hz), 6.78(2H,d,J=8.79 Hz), 6.81(2H,d,J=8.79 Hz), 6.90(1H, s), 7.04(2H,d,J=9.03 Hz), 7.12(2H,d,J=8.79 Hz). IR (KBr) cm$^{-1}$: 1662,1608,1511,1296,1250,1022,836.

Example 168

Preparation of 5,6-bis(4-methoxyphenyl)-2-cyclopropyl-2H-pyridazin-3-one

Similarly to Example 163, the title compound was obtained in a yield of 2.3%.

Pale yellow oil. Mass (m/e): 348 (M$^+$). $^1$H-NMR (CDCl$_3$) δ: 1.00–1.18(2H,m), 1.20–2.25(2H,m), 3.79(3H,s), 3.81(3H, s), 4.20–4.30(1H,m), 6.77(2H,d,J=9.28 Hz), 6.81(2H,d,J=8.79 Hz), 6.89(1H,s), 7.05(2H,d,J=9.03 Hz), 7.14(2H,d,J=9.03 Hz). IR (KBr) cm$^{-1}$: 1733,1661,1652,1609,1515,1296, 1250,1179, 1111,1026,834.

Example 169

Preparation of 5,6-bis(4-methoxyphenyl)-2-cyclopropylmethyl-2H-pyridazin-3-one

Similarly to Example 163, the title compound was obtained in a yield of 89.6%.

Pale yellow crystalline powder (chloroform-diethyl ether-n-hexane). Melting point: 128.8–129.3° C. $^1$H-NMR (CDCl$_3$) δ: 0.46–0.62(4H,m), 1.38–1.54(1H,m), 3.80(3H,s), 3.81(3H,s), 4.12(2H,d,J=7.08 Hz), 6.79(2H,d,J=9.04 Hz), 6.81(2H,d,J=8.79 Hz), 6.90(1H,s), 7.06(2H,d,J=8.79 Hz), 7.10(2H,d,J=8.79 Hz). IR (KBr) cm$^{-1}$: 1656,1609,1566, 1514,1247,1183,1028,838.

Example 170

Preparation of 5,6-bis(4-methoxyphenyl)-2-cyclopropylmethyl-2H-pyridazine-3-thione Lawesson's reagent (184 mg, 0.46 mmol) was added to a solution of 5,6-bis(4-methoxyphenyl)-2-cyclopropylmethyl-2H-pyridazin-3-one (165 mg, 0.46 mmol) in toluene (6 ml), followed by stirring at 70° C. for 1 hour under a nitrogen gas atmosphere. The solvent was distilled off, and the resulting residue was separated and purified by chromatography on a silica gel column [silica gel: 18 g, n-hexane/ethyl acetate (4/1)]. Crystallization was then effected from ethyl acetate-diethyl ether, whereby the title compound (127 mg, 72.9%) was obtained as yellow scales.

Melting point: 147.5–148.5° C. $^1$H-NMR (CDCl$_3$) δ: 0.56–0.62(4H,m), 1.68–1.75(1H,m), 3.81(3H,s), 3.82(3H,s), 4.64(2H,d,J=7.33 Hz), 6.81(2H,d,J=9.04 Hz), 6.82(2H,d,J= 9.03 Hz), 7.09(2H,d,J=8.79 Hz), 7.19(2H,d,J=9.03 Hz), 7.82 (1H,s). IR (KBr) cm$^{-1}$: 1609,1513,1416,1248,1186,1181, 1122,1021, 834.

Example 171

Preparation of 5,6-bis(4-methoxyphenyl)-2-cyclopentyl-2H-pyridazin-3-one

Similarly to Example 163, the title compound was obtained in a yield of 65.4%.

Pale yellow prisms (chloroform-n-hexane). Melting point: 141.2–142.2° C. Mass (m/e): 376 (M$^+$). $^1$H-NMR (CDCl$_3$) δ: 1.60–1.80(2H,m), 1.80–2.20(6H,m), 3.80(3H,s), 3.81(3H,s), 5.25(2H,quintet,J=6.60 Hz), 6.78(2H,d,J=8.79 Hz), 6.82(2H,d,J=8.79 Hz), 6.86(1H,s), 7.06(2H,d,J=9.03 Hz), 7.14(2H,d,J=9.03 Hz). IR (KBr) cm$^{-1}$: 1661,1611, 1512,1295,1255,1175,1020,833.

Example 172

Preparation of 5,6-bis(4-methoxyphenyl)-2-cyclopentylmethyl-2H-pyridazin-3-one

Similarly to Example 163, the title compound was obtained in a yield of 57.1%.

Colorless scales (ethyl acetate-diethyl ether). Melting point: 130.3–131.4° C. $^1$H-NMR (CDCl$_3$) δ: 1.37–1.79(8H, m), 2.56(1H,quintet,J=7.57 Hz), 3.80(3H,s), 3.81(3H,s), 4.21(2H,d,J=7.82 Hz), 6.79(2H,d,J=8.79 Hz), 6.81(2H,d,J= 8.54 Hz), 6.89(1H,s), 7.05(2H,d,J=9.04 Hz), 7.13(2H,d,J= 9.04 Hz). IR (KBr) cm$^{-1}$: 1664,1609,1513,1292,1250,1179, 1023,831.

Test 1

Inhibitory Activity Against Interleukin-1β Production

HL-60 cells were cultured for 4 days until confluence on RPMI 1640 medium with 10% fetal bovine serum (FBS) added thereto. The HL-60 cells were centrifuged. The supernatant was discarded, and the cells were then suspended at 1×10$^6$ cells/ml on RPMI 1640 medium with 3% FBS, and lipopolysaccharide was added to give a final concentration of 10 μg/ml. The culture was inoculated at 1 ml/well to a 24-well plate. A test sample was added at 1 μl/well, followed by culturing for 3 days. Three days later, the amount of interleukin-1β in each of the cultures was measured by ELISA. Its IC$_{50}$ value was determined by a comparison in yield with a control to which no test sample was added. Results on some representative compounds are shown in Table 1.

TABLE 1

Inhibitory Activity against Interleukin-1β (IL-1β) Production

| Test compound (Example No.) | IL-1β IC$_{50}$ (μM) |
|---|---|
| 12 | 0.10 |
| 13 | 0.26 |
| 14 | 0.094 |
| 16 | 0.23 |
| 19 | 0.079 |
| 23 | 0.36 |
| 24 | 0.20 |
| 25 | 0.18 |
| 26 | 0.15 |
| 27 | 0.18 |
| 28 | 0.29 |
| 30 | 0.17 |
| 31 | 0.095 |
| 35 | 0.21 |
| 40 | 0.27 |
| 44 | 0.43 |
| 51 | 0.29 |
| 55 | 0.25 |
| 61 | 0.21 |
| 65 | 0.39 |
| 78 | 0.39 |
| 123 | 0.19 |
| 126 | 0.15 |
| 128 | 0.31 |
| 134 | 0.20 |
| 135 | 0.39 |
| 137 | 0.27 |
| 142 | 0.18 |
| 160 | 0.49 |
| 163 | 0.61 |
| 164 | 1.13 |
| 165 | 1.32 |
| 168 | 7.98 |
| 169 | 1.80 |
| 170 | 1.19 |
| 171 | 0.51 |
| 172 | 0.11 |
| Comp. Comp'd 1 | 29 |
| Comp. Comp'd 2 | 46 |
| Comp. Comp'd 3 | >100 |
| Comp. Comp'd 4 | 31.6 |

(Comp. Comp'd 1)

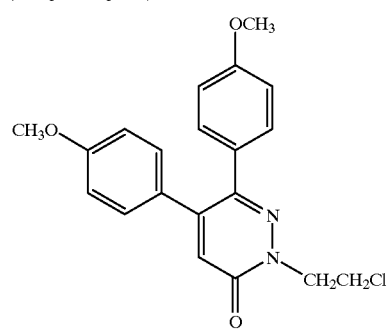

(Comp. Comp'd 2)

(Comp. Comp'd 3)

(Comp. Comp'd 4)

Test 2

Inhibitory Activity Against TNF-α Production

RAW 264.7 cells were cultured until confluence on DMEM culture with 10% fetal bovine serum (FBS), and were diluted to 1×10$^6$ cells/ml with the same medium and then inoculated at 100 μl/well to a 96-well plate. To the cells, a test sample which had been diluted with the same medium and lipopolysaccharide of 4 μg/ml was added at 50 μl/well, respectively. Subsequent to culturing for 20 hours, the cultures were collected.

Making use of cytotoxicity to L-929 cell strain, a TNF-α sensitive cell strain, the amount of TNF-α in each of the cultures was measured as will be described next. Described specifically, L-929 cells which had been cultured on MEM medium with 10% FBS added thereto were diluted to 2×10$^5$ cells/ml with the same medium, and were then inoculated at 100 μl/well to a 96-well plate. Subsequent to overnight incubation, standard TNF-α solutions, or 100-fold, 200-fold and 500-fold dilute solutions of the above-described culture of RAW 264.7 cells were added at 50 μl/well, and actinomycin D (4 μg/ml) was also added at 50 μl/well, followed by further culturing for 20 hours. Twenty hours later, each well was washed with PBS, viable cells were stained with crystal violet, and the inhibitory activity against TNF-α production was determined with reference to a standard curve of TNF-α. The results are shown in Table 2.

Inhibitory Activity Against IL-6 Production

RAW 264.7 cells, which had been cultured until confluence on DMEM culture with 10% fetal bovine serum (FBS) added thereto, were diluted to $1 \times 10^6$ cells/ml with the same medium, and were then inoculated at 100 μl/well to a 96-well plate. A test sample which had been diluted with the same medium and lipopolysaccharide of 4 μg/ml in concentration was added at 50 μl/well, respectively. Subsequent to culturing for 20 hours, the cultures were collected.

The amount of IL-6 in each of the thus-obtained cultures of RAW 264.7 cells was measured by ELISA, and the inhibitory activity against IL-6 production was determined with reference to a standard curve of IL-6. The results are shown in Table 2.

TABLE 2

| | Inhibitory Activity against TNF-α and IL-6 Production | |
|---|---|---|
| Test compound (Example No.) | TNF-α $IC_{50}$ (μM) | IL-6 $IC_{50}$ (μM) |
| 163 | 1.2 | 0.40 |
| Comparative Compound 1 | 10 | 65 |
| Comparative Compound 2 | 26 | 44 |

As is apparent from Tests 1 and 2 described above, the compounds according to the present invention have been found to have extremely good IL-1β inhibitory activity compared with Comparative Compounds 1 to 4, which are compounds disclosed in EUR. J. MED. CHEM., 14, 53–60, 1979 and are known to have anti-inflammatory and analgesic action.

Test 3

In accordance with the disclosure of Nature 283, 666–668, 1980, therapeutic effects for arthritis were evaluated by using collagen-induced arthritis models of mice. As a result, the compound according to the present invention showed excellent arthritis treatment effects as shown in Table 3.

TABLE 3

| Test comp'd (Ex. No.) | Dose (mg/kg, P.O.) | Percent[1] inhibition to arthritis development | Percent[2] inhibition to swelling |
|---|---|---|---|
| 51 | 1 | 40 | 33.3 |
| 51 | 3 | 50 | 77.4 |

[1]Determined depending on the existence or non-existence of swelling.
[2]Determined by quantitation of swelling.

Test 4

The compound of Example 51 was administered orally once a day to rats and dogs for 2 weeks to determine its maximum no-effect level (the amount which does not show toxicity). As a result, no toxicity was observed at all at the dose levels of the compound shown in Table 4, so that the compounds according to the present invention have been found to have high safety.

TABLE 4

| Test compound (Example No.) | Maximum no-effect level (rat) | Maximum no-effect level (dog) |
|---|---|---|
| 51 | 100 mg/kg | 30 mg/kg |

Capability of Exploitation in Industry

The pyridazine derivatives (1) and their salts, which pertain to the present invention, have excellent inhibitory activity against interleukin-1β production, and are useful as medicines such as preventives and therapeutics for immune system diseases, inflammatory diseases and ischemic diseases.

What is claimed is:

1. A pyridazine compound having the formula (1):

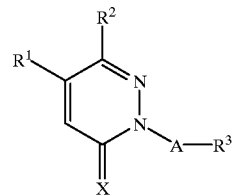

wherein:

$R^1$ is phenyl or pyridyl which is each unsubstituted or substituted by 1 to 3 substituents selected from the group consisting of halogen and lower alkoxy;

$R^2$ is phenyl which is unsubstituted or substituted at the 4-position thereof with lower alkoxy, lower alkylthio, lower alkylsulfinyl or lower alkylsulfonyl, and at the other positions by 1 or 2 substituents selected from the group consisting of halogen, lower alkoxyl, lower alkylthio, lower alkylsulfinyl and lower alkylsulfonyl;

$R^3$ is lower alkoxy, lower cycloalkyl; or phenyl, pyridyl or phenyloxy which is each unsubstituted or substituted by 1 to 3 substituents selected from the group consisting of halogen, lower alkyl, lower alkoxy, carboxy, lower alkoxycarbonyl, nitro, amino, lower alkylamino and lower alkylthio; piperidino, piperidyl, piperazino or morpholino, which is each unsubstituted or subsituted by 1 to 3 substituents selected from the group consisting of halogen and lower alkyl; aminocarbonyl which is unsubstituted or subsituted by benzyl, phenethyl, and 1 to 3 substituents selected from the group consisting of halogen and lower alkyl; or lower alkylcarbonyl; and A is a linear or branched lower alkylene group having 1 to 6 carbon atoms or linear or branched alkenylene having 2 to 9 carbon atoms; or a pharmaceutically acceptable salt thereof.

2. A pyridazine compound having the formula (1A):

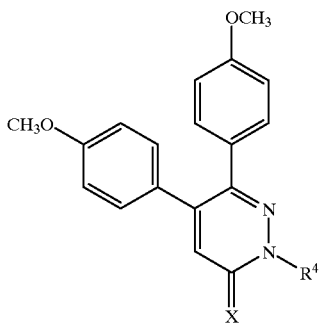

(1A)

wherein:
R⁴ is linear or branched lower alkyl or lower alkenyl, lower cycloalkyl or lower cycloalkylmethyl; and
X is oxygen or sulfur; or a pharmaceutically acceptable salt thereof.

3. The pyridazine compound or salt thereof of claim 1, wherein:
R² is phenyl which is subsituted at the 4-position thereof with $C_1$–$C_6$-alkoxy, $C_1$–$C_6$-alkylthio $C_1$–$C_6$-alkylsulfinyl or $C_1$–$C_6$-alkylsulfonyl.

4. The pyridazine compound or salt thereof of claim 3, wherein:
R² is phenyl which is substituted at the 4-position thereof with $C_1$–$C_6$-alkoxy or $C_1$–$C_6$-alkylthio.

5. A pyridazine compound or salt thereof, which is 5,6-bis(4-methoxyphenyl)-2-ethyl-2H-pyridazin-3-one, 5,6-bis(4-methoxyphenyl)-2-methyl- 2H-pyridazin-3-one, 5,6-bis(4-methoxyphenyl)-2-isopropyl-2H-pyridazin-3-one, 5,6-bis(4-methoxyphenyl)-2-isobutyl-2H-pyridazin-3-one, 2-allyl-5,6-bis(4-methoxyphenyl)-2H-pyridazin-3-one, 5,6-bis(4-methoxyphenyl)-2-cyclopropyl-2H-pyridazin-3-one, 5,6-bis(4-methoxyphenyl)-2-cyclopropylmethyl-2H-pyridazin-3-one, 5,6-bis(4-methoxyphenyl)-2-cyclopropylmethyl-2H-pyridazine-3-thione, 5,6-bis(4-methoxyphenyl)-2-cyclopentyl-2H-pyridazin-3-one, 5,6-bis(4-methoxyphenyl)-2-cyclopentylmethyl-2H-pyridazin-3-one, 5,6-bis(4-methoxyphenyl)-2-(4-chlorocinnamyl)-2H-pyridazin-3-one, 5-(4-chlorophenyl)-6-(4-methoxyphenyl)-2-benzyl-2H-pyridazin-3-one, 5,6-bis(4-methoxyphenyl)-2-benzyl-2H-pyridazine-3-thione, 5,6-bis(3-fluoro-4-methoxyphenyl)2-ethyl-2H-pyridazin-3-one, 5-(4-chlorophenyl)-6-(4-methylsulfinylphenyl)-2-benzyl-2H-pyridazin-3-one, 5-(4-chlorophenyl)-6-(4-methylsulfonylphenyl)-2-benzyl-2H-pyridazin-3-one, 5-(4-chlorophenyl)-6-(4-methylthiophenyl)-2-(3-pyridylmethyl)-2H-pyridazin-3-one, 5-(4-chlorophenyl)-6-(4-methylsulfinylphenyl)-2-(3-pyridylmethyl)-2H-pyridazin-3-one, 5-(4-chlorophenyl)-6-methylsulfonylphenyl)-2-(3-pyridylmethyl)-2H-pyridazin-3-one, 2-(4-chlorobenzyl)-6-(4-methoxyphenyl)-5-(4-pyridyl)-2H-pyridazin-3-thione, 5,6-bis(4-methoxyphenyl)-2-(3-pyridylmethyl)-2H-pyridazin-3-one, or 5,6-bis(4-methoxyphenyl)-2-(4-pyridylmethyl)-2H-pyridazin-3-one.

6. A pyridazine compound or salt thereof, which is 5-(4-chlorophenyl)-6-(4-methylthiophenyl)-2-benzyl-2H-pyridazine-3-one, 5-(4-chlorophenyl)-6-(4-methylsulfinylphenyl)-2-benzyl-2H-pyridazine-3-one, 5-(4-chlorophenyl)-6-(4-methylsulfonylphenyl)-2-benzyl-2H-pyridazine-3-one, 5-(4-chlorophenyl)-6-(4-methylthiophenyl)-2-(3-pyridylmethyl)-2H-pyridazine-3-one, 5-(4-chlorophenyl)-6-(4-methylsulfinylphenyl)-2-(3-pyridylmethyl)-2H-pyridazine-3-one, 5-(4-chlorophenyl)-6-(4-methylsulfonylphenyl)-2-(3-pyridylmethyl)-2H-pyridazine-3-thione, 5,6-bis(4-methoxyphenyl-2-(4-chlorocinnamyl)-2H-pyridazine-3-one, 2-(4-chlorobenzyl)-6-(4-methoxyphenyl-5-(4-pyridyl)-2H-pyridazine-3-thione, 5,6-bis(4-methoxyphenyl)-2-2(3-pyridylmethyl)-2H-pyridazine-3-one, 5,6-bis(4-methoxyphenyl)-2-ethyl-2H-pyridazine-3-one or 5,6-bis(4-methoxyphenyl)-2-(4-pyridylmethyl)-2H-pyridazine-3-one.

7. A pharmaceutical composition for inhibiting interleukin-1β production in a mammal, comprising:
a) one or more of the compound of claim 1, or salt thereof, in an amount effective to effect said inhibition; and
b) a pharmaceutically acceptable carrier.

8. A pharmaceutical composition for inhibiting interleukin-1β production in a mammal, comprising:
a) an effective amount of one or more compounds selected from the group consisting of 5,6-bis(4-methoxyphenyl)-2-ethyl-2H-pyridazin-3-one, 5,6-bis(4-methoxyphenyl)-2-methyl-2H-pyridazin-3-one, 5,6-bis(4-methoxyphenyl)-2-isopropyl-2H-pyridazin-3-one; 5,6-bis(4-methoxyphenyl)-2-isobutyl-2H-pyridazin-3-one, 2-allyl-5,6-bis(4-methoxyphenyl)-2H-pyridazin-3-one, 5,6-bis(methoxyphenyl)-2-cyclopropyl-2H-pyridazin-3-one, 5,6-bis(4-methoxyphenyl)-2-cyclopropylmethyl-2H-pyridazin-3-one, 5,6-bis(4-methoxyphenyl)-2-cyclopropylmethyl-2H-pyridazine-3-thione, 5,6-bis(4-methoxyphenyl)-2-cyclopentyl-2H-pyridazin-3-one, 5,6-bis(4-methoxyphenyl)-2-cyclopentylmethyl-2H-pyridazine-3-one, 5,6-bis(4-methoxyphenyl)-2-(4-chlorocinnamyl)-2H-pyridazin-3-one, 5-(4-chlorophenyl)-6-(4-methylthiophenyl-2-benzyl-2H-pyridazin-3-one, 5,6-bis(4-methoxyphenyl)-2-benzyl-2H-pyridazine-3-thione, 5,6-bis(3-fluoro-4-methoxyphenyl)-2-ethyl-2H-pyridazin-3-one, 5-(4-chlorophenyl)-6-(4-methylsulfinylphenyl)-2-benzyl-2H-pyridazin-3-one, 5-(4-chlorophenyl)-6-(4-methylsulfonylphenyl)-2-benzyl-2H-pyridazin-3-one, 5-(4-chlorophenyl)-6-(4-methylthiophenyl)-2-(3-pyridylmethyl)-2H-pyridazin-3-one, 5-(4-chlorophenyl)-6-(4-methylsulfinylphenyl)-2-(3-pyridylmethyl)-2H-pyridazin-3-one, 5-(4-chlorophenyl)-6-(4-methylsulfonylphenyl)-2-(3-pyridylmethyl)-2H-pyridazin-3-one, 2-(4-chlorobenzyl)-6-(4-methoxyphenyl)-5-(4-pyridyl)-2H-pyridazin-3-thione, 5,6-bis(4-methoxyphenyl)-2-(3-pyridylmethyl)-2H-pyridazin-3-one, and 5,6-bis(4-methoxyphenyl)-2-(4-pyridylmethyl)-2H-pyridazin-3-one; or a pharmaceutically acceptable salt thereof; and
b) a pharmaceutically acceptable carrier.

9. A method for treating arthritis in a mammal, which comprises administering one or more of the compounds of claim 1, to a mammal in need thereof.

10. The method of claim 9, wherein said mammal is a human.

* * * * *

UNITED STATES PATENT AND TRADEMARK OFFICE
CERTIFICATE OF CORRECTION

PATENT NO.    : 6,348,468 B1
DATED         : February 19, 2002
INVENTOR(S)   : Ohkuchi et al.

It is certified that error appears in the above-identified patent and that said Letters Patent is hereby corrected as shown below:

<u>Column 69,</u>
Lines 26-27, "$C_1$-$C_6$-alkylthio $C_1$-$C_6$-alkylsulfinyl" should read -- $C_1$-$C_6$-alkylthio, $C_1$-$C_6$-alkylsulfinyl --
Lines 45-46, "5-(4-chlorophenyl)-6(4-methoxyphenyl)-2-benzyl-2H-pyridazin-3-one" should read -- 5-(4-chlorophenyl)-6-(4-methylthiophenyl)-2-benzyl-2H-pyridazin-3-one --.
Lines 55-56, "5-(4-chlorophenyl)-6-methylsulfonylphenyl)-2-(3-pyridylmethyl)-2H-pyridazin-3-one" should read -- 5-(4-chlorophenyl)-6-(4-methylsulfonylphenyl)-2-(3-pyridylmethyl)-2H-pyridazin-3-one Signed and Sealed this Eleventh Day of June, 2002

*Attest:*

JAMES E. ROGAN
*Attesting Officer*       *Director of the United States Patent and Trademark Office*